(12) United States Patent
Newberry

(10) Patent No.: US 10,238,346 B2
(45) Date of Patent: Mar. 26, 2019

(54) SYSTEM AND METHOD FOR A BIOSENSOR INTEGRATED IN A VEHICLE

(71) Applicant: Sanmina Corporation, San Jose, CA (US)

(72) Inventor: Robert Steven Newberry, New Hope, AL (US)

(73) Assignee: Sanmina Corporation, San Jose, CA (US)

( * ) Notice: Subject to any disclaimer, the term of this patent is extended or adjusted under 35 U.S.C. 154(b) by 0 days.

(21) Appl. No.: 15/811,479

(22) Filed: Nov. 13, 2017

(65) Prior Publication Data

US 2018/0116604 A1 May 3, 2018

Related U.S. Application Data

(63) Continuation-in-part of application No. 15/718,721, filed on Sep. 28, 2017, and a continuation-in-part of application No. 15/680,991, filed on Aug. 18, 2017, now Pat. No. 9,968,289, said application No. 15/718,721 is a continuation of application No.
(Continued)

(51) Int. Cl.
*A61B 5/1455* (2006.01)
*A61B 5/00* (2006.01)
*A61B 5/024* (2006.01)
*A61B 5/145* (2006.01)

(52) U.S. Cl.
CPC .......... *A61B 5/7275* (2013.01); *A61B 5/0002* (2013.01); *A61B 5/0022* (2013.01); *A61B 5/02416* (2013.01); *A61B 5/1455* (2013.01); *A61B 5/14532* (2013.01); *A61B 5/14551* (2013.01); *A61B 5/6817* (2013.01);
(Continued)

(58) Field of Classification Search
None
See application file for complete search history.

(56) References Cited

U.S. PATENT DOCUMENTS 6,985,763 B2 1/2006 Boas et al.
9,149,216 B2 10/2015 Eisen et al.
(Continued)

OTHER PUBLICATIONS

KC Manhesh et al., Wearable Wireless Intelligent Multi-Parameter Health Monitoring Watch, 2013, Texas Instruments India Educators' Conference, IEEE, p. 61-64.
(Continued)

*Primary Examiner* — Eric Winakur
*Assistant Examiner* — Marjan Fardanesh
(74) *Attorney, Agent, or Firm* — Loza & Loza, LLP; Julio M. Loza; Jessica W. Smith

(57) ABSTRACT

A vehicle includes one or more integrated biosensors, such as finger sensors or other user touchpoints. The integrated biosensors are configured to obtain biosensor data, such as a patient's vitals or concentrations of substances in the blood flow of a user. A control module of a vehicle receives the biosensor data and controls operation of one or more systems of the vehicle in response to the biosensor data. The control module may also present the biosensor data on a display of the vehicle and receive user commands to control the biosensors. The control module may also generate warnings for display in response to the biosensor data exceeding one or more predetermined thresholds.

28 Claims, 43 Drawing Sheets

Related U.S. Application Data

15/622,941, filed on Jun. 14, 2017, now Pat. No. 9,788,767, application No. 15/811,479, which is a continuation-in-part of application No. 15/490,813, filed on Apr. 18, 2017, now Pat. No. 9,980,676, and a continuation-in-part of application No. 15/489,391, filed on Apr. 17, 2017, now Pat. No. 9,974,451, and a continuation-in-part of application No. 15/485,816, filed on Apr. 12, 2017, and a continuation-in-part of application No. 15/404,117, filed on Jan. 11, 2017, said application No. 15/485,816 is a continuation of application No. 15/276,760, filed on Sep. 26, 2016, now Pat. No. 9,636,457, said application No. 15/489,391 is a continuation of application No. 15/275,444, filed on Sep. 25, 2016, now Pat. No. 9,642,538, said application No. 15/490,813 is a continuation of application No. 15/275,388, filed on Sep. 24, 2016, now Pat. No. 9,642,578, application No. 15/811,479, which is a continuation-in-part of application No. 14/866,500, filed on Sep. 25, 2015.

(60) Provisional application No. 62/463,104, filed on Feb. 24, 2017.

(52) U.S. Cl.
CPC ............ *A61B 5/743* (2013.01); *A61B 5/6826* (2013.01); *A61B 5/7225* (2013.01); *A61B 2560/0223* (2013.01)

(56) References Cited

U.S. PATENT DOCUMENTS

| | | |
|---|---|---|
| 2008/0208019 A1 | 8/2008 | Nitzan |
| 2012/0330126 A1 | 12/2012 | Hope et al. |
| 2013/0060098 A1 | 3/2013 | Thomsen et al. |
| 2013/0110311 A1 | 5/2013 | Steeg et al. |
| 2013/0310669 A1 | 11/2013 | Meir Nitzan |
| 2014/0112940 A1 | 4/2014 | Lane |
| 2014/0243648 A1 | 8/2014 | Dubielczyk |
| 2015/0094914 A1 | 4/2015 | Abreu |
| 2015/0109617 A1 | 4/2015 | Gilbert et al. |
| 2015/0148622 A1 | 5/2015 | Moyer et al. |
| 2015/0150453 A1 | 6/2015 | Abreu |
| 2015/0182172 A1 | 7/2015 | Shelley et al. |
| 2015/0229341 A1* | 8/2015 | Fung .................. H04B 1/10 702/191 |
| 2015/0282747 A1 | 10/2015 | Thiele |
| 2015/0366471 A1 | 12/2015 | LeBoeuf et al. |
| 2016/0018257 A1 | 1/2016 | Mirov et al. |
| 2016/0058347 A1 | 3/2016 | Reichgott et al. |
| 2016/0066863 A1 | 3/2016 | Thaveeprungsriporn et al. |
| 2016/0100781 A1 | 4/2016 | Bechtel et al. |

OTHER PUBLICATIONS

Abdallah et al., Design of a Compact Multi-Sensor System for Non-Invasive Glucose Monitoring Using Optical Spectroscopy, International Conference on Electronics, Biomedical Engineering and its Applications (ICEBEA '2012), Jan. 7-8, 2012, p. 310-317.
Forst et al., Cardiovascular Effects of Disturbed Insulin Activity in Metabolic Syndrome and in Type 2 Diabetic Patients, Insulin Secretion and Action, Horm Metab Res; 2009, 41; p. 123-131.
Mohamed Elgendi, On the Analysis of Fingertip Photoplethysmogram Signals, Current Cardiology Reviews, 2012, 8, p. 14-25, Bentham Science Publishers.
Wikipedia, Cytochrome P450, Dec. 31, 2015, p. 1-12.
Oliver Wieben, Light Absorbance in Pulse Oximetry, Taylor & Francis, 1997, IOP Publishing, p. 1-20.
Wikipedia, Photoplethysmogram, Jul. 25, 2015, p. 1-4.
PCT/US2016/053631 . Int'l search Report & Written Opinion (dated Dec. 8, 2016).

* cited by examiner

Aug 11, 2017

Aug 11, 2017

Aug 11, 2017

Aug 11, 2017

SYSTEM AND METHOD FOR A BIOSENSOR INTEGRATED IN A VEHICLE

CROSS REFERENCE TO RELATED APPLICATIONS

The present application claims priority under 35 U.S.C. § 120 as a continuation in part application to U.S. Utility application Ser. No. 15/490,813 entitled, "SYSTEM AND METHOD FOR HEALTH MONITORING USING A NON-INVASIVE, MULTI-BAND BIOSENSOR," filed Apr. 18, 2017, and hereby expressly incorporated by reference herein, which claims priority under 35 U.S.C. § 120 as a continuation application to U.S. Utility application Ser. No. 15/275,388 entitled, "SYSTEM AND METHOD FOR HEALTH MONITORING USING A NON-INVASIVE, MULTI-BAND BIOSENSOR," filed Sep. 24, 2016, and hereby expressly incorporated by reference herein.

The present application claims priority under 35 U.S.C. § 120 as a continuation in part application to U.S. Utility application Ser. No. 15/680,991 entitled, "System and Method for Detecting a Sepsis Condition," filed Aug. 18, 2017, and hereby expressly incorporated by reference herein.

The present application claims priority under 35 U.S.C. § 120 as a continuation in part application to U.S. Utility application Ser. No. 15/489,391, entitled, "System and Method for a Biosensor Monitoring and Tracking Band," filed Apr. 12, 2017, hereby expressly incorporated by reference herein, which claims priority under 35 U.S.C. § 120 as a continuation application to U.S. Utility application Ser. No. 15/275,444, entitled, "System and Method for a Drug Delivery and Biosensor Patch," filed Sep. 25, 2016, hereby expressly incorporated by reference herein.

The present application claims priority under 35 U.S.C. § 120 as a continuation in part application to U.S. Utility application Ser. No. 15/485,816, entitled, "System and Method for a Drug Delivery and Biosensor Patch," filed Apr. 12, 2017, hereby expressly incorporated by reference herein, which claims priority under 35 U.S.C. § 120 as a continuation application to U.S. Utility application Ser. No. 15/276,760, entitled, "System and Method for a Drug Delivery and Biosensor Patch," filed Sep. 26, 2016, both are hereby expressly incorporated by reference herein.

The present application claims priority under 35 U.S.C. § 120 as a continuation in part application to U.S. patent application Ser. No. 15/718,721 entitled, "SYSTEM AND METHOD FOR MONITORING NITRIC OXIDE LEVELS USING A NON-INVASIVE, MULTI-BAND BIOSENSOR," filed Sep. 28, 2017 and hereby expressly incorporated by reference herein, which claims priority as a continuation application to U.S. Utility application Ser. No. 15/622,941 entitled, "SYSTEM AND METHOD FOR MONITORING NITRIC OXIDE LEVELS USING A NON-INVASIVE, MULTI-BAND BIOSENSOR," filed Jun. 14, 2017, and hereby expressly incorporated by reference herein, which claims priority under 35 U.S.C. § 119 to U.S. Provisional Application No. 62/463,104 entitled, "SYSTEM AND METHOD FOR MONITORING NITRIC OXIDE LEVELS USING A NON-INVASIVE, MULTI-BAND BIOSENSOR," filed Feb. 24, 2017, and hereby expressly incorporated by reference herein.

The present application claims priority under 35 U.S.C. § 120 as a continuation in part application to U.S. patent application Ser. No. 15/404,117 entitled, "SYSTEM AND METHOD FOR HEALTH MONITORING INCLUDING A USER DEVICE AND BIOSENSOR," filed Jan. 11, 2017, and hereby expressly incorporated by reference herein.

The present application claims priority under 35 U.S.C. § 120 as a continuation in part application to U.S. patent application Ser. No. 14/866,500 entitled, "SYSTEM AND METHOD FOR Glucose Monitoring," filed Sep. 25, 2015, and hereby expressly incorporated by reference herein.

FIELD

This application relates to a systems and methods of non-invasive, autonomous health monitoring, and in particular a health monitoring sensor that monitors a patient's vitals and detects concentration levels or indicators of alcohol in blood flow.

BACKGROUND

A patient's vitals, such as temperature, blood oxygen levels, blood pressure, etc., may need to be monitored periodically typically using one or more instruments. For example, instruments for obtaining vitals of a patient include blood pressure cuffs, thermometers, $SaO_2$ measurement devices, glucose level meters, etc. Often, multiple instruments must be brought to a patient's room by a caretaker, and the measurements collected using the multiple instruments. This monitoring process can be time consuming, inconvenient and is not always continuous. It may also disrupt sleep of the patient. The measurements of the vitals must then be manually recorded into the patient's electronic medical record.

In addition, detection of substances and measurement of concentration level or indicators of various substances in a patient's blood vessels is important in health monitoring. Currently, detection of concentration levels of blood substances is performed by drawing blood from a blood vessel using a needle and syringe. The blood sample is then transported to a lab for analysis. This type of monitoring is invasive, non-continuous and time consuming.

One current non-invasive method is known for measuring the oxygen saturation of blood using pulse oximeters. Pulse oximeters detect oxygen saturation of hemoglobin by using, e.g., spectrophotometry to determine spectral absorbencies and determining concentration levels of oxygen based on Beer-Lambert law principles. In addition, pulse oximetry may use photoplethysmography (PPG) methods for the assessment of oxygen saturation in pulsatile arterial blood flow. The subject's skin at a 'measurement location' is illuminated with two distinct wavelengths of light and the relative absorbance at each of the wavelengths is determined. For example, a wavelength in the visible red spectrum (for example, at 660 nm) has an extinction coefficient of hemoglobin that exceeds the extinction coefficient of oxihemoglobin. At a wavelength in the near infrared spectrum (for example, at 940 nm), the extinction coefficient of oxihemoglobin exceeds the extinction coefficient of hemoglobin. The pulse oximeter filters the absorbance of the pulsatile fraction of the blood, i.e. that due to arterial blood (AC components), from the constant absorbance by nonpulsatile venous or capillary blood and other tissue pigments (DC components), to eliminate the effect of tissue absorbance to measure the oxygen saturation of arterial blood. Such PPG techniques are heretofore been limited to determining oxygen saturation.

As such, there is a need for a continuous and non-invasive biosensor that measures patient vitals and monitors concentration levels or indicators of one or more substances in blood flow.

SUMMARY

According to a first aspect, a biosensor is configured for integration in a vehicle and includes a temperature sensor configured to measure a temperature of an occupant of the vehicle and a photoplethysmography (PPG) circuit configured to emit light at a plurality of wavelengths directed at skin tissue of the occupant of the vehicle and obtain a plurality of spectral responses around the plurality of wavelengths of light. The biosensor also includes a processing circuit configured to process the plurality of spectral responses and obtain biosensor data of the occupant using the plurality of spectral responses, wherein the biosensor data includes a temperature, an oxygen saturation level, a heart rate and a blood alcohol level. The processing circuit is further configured to generate a health message for transmission to a vehicle control system including the biosensor data of the occupant.

According to a second aspect, a biosensor is configured for integration in a vehicle and includes a temperature sensor in an integrated biosensor configured to measure a skin temperature of an occupant and a PPG circuit in the integrated biosensor configured to emit light at a plurality of wavelengths directed at skin tissue and obtain a plurality of spectral responses around the plurality of wavelengths of light. A processing circuit is configured to process the plurality of spectral responses and obtain biosensor data using the plurality of spectral responses, wherein the biosensor data includes an oxygen saturation level, a heart rate and a concentration level of at least one other substance in blood flow. The processing circuit may be further configured to generate an occupant health message including the biosensor data of the occupant for display on a vehicle display.

According to a third aspect, a biosensor includes a PPG circuit configured for integration in a vehicle and configured to emit light at a plurality of wavelengths directed at skin tissue of a user of the vehicle and obtain a plurality of spectral responses around the plurality of wavelengths of light. A processing circuit is configured to process the plurality of spectral responses to obtain biosensor data using the plurality of spectral responses, wherein the biosensor data includes a blood alcohol level and transmit a health message including the blood alcohol level of the user to a vehicle control system.

According to a fourth aspect, a biosensor is configured for integration in a vehicle and includes a temperature sensor configured to measure a temperature of an occupant and a photoplethysmography (PPG) circuit configured to emit light at a plurality of wavelengths directed at skin tissue of the occupant and obtain a plurality of spectral responses around the plurality of wavelengths of light. A processing circuit is configured to process the plurality of spectral responses to obtain a plurality of health measurements, wherein the plurality of health measurements include a heart rate, an oxygen saturation level, a temperature, a vasodilation level, and a concentration level of at least one other substance in blood flow. The processing circuit may compare one or more of the plurality of measurements to one or more predetermined thresholds, determine the one or more of the plurality of measurements exceeds at least one of the predetermined thresholds and generate an occupant health message to a vehicle control system.

According to a one or more of the above aspects, the processing circuit is further configured to obtain a concentration level of an indicator in blood flow using the plurality of spectral responses, wherein the indicator is related to blood alcohol level in blood flow. For example, the indicator includes a P450 enzyme and one or more of: an ADH related enzyme or ethanol. The processing circuit is further configured to determine the blood alcohol level using the indicator. The processing circuit is further configured to compare the blood alcohol level to a predetermined threshold, determine the blood alcohol level exceeds the predetermined threshold and generate a command to prevent operation of the vehicle.

According to a one or more of the above aspects, the processing circuit is further configured to determine a level of vasodilation by determining a change in intensity from one or more spectral responses of the plurality of spectral responses due to blood flow and mapping the change in intensity to the level of vasodilation, wherein the one or more spectral responses are around one or more of: ultraviolet (UV) light or infrared (IR) light.

According to a one or more of the above aspects, the processing circuit is further configured to determine a concentration level of at least one additional substance in blood flow using the plurality of spectral responses. For example, the processing circuit is further configured to determine a concentration level of nitric oxide (NO) in blood flow using the plurality of spectral responses or a concentration level of glucose in blood flow using the plurality of spectral responses.

According to a one or more of the above aspects, the processing circuit is further configured to determine a blood group using the plurality of spectral responses.

According to a one or more of the above aspects, the processing circuit is further configured to determine a risk of an infection using the plurality of spectral responses.

DETAILED DESCRIPTION

The word "exemplary" or "embodiment" is used herein to mean "serving as an example, instance, or illustration." Any implementation or aspect described herein as "exemplary" or as an "embodiment" is not necessarily to be construed as preferred or advantageous over other aspects of the disclosure. Likewise, the term "aspects" does not require that all aspects of the disclosure include the discussed feature, advantage, or mode of operation.

Embodiments will now be described in detail with reference to the accompanying drawings. In the following description, numerous specific details are set forth in order to provide a thorough understanding of the aspects described herein. It will be apparent, however, to one skilled in the art, that these and other aspects may be practiced without some or all of these specific details. In addition, well known steps in a method of a process may be omitted from flow diagrams presented herein in order not to obscure the aspects of the disclosure. Similarly, well known components in a device may be omitted from figures and descriptions thereof presented herein in order not to obscure the aspects of the disclosure.

Overview

One or more embodiments have been described herein for a vehicle with one or more integrated biosensors. Due to its compact form factor, the biosensors may be integrated as finger sensors or as other compact form factors, such as on a wrist band or ear piece or other type of sensors in the vehicle. The integrated biosensors include one or more sensors for detecting biosensor data, such as a patient's vitals or concentrations of substances in the blood flow of a user. A control module of a vehicle may receive the biosensor data and control operation of one or more systems of the vehicle in response to the biosensor data. The control module may also generate one or more GUIs to present biosensor data on a display of the vehicle as well as present user commands to control the biosensors. The control module may also generate warnings in response to biosensor data exceeding one or more predetermined thresholds.

Embodiment—Biosensor Components

Figure 1:
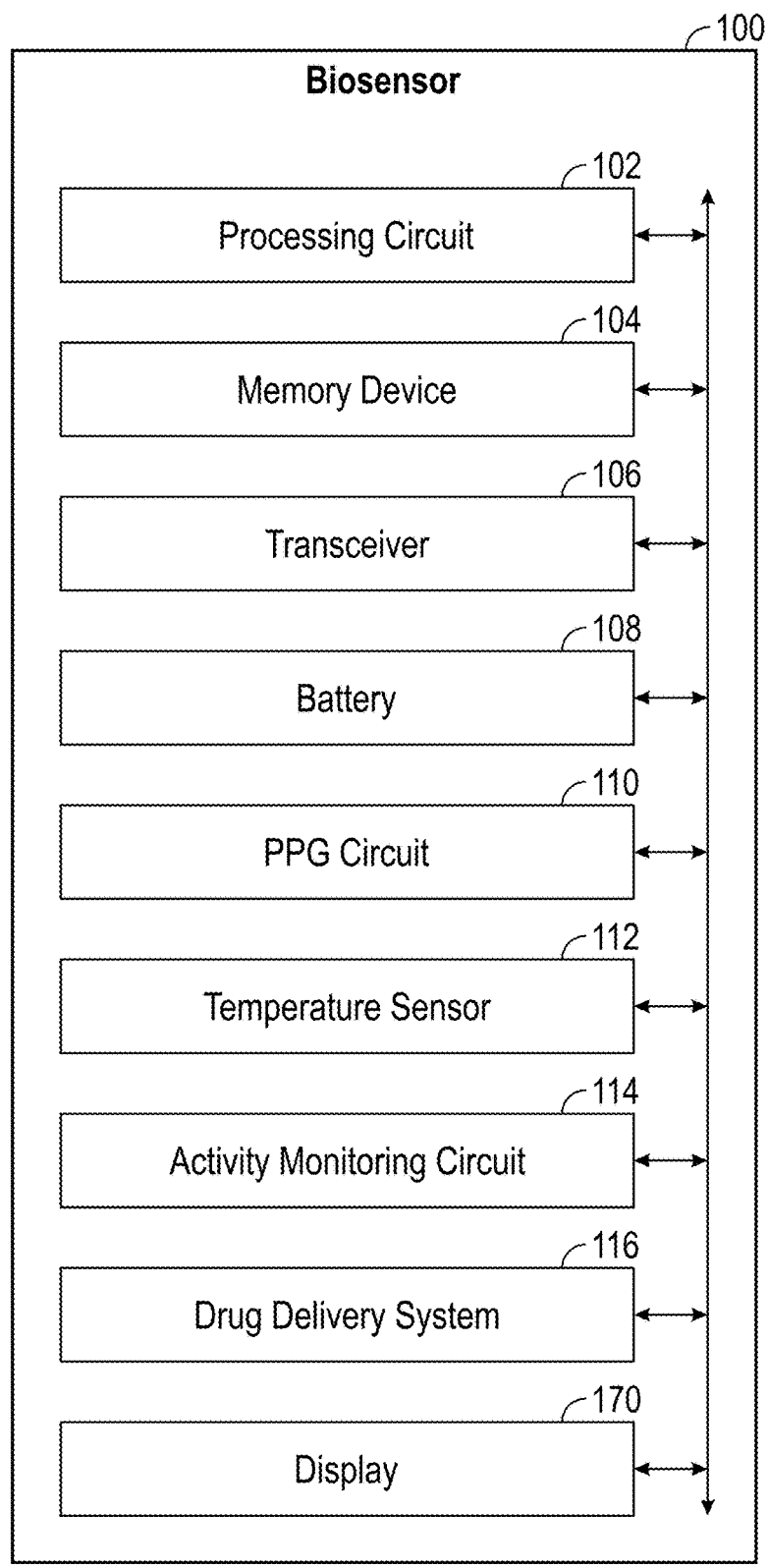
FIG. 1 illustrates a schematic block diagram of an exemplary embodiment of a biosensor.

FIG. 1 illustrates a schematic block diagram of an exemplary embodiment of a biosensor 100. The biosensor 100 includes one or more processing circuits 102 communicatively coupled to a memory device 104. In one aspect, the memory device 104 may include one or more non-transitory processor readable memories that store instructions which when executed by the processing circuit 102, causes the processing circuit 102 to perform one or more functions described herein. The memory device 104 may also include an EEPROM to store a patient identification (ID) 172 that is associated with a patient being monitored by the biosensor 100. The memory device 104 may also store an electronic medical record (EMR) or portion of the EMR associated with the patient being monitored by the biosensor 100. The biosensor data obtained by the biosensor 100 may be stored in the EMR as well as the patient medical history. The processing circuit 102 may be co-located with one or more of the other circuits in the biosensor 100 in a same physical encasement or located separately in a different physical encasement or located remotely. In an embodiment, the biosensor 100 is battery operated and includes a battery 108, such as a lithium ion battery. The biosensor 100 may also include a display configured to display the biosensor data.

The biosensor 100 further includes a transceiver 106. The transceiver 106 may include a wireless or wired transceiver configured to communicate with one or more devices over a LAN, MAN and/or WAN. In one aspect, the wireless transceiver may include a Bluetooth enabled (BLE) transceiver or IEEE 802.11ah, Zigbee, IEEE 802.15-11 or WLAN (such as an IEEE 802.11 standard protocol) compliant transceiver. In another aspect, the wireless transceiver may operate using RFID, short range radio frequency, infrared link, or other short range wireless communication protocol. In another aspect, the wireless transceiver may also include or alternatively include an interface for communicating over a cellular network. In an embodiment, the wireless transceiver may include a thin foil for an antenna that is specially cut and includes a carbon pad contact to a main PCB of the biosensor 100. This type of antenna is inexpensive to manufacture and may be printed on the inside of an enclosure for the biosensor 100 situated away from the skin of the patient to minimize absorption. The transceiver 106 may also include a wired transceiver interface, e.g., a USB port or other type of wired connection, for communication with one or more other devices over a LAN, MAN and/or WAN.

The biosensor 100 includes one or more types of sensors, such as a PPG circuit 110, a temperature sensor 112 or an activity monitoring circuit 114. The temperature sensor 112 is configured to detect a temperature of a patient. For example, the temperature sensor 112 may include an array of sensors (e.g., 16×16 pixels) positioned on a side of the biosensor 100 such that the array of sensors are adjacent to the skin of the patient. The array of sensors then detects an indication of the temperature of the patient from the skin.

The activity monitoring circuit 114 is configured to monitor the activity level of the patient. For example, the activity monitoring circuit 114 may include a multiple axes accelerometer that measures a position of the patient and motion of the patient. In one aspect, the activity monitoring circuit 114 determines periods of activity and rest. For example, the activity monitoring circuit 114 monitors and records periods of rest that meet a predetermined threshold of low motion or activity level, such as sitting, lying, sleeping, etc. The activity monitoring circuit 114 may also monitor and record periods of activity that meet a predetermined threshold of motion or activity level, such as walking, running, lifting, squatting, etc. The biosensor 100 is then configured to measure and store the patient vitals with an indicator of the activity level of the patient. For example, blood oxygen levels may vary greatly in patients with COPD during rest and activity. The vitals of the patient are tracked during periods of activity and rest and the level of activity at time of measuring the vitals is recorded. The biosensor 100 is thus configured to associate measurements of patient vitals with the activity level of the patient.

In another aspect, to help lower power consumption, in an embodiment, the biosensor 100 includes a rest mode. For example, the activity monitoring circuit 114 may signal a rest mode when a patient is asleep or meets a predetermined threshold of low activity level for a predetermined time period. In the rest mode, the biosensor 100 signals one or more modules to halt non-essential processing functions. When the activity monitoring circuit 114 detects a higher activity level exceeding another predetermined threshold for a predetermined time period, the biosensor 100 signals one or more modules to exit rest mode and resume normal functions. This activity monitoring feature helps to save power and extend battery life of the biosensor 100.

In another aspect, the activity monitoring circuit is configured to include a fitness tracker application. The activity monitoring circuit 114 may monitor a number of steps of the patient, amount and length of periods of sleep, amount and length of periods of rest, amount and length of periods of activity, etc.

The biosensor 100 may also include an integrated drug delivery system 116 or be communicatively coupled to a drug delivery system 116. The biosensor 100 may be configured to control delivery of medicine to a patient based on biosensor data obtained by the biosensor 100 as described in more detail in U.S. Provisional Application No. 62/383,313 entitled, "System and Method for a Drug Delivery and Biosensor Patch," filed Sep. 2, 2016, which is expressly incorporated by reference herein.

The biosensor 100 may include a display 170. The biosensor 100 is configured to display a graphical user interface (GUI) that includes biosensor data.

The biosensor 100 also includes a PPG circuit 110. The PPG circuit 110 may be configured to detect oxygen saturation ($SaO_2$ or $SpO_2$) levels in blood flow, as well as heart rate and blood pressure. In addition, the PPG circuit 110 is configured to detect concentration levels or indicators of one or more substances in the blood flow of the patient as described in more detail herein.

Embodiment—PPG Circuit

Figure 2:
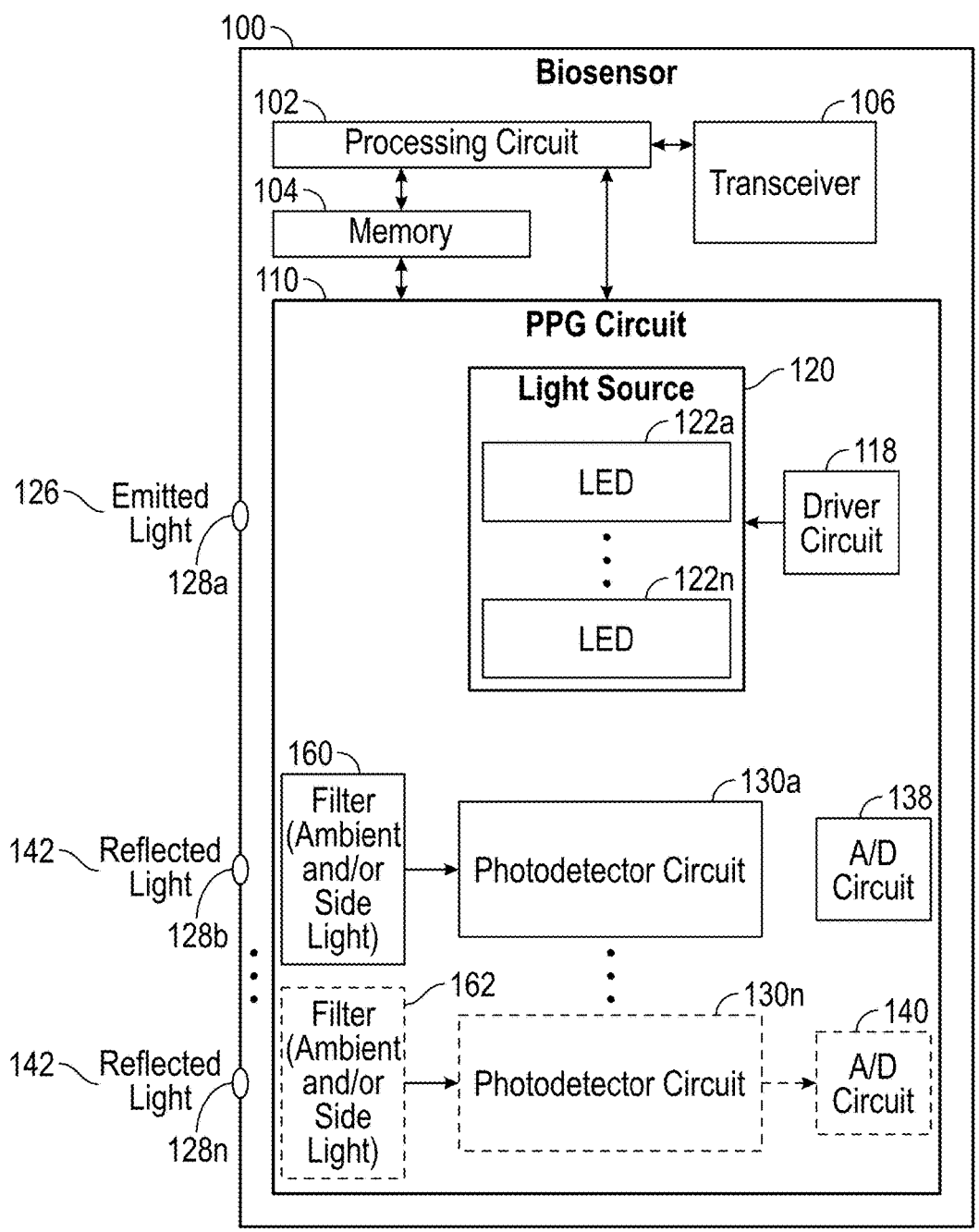
FIG. 2 illustrates a schematic block diagram illustrating an embodiment of the PPG circuit in more detail.

FIG. 2 illustrates a schematic block diagram illustrating an embodiment of the PPG circuit 110 in more detail. The PPG circuit 110 implements photoplethysmography (PPG) techniques for obtaining concentration levels or indicators of one or more substances in pulsating arterial blood flow. The PPG circuit 110 includes a light source 120 having a plurality of light sources, such as LEDs 122a-n, configured to emit light through at least one aperture 128a. The PPG circuit 110 is configured to direct the emitted light at an outer or epidermal layer of skin tissue of a patient. The plurality of light sources are configured to emit light in one or more spectrums, including infrared (IR) light, ultraviolet (UV) light, near IR light or visible light, in response to driver circuit 118. For example, the biosensor 100 may include a first LED 122a that emits visible light and a second LED 122b that emits infrared light and a third LED 122c that emits UV light, etc. In another embodiment, one or more of the light sources 122a-n may include tunable LEDs or lasers operable to emit light over one or more frequencies or ranges of frequencies or spectrums in response to driver circuit 118.

In an embodiment, the driver circuit 118 is configured to control the one or more LEDs 122a-n to generate light at one or more frequencies for predetermined periods of time. The driver circuit 118 may control the LEDs 122a-n to operate concurrently or progressively. The driver circuit 118 is configured to control a power level, emission period and frequency of emission of the LEDs 122a-n. The biosensor 100 is thus configured to emit one or more frequencies of light in one or more spectrums that is directed at the surface or epidermal layer of the skin tissue of a patient.

The PPG circuit 110 further includes one or more photodetector circuits 130a-n. For example, a first photodetector circuit 130 may be configured to detect visible light and the second photodetector circuit 130 may be configured to detect IR light. The first photodetector circuit 130a and the second photodetector circuit 130n may also include a first filter 160 and a second filter 162 configured to filter ambient light and/or scattered light. For example, in some embodiments, only light received at an approximately perpendicular angle to the skin surface of the patient is desired to pass through the filters. The first photodetector circuit 130 and the second photodetector circuit 132 are coupled to a first A/D circuit 138 and a second A/D circuit 140. Alternatively, a single A/D circuit may be coupled to each of the photodetector circuits 130a-n.

In another embodiment, a single photodetector circuit 130 may be implemented operable to detect light over multiple spectrums or frequency ranges. For example, the photodetector circuit 130 may include a Digital UV Index/IR/Visible Light Sensor such as Part No. Si1145 from Silicon Labs™.

The one or more photodetector circuits 130 include a spectrometer or other type of circuit configured to detect an intensity of light as a function of wavelength or frequency to obtain a spectral response. The one or more photodetector circuits 130 detects the intensity of light either transmitted through or reflected from tissue of a patient that enters one or more apertures 128b-n of the biosensor 100. For example, the light may be detected from transmissive absorption (e.g., through a fingertip or ear lobe) or from reflection (e.g., reflected from a forehead or stomach tissue). The photodetector circuits 130 then obtain a spectral response of the detected light by measuring the intensity of light either transmitted or reflected to the photodiodes.

Figure 3:
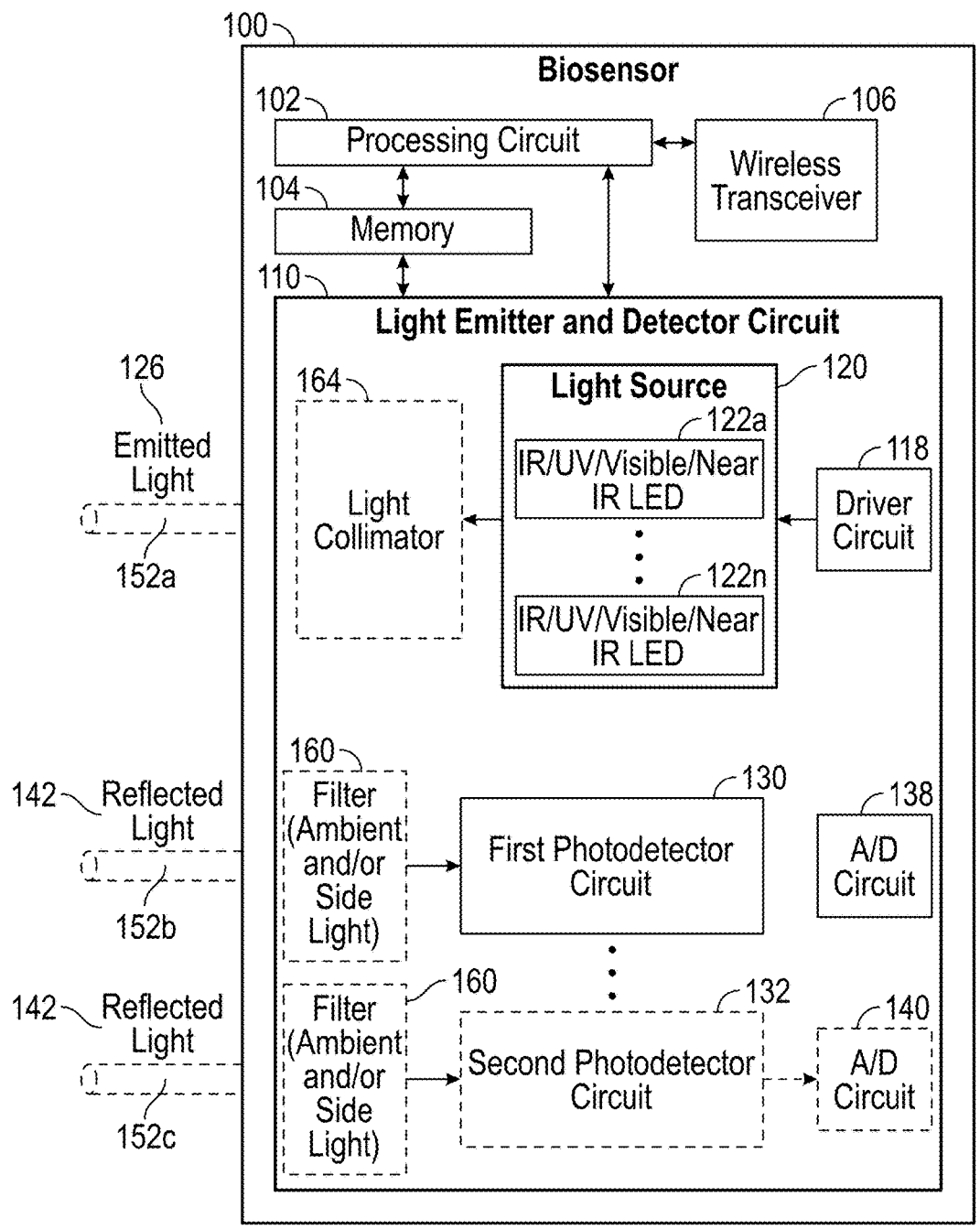
FIG. 3 illustrates a schematic block diagram of another exemplary embodiment of the the PPG circuit.

FIG. 3 illustrates a schematic block diagram of another exemplary embodiment of the the PPG circuit 110. In this embodiment, the biosensor 100 is configured for emitting and detecting light through one or more optical fibers 152a-c. The PPG circuit 110 is optically coupled to a plurality of optical fibers 152a-c. In an embodiment, the plurality of optical fibers 152 includes a first optical fiber 152a optically coupled to the light source 120. An optical coupler (not shown) to spread the angle of light emitted from the optical fiber 152a may also be implemented. The optical fiber 152a may have a narrow viewing angle such that an insufficient area of skin surface is exposed to the light. An optical coupler may be used to widen the viewing angle to increase the area of skin surface exposed to the light.

A second optical fiber 152b is optically coupled to a first photodetector circuit 130 and a third optical fiber 152c is optically coupled to the second photodetector circuit 132. Other configurations and numbers of the plurality of optical fibers 152 may also be implemented.

In one aspect, the plurality of optical fibers 152 is situated within an outer ear canal to transmit and detect light in the ear canal. A light collimator 164, such as a prism, may be used to align a direction of the light emitted from the light source 120. One or more filters 160 may optionally be implemented to receive the reflected light 142 from the plurality of optical fibers 152b, 152c. However, the filters 160 may not be needed as the plurality of optical fibers 152b, 152c may be sufficient to filter ambient light and/or scattered light.

Embodiment—Operation of the Biosensor

One or more of the embodiments of the biosensor 100 described herein is configured to detect a concentration level or indicator of one or more substances within blood flow, such as analyte levels, nitric oxide levels, insulin resistance or insulin response after caloric intake and predict diabetic risk or diabetic precursors. The biosensor 100 may detect insulin response, vascular health, cardiovascular sensor, cytochrome P450 proteins (e.g. one or more liver enzymes or reactions), digestion phase 1 and 2 or caloric intake. The biosensor 100 may even be configured to detect proteins or other elements or compounds associated with cancer. The biosensor 100 may also detect various electrolytes and many common blood analytic levels, such as bilirubin amount and sodium and potassium. For example, the biosensor 100 may detect sodium NACL concentration levels in the arterial blood flow to determine dehydration. The biosensor 100 may also detect blood alcohol levels in vivo in the arterial blood flow. The biosensor 100 may also detect blood pressure, peripheral oxygen ($SpO_2$ or $SaO_2$) saturation, heart rate, respiration rate or other patient vitals. Because blood flow to the skin can be modulated by multiple other physiological systems, the PPG circuit 110 may also be used to monitor breathing, hypovolemia, and other circulatory conditions.

In use, the biosensor 100 performs PPG techniques using the PPG circuit 110 to detect the concentration levels of substances in blood flow. In one aspect, the biosensor 100 analyzes reflected visible or IR light to obtain a spectrum response such as, the resonance absorption peaks of the reflected visible, UV or IR light. The spectrum response includes spectral lines that illustrate an intensity or power or energy at a frequency or wavelength in a spectral region of the detected light.

The ratio of the resonance absorption peaks from two different frequencies can be calculated and based on the Beer-Lambert law used to obtain various levels of substances in the blood flow. First, the spectral response of a substance or substances in the arterial blood flow is determined in a controlled environment, so that an absorption coefficient $\alpha_{g1}$ can be obtained at a first light wavelength $\lambda 1$ and at a second wavelength $\lambda 2$. According to the Beer-Lambert law, light intensity will decrease logarithmically with path length l (such as through an artery of length l). Assuming then an initial intensity $I_{in}$ of light is passed through a path length l, a concentration $C_g$ of a substance may be determined using the following equations:

At the first wavelength $\lambda_1$, $I_1 = I_{in1} * 10^{-(\alpha_{g1}c_{gw} + \alpha_{w1}c_w)*l}$ At the first wavelength $\lambda_2$, $I_2 = I_{in2} * 10^{-(\alpha_{g2}c_{gw} + \alpha_{w2}c_w)*l}$ wherein:
$I_{in1}$ is the intensity of the initial light at $\lambda_1$
$I_{in2}$ is the intensity of the initial light at $\lambda_2$
$\alpha_{g1}$ is the absorption coefficient of the substance in arterial blood at $\lambda_1$
$\alpha_{g2}$ is the absorption coefficient of the substance in arterial blood at $\lambda_2$
$\alpha_{w1}$ is the absorption coefficient of arterial blood at $\lambda_1$
$\alpha_{w2}$ is the absorption coefficient of arterial blood at $\lambda_2$
$C_{gw}$ is the concentration of the substance and arterial blood
$C_w$ is the concentration of arterial blood
Then letting R equal:

$$R = \frac{\log 10\left(\frac{I1}{Iin1}\right)}{\log 10\left(\frac{I2}{Iin2}\right)}$$

The concentration of the substance Cg may then be equal to:

$$Cg = \frac{Cgw}{Cgw + Cw} = \frac{\alpha_{w2}R - \alpha_{w1}}{(\alpha_{w2} - \alpha_{gw2})*R - (\alpha_{w1} - \alpha_{gw1})}$$

The biosensor 100 may thus determine the concentration of various substances in arterial blood using spectroscopy at two different wavelengths using Beer-Lambert principles.

Figure 4:
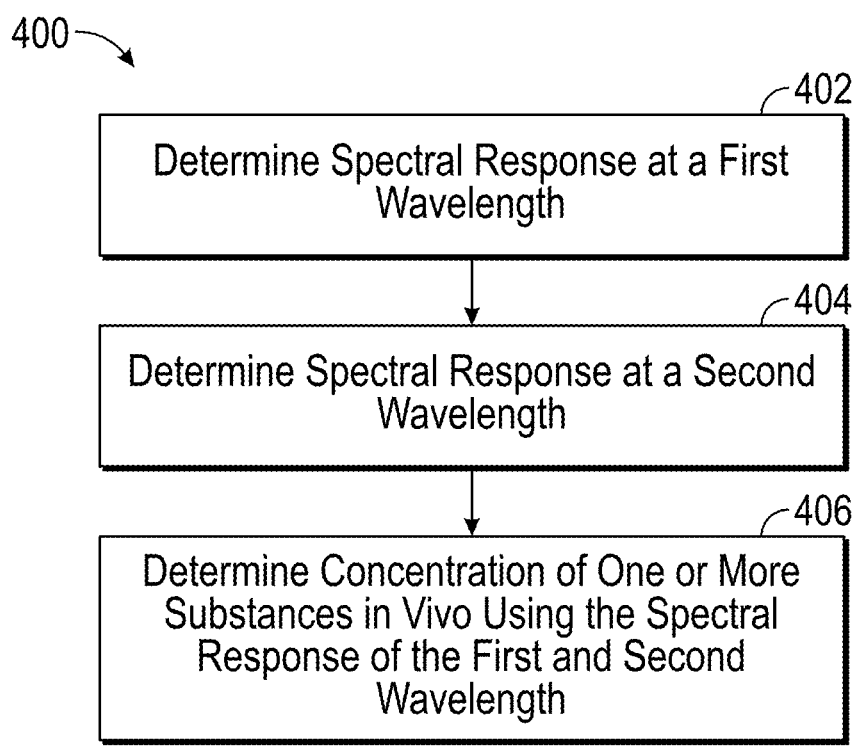
FIG. 4 illustrates a logical flow diagram of an embodiment of a method for determining concentration of one or more substances using Beer-Lambert principles.

FIG. 4 illustrates a logical flow diagram of an embodiment of a method 400 for determining concentration of one or more substances using Beer-Lambert principles. The biosensor 100 transmits light at least at a first predetermined wavelength in step 402 and at a second predetermined wavelength in step 404. The biosensor 100 detects the light (reflected from the skin or transmitted through the skin) and analyzes the spectral response at the first and second wavelengths to detect an indicator or concentration level of one or more substances in the arterial blood flow at 406. In general, the first predetermined wavelength is selected that has a high absorption coefficient for the targeted substance while the second predetermined wavelength is selected that has a low absorption coefficient for the targeted substance. Thus, it is generally desired that the spectral response for the first predetermined wavelength have a higher intensity level than the spectral response for the second predetermined wavelength.

In another aspect, the biosensor 100 may transmit light at the first predetermined wavelength at 402 and in a range of approximately 1 nm to 50 nm around the first predetermined wavelength. Similarly at 404, the biosensor 100 may transmit light at the second predetermined wavelength and in a range of approximately 1 nm to 50 nm around the second predetermined wavelength. The range of wavelengths is determined based on the spectral response since a spectral response may extend over a range of frequencies, not a single frequency (i.e., it has a nonzero linewidth). The light that is reflected or transmitted light by the target substance may by spread over a range of wavelengths rather than just the single predetermined wavelength. In addition, the center of the spectral response may be shifted from its nominal central wavelength or the predetermined wavelength. The range of 1 nm to 50 nm is based on the bandwidth of the spectral response line and should include wavelengths with increased light intensity detected for the targeted substance around the predetermined wavelength.

The first spectral response of the light over the first range of wavelengths including the first predetermined wavelength and the second spectral response of the light over the second range of wavelengths including the second predetermined wavelengths is then generated. The biosensor 100 analyzes the first and second spectral responses to detect an indicator or concentration level of one or more substances in the arterial blood flow at 406.

Figure 5A:
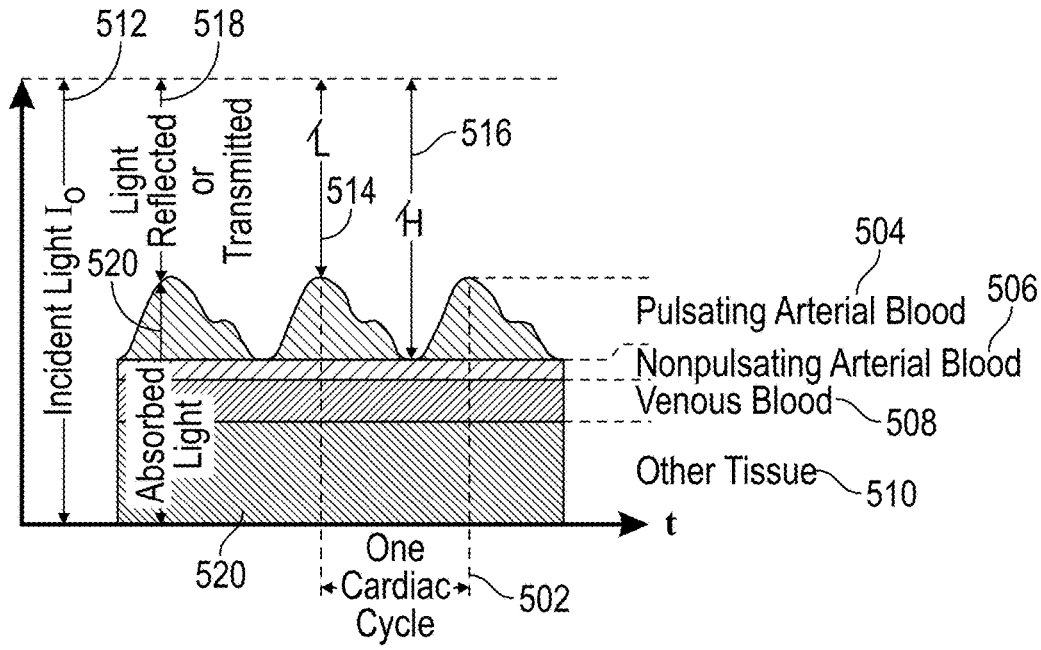
FIG. 5A illustrates a schematic block diagram of an embodiment of a method for photoplethysmography (PPG) techniques.
Figure 5B:
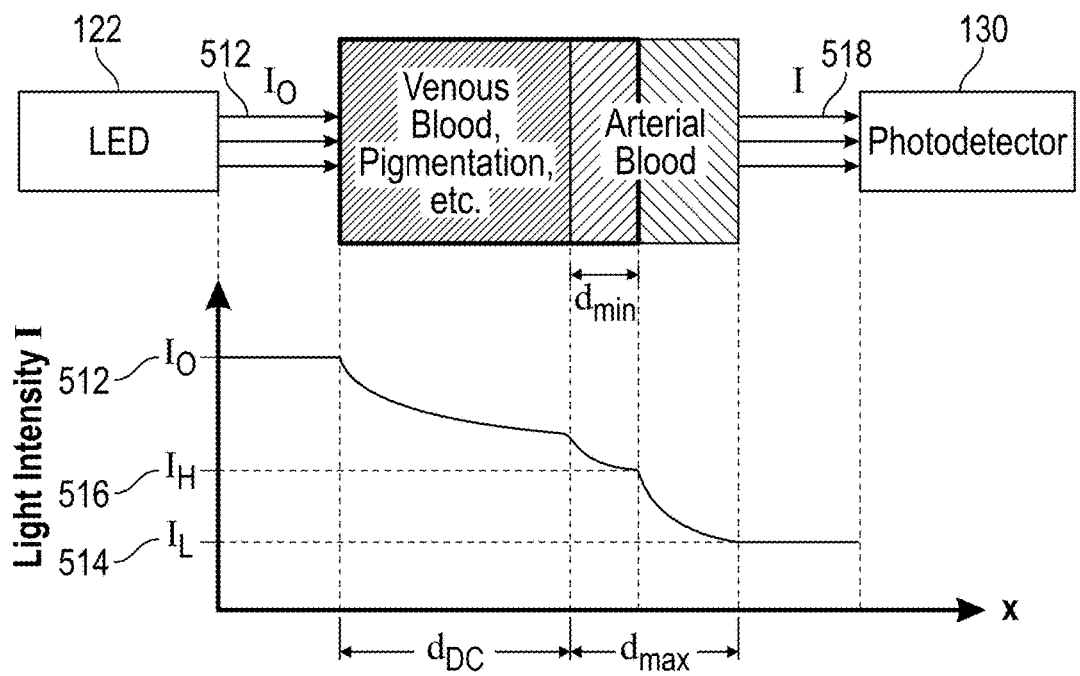
FIG. 5B illustrates another schematic block diagram of an embodiment of a method for photoplethysmography (PPG) techniques.

FIG. 5A and FIG. 5B illustrate schematic block diagrams of an embodiment of a method for photoplethysmography (PPG) techniques. Photoplethysmography (PPG) is used to measure time-dependent volumetric properties of blood in blood vessels due to the cardiac cycle. For example, the heartbeat affects volume of arterial blood flow and the concentration of absorption levels being measured in the arterial blood flow. As shown in FIG. 5A, over a cardiac cycle 502, pulsating arterial blood 504 changes the volume of blood flow in an artery.

Incident light $I_O$ 512 is directed at a tissue site and a certain amount of light is reflected or transmitted 518 and a certain amount of light is absorbed 520. At a peak of arterial blood flow or arterial volume, the reflected/transmitted light $I_L$ 514 is at a minimum due to absorption by the venous blood 508, nonpulsating arterial blood 506, pulsating arterial blood 504, other tissue 510, etc. At a minimum of arterial blood flow or arterial volume during the cardiac cycle, the transmitted/reflected light $I_H$ 516 is at a maximum due to lack of absorption from the pulsating arterial blood 504.

The biosensor 100 is configured to filter the reflected/transmitted light $I_L$ 514 of the pulsating arterial blood 504 from the transmitted/reflected light $I_H$ 516. This filtering isolates the light due to reflection/transmission of substances in the pulsating arterial blood 504 from the light due to reflection/transmission from venous (or capillary) blood 508, other tissues 510, etc. The biosensor 100 may then measure the concentration levels of one or more substances from the reflected/transmitted light $I_L$ 514 in the pulsating arterial blood 504.

For example, as shown in FIG. 5B, incident light $I_O$ 512 is directed at a tissue site by an LED 122 at one or more wavelengths. The reflected/transmitted light $I_H$ 518 is detected by photodetector 130. At a peak of arterial blood flow or arterial volume, the reflected light $I_L$ 514 is at a minimum due to absorption by venous blood 508, nonpulsating arterial blood 506, pulsating arterial blood 504, other tissue 510, etc. At a minimum of arterial blood flow or arterial volume during the cardiac cycle, the Incident or reflected light $I_H$ 516 is at a maximum due to lack of absorption from the pulsating arterial blood 504. Since the light I 518 is reflected or traverses through a different volume of blood at the two measurement times, the measurement provided by a PPG circuit 110 is said to be a 'volumetric measurement' descriptive of the differential volumes of blood present at a certain location within the patient's arteriolar bed at different times. Though the above has been described with respect to arterial blood flow, the same principles described herein may be applied to venous blood flow.

In general, the relative magnitudes of the AC and DC contributions to the reflected/transmitted light signal I 518 may be used to substantially determine the differences between the diastolic time and the systolic points. In this case, the difference between the reflected light $I_L$ 514 and reflected light $I_H$ 516 corresponds to the AC contribution of the reflected light 518 (e.g. due to the pulsating arterial blood flow). A difference function may thus be computed to determine the relative magnitudes of the AC and DC components of the reflected light I 518 to determine the magnitude of the reflected light $I_L$ 514 due to the pulsating arterial blood 504. The described techniques herein for determining the relative magnitudes of the AC and DC contributions is not intended as limiting. It will be appreciated that other methods may be employed to isolate or otherwise determine the relative magnitude of the light $I_L$ 514 due to pulsating arterial blood flow.

Figure 6:
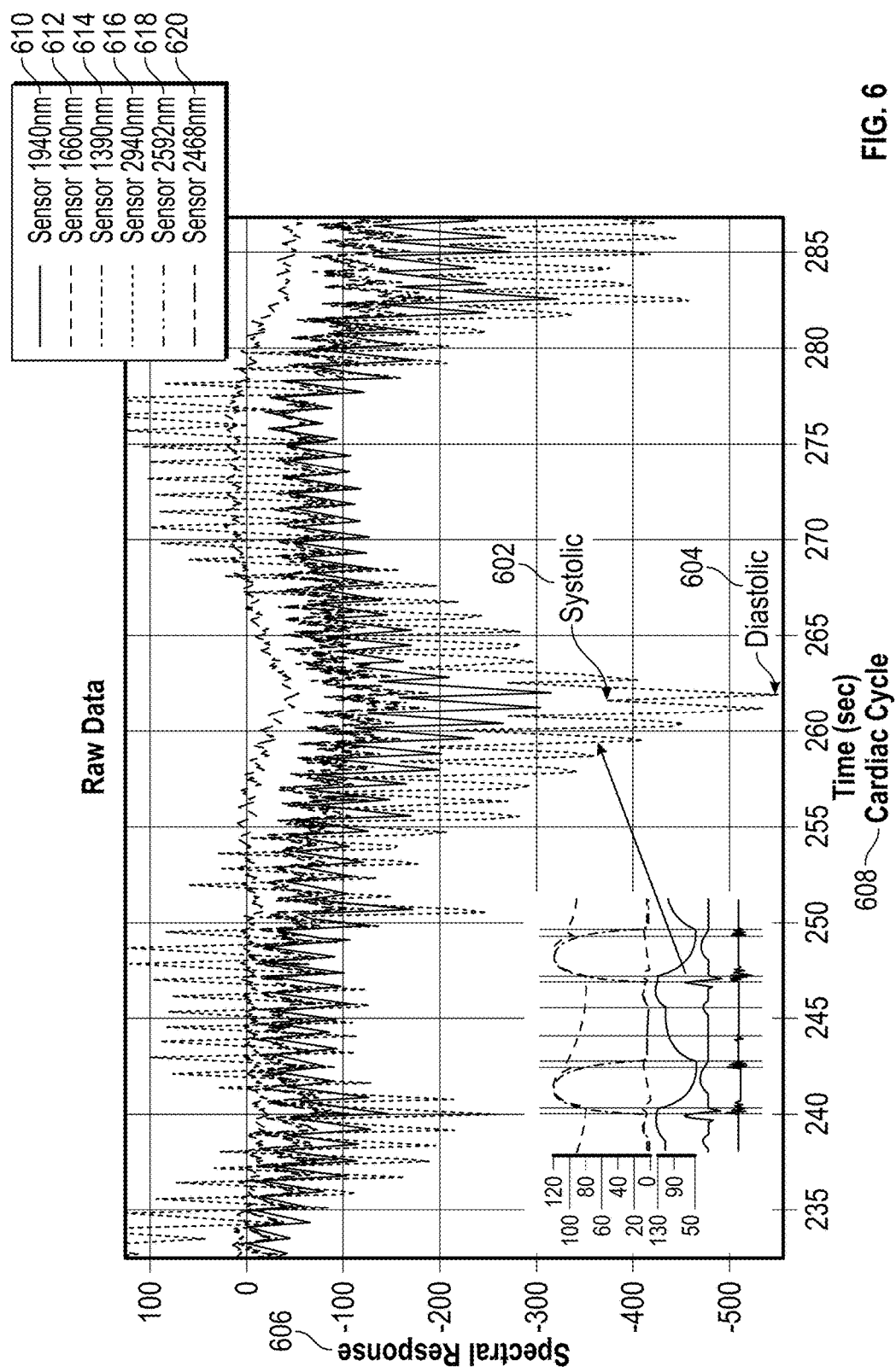
FIG. 6 illustrates a schematic diagram of a graph of actual clinical data obtained using PPG techniques at a plurality of wavelengths.

FIG. 6 illustrates a schematic diagram of a graph of actual clinical data obtained using PPG techniques at a plurality of wavelengths. The biosensor 100 emits light having a plurality of wavelengths during a measurement period. The light at each wavelength (or range of wavelengths) may be transmitted concurrently or sequentially. The intensity of the reflected light at each of the wavelengths (or range of wavelengths) is detected and the spectral response is measured over the measurement period. The spectral response 606 for the plurality of wavelengths obtained using the biosensor in clinical trials is shown in FIG. 6. In this clinical trial, two biosensors 100 attached to two separate fingertips of a patient were used to obtain the plurality of spectral responses 606. The first biosensor 100 obtained the spectral responses for a wavelength at 940 nm 610, a wavelength at 660 nm 612 and a wavelength at 390 nm 614. The second biosensor 100 obtained the spectral responses for a wavelength at 940 nm 616, a wavelength at 592 nm 618 and a wavelength at 468 nm 620.

In one aspect, the spectral response of each wavelength may be aligned based on the systolic 602 and diastolic 604 points in their spectral responses. This alignment is useful to associate each spectral response with a particular stage or phase of the pulse-induced local pressure wave within the blood vessel (which may mimic the cardiac cycle 608 and thus include systolic and diastolic stages and sub-stages thereof). This temporal alignment helps to determine the absorption measurements acquired near a systolic point in time of the cardiac cycle 608 and near the diastolic point in time of the cardiac cycle 608 associated with the local pressure wave within the patient's blood vessels. This measured local pulse timing information may be useful for properly interpreting the absorption measurements in order to determine the relative contributions of the AC and DC components measured by the biosensor 100. So for one or more wavelengths, the systolic points 602 and diastolic points 604 in the spectral response are determined. These systolic points 602 and diastolic points 604 for the one or more wavelengths may then be aligned as a method to discern concurrent responses across the one or more wavelengths.

In another embodiment, the systolic points 602 and diastolic points 604 in the absorbance measurements are temporally correlated to the pulse-driven pressure wave within the arterial blood vessels—which may differ from the cardiac cycle. In another embodiment, the biosensor 100 may concurrently measure the intensity reflected at each the plurality of wavelengths. Since the measurements are concurrent, no alignment of the spectral responses of the plurality of wavelengths may be necessary. FIG. 6 illustrates the spectral response of the plurality of wavelengths with the systolic points 602 and diastolic points 604 aligned.

Figure 7:
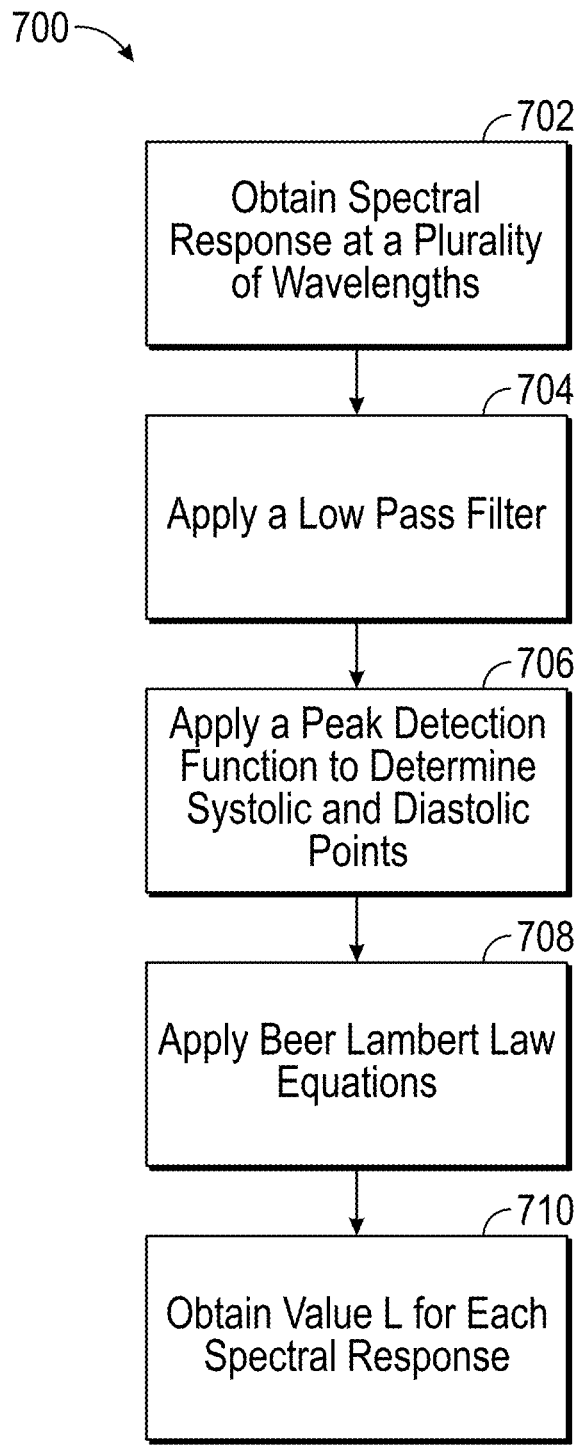
FIG. 7 illustrates a logical flow diagram of an embodiment of a method of the biosensor.

FIG. 7 illustrates a logical flow diagram of an embodiment of a method 700 of the biosensor 100. In one aspect, the biosensor 100 emits and detects light at a plurality of predetermined frequencies or wavelengths, such as approximately 940 nm, 660 nm, 390 nm, 592 nm, and 468 nm. The light is pulsed for a predetermined period of time (such as 100 usec or 200 Hz) sequentially at each predetermined wavelength. In another aspect, light may be pulsed in a wavelength range of 1 nm to 50 nm around each of the predetermined wavelengths. Then, the spectral responses are obtained for the plurality of wavelengths at 702. The spectral response may be measured over a predetermined period (such as 300 usec.). This measurement process is repeated sequentially pulsing the light and obtaining spectral measurements over a desired measurement period, e.g. from 1-2 seconds to 1-2 minutes or 2-3 hours or continuously over days or weeks. Because the human pulse is typically on the order of magnitude of one 1 HZ, typically the time differences between the systolic and diastolic points are on the order of magnitude of milliseconds or tens of milliseconds or hundreds of milliseconds. Thus, spectral response measurements may be obtained at a frequency of around 10-100 Hz over the desired measurement period.

A low pass filter (such as a 5 Hz low pass filter) is applied to the spectral response signal at 704. The relative contributions of the AC and DC components are obtained $T_{AC+DC}$ and $I_{AC}$. A peak detection algorithm is applied to determine the systolic and diastolic points at 706. Beer Lambert equations are applied as described below at 708. For example, the $L_\lambda$ values are then calculated for one or more of the wavelengths λ, wherein the $L_\lambda$ values for a wavelength equals:

$$L\lambda = \text{Log}10\left(\frac{IAC + DC}{IDC}\right)$$

wherein $I_{AC+DC}$ is the intensity of the detected light with AC and DC components and $I_{DC}$ is the intensity of the detected light with the AC filtered by the low pass filter. The value $L_\lambda$ isolates the spectral response due to pulsating arterial blood flow, e.g. the AC component of the spectral response.

A ratio R of the $L_\lambda$ values at two wavelengths may then be determined. For example, $$\text{Ratio } R = \frac{L\lambda1}{L\lambda2}$$

The $L_\lambda$ values and Ratio R may be determined for one or more of the predetermined measurement periods over a desired time period, e.g. from 1-2 seconds to 1-2 minutes or 2-3 hours or continuously over days or weeks to monitor the values.

Embodiment—Determination of Concentration Levels of One or More Substances in Blood Flow In one aspect, based on unexpected results from clinical trials, it was determined that a ratio $R_{390,940}$ obtained at approximately $L_{\lambda 1}$=390 nm and $L_2$=940 is useful as a predictor or indicator of diabetic risk or diabetes. For example, during experimental clinical trials, spectral responses were obtained during predetermined measurement periods over a 1-2 minute time period at 390 nm and 940 nm. An $R_{390,940}$ value was obtained based on the spectral responses measured during a plurality of the predetermined measurement periods over the 1-2 minute time period. From the unexpected results of the clinical trials, an average or mean $R_{390,940}$ value of less than 1 (e.g., approximately 0.5) indicated that a person has diabetes or early onset of diabetes. An average or mean $R_{390,940}$ value of 2 or above indicated that a person has a lower risk of a diabetes diagnosis. An average or mean $R_{390,940}$ value in the 5-6 range indicated no current risk of diabetes. The $R_{390,940}$ value determined using $L_{\lambda 1}=390$ nm and $L_2=940$ was thus an indicator of diabetic risk and diabetes. Thus, based on the clinical trials, a non-invasive, quick 1-2 minute test produced an indicator of diabetes or diabetic risk in a person.

The $R_{390,940}$ value with $L_{\lambda 1=390nm}$ and $L_{\lambda 2=940}$ may be non-invasively and quickly and easily obtained using the biosensor 100 in a physician's office or other clinical setting or at home. In one aspect, the $R_{390,940}$ value may be used to determine whether further testing for diabetes needs to be performed. For example, upon detection of a low $R_{390,940}$ value, a clinician may then determine to perform further testing and monitoring, e.g. using glucose ingestion tests over a longer period of time or using the biosensor 100 over a longer period of time or other type of testing.

In particular, in unexpected results, it is believed that nitric oxide NO levels in the arterial blood flow is being measured at least in part by the biosensor 100 at $\lambda 1=390$ nm. Since NO is partly in a gaseous form in blood vessels (prior to adhesion to hemoglobin), the total NO concentration levels of in vitro blood samples, e.g. from a finger prick, are not detected as the gas dissipates. Thus, the biosensor 100 measurements to determine the $L_{390\ nm}$ values are the first time NO concentration levels in arterial blood flow have been measured directly in vivo. In clinical trials performed as described further herein, in unexpected results, it seems that the NO levels are an indication of insulin response in the blood as well as concentration levels of insulin and/or glucose levels in the blood. The $L_{\lambda 1=390\ nm}$ and R value obtained from $L_{\lambda 1=390\ nm}$ are thus an indicator of blood glucose levels, insulin response and diabetic risk as well as vascular health. These unexpected results have advantages in early detection of diabetic risk and easier, non-invasive monitoring of insulin resistance and glucose levels as well as vascular health and other conditions. These results are discussed in more detail herein with illustrative experimental data.

The biosensor 100 may also function as a pulse oximeter using similar principles under Beer-lambert law to determine pulse and oxygen saturation levels in pulsating arterial flow. For example, a first wavelength at approximately 940 nm and a second wavelength at approximately 660 nm may be used to determine oxygen saturation levels.

The biosensor 100 may also be used to determine alcohol levels in the blood using wavelengths at approximately 390 nm and/or 468 nm. In another embodiment, an $R_{46}$ for at least $L_{468\ nm}/L_{940\ nm}$ may be used as a liver enzyme indicator, e.g. P450 enzyme indicator. In another embodiment, an $R_{592,940}$ value for at least $L_{592\ nm}/L_{940\ nm}$ may be used as a digestive indicator to measure digestive responses, such as phase 1 and phase 2 digestive stages. The biosensor 100 may also detect other types of electrolytes or analytes, such as sodium and potassium, using similar PPG techniques. In another aspect, the biosensor 100 may detect which blood cell counts or concentration levels in arterial blood flow using similar PPG techniques.

In another aspect, abnormal cells or proteins or compounds that are present or have higher concentrations in the blood with persons having cancer, may be detected using similar PPG techniques described herein at one or more other wavelengths. Thus, cancer risk may then be obtained through non-invasive testing by the biosensor 100. Since the biosensor 100 may operate in multiple frequencies, various health monitoring tests may be performed concurrently. These and other aspects of the biosensor 100 are described in more detail herein with clinical trial results.

Figure 8:
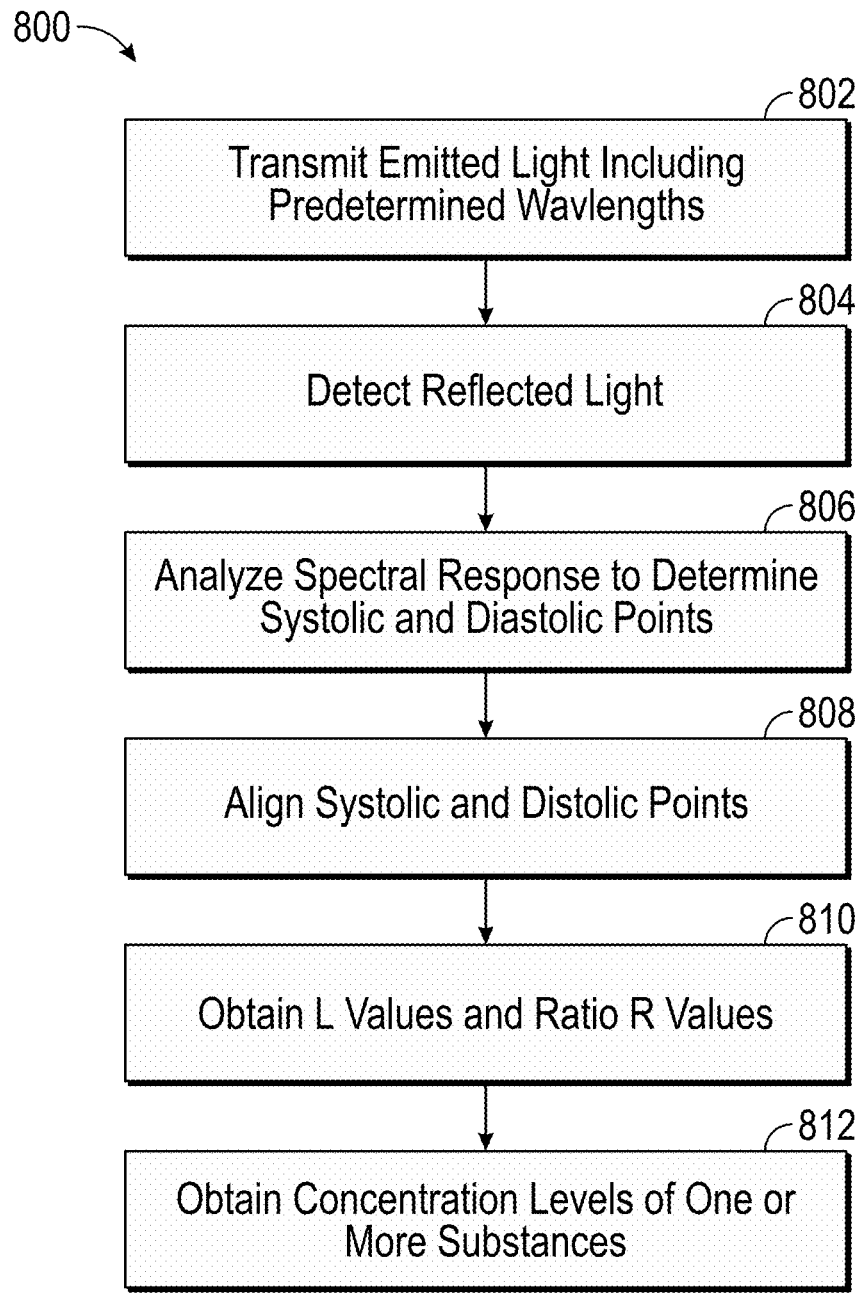
FIG. 8 illustrates a logical flow diagram of an embodiment of a method of determining concentration levels of one or more substances.

FIG. 8 illustrates a logical flow diagram of an embodiment of a method 800 of determining concentration levels of one or more substances. The biosensor 100 transmits light at one or more predetermined wavelengths. In another aspect, the biosensor 100 may also transmit light at one or more ranges of approximately 1 nm to 50 nm wavelengths, each range including one or more predetermined wavelengths. For example, for the predetermined wavelength 390 nm, the biosensor 100 may transmit light directed at skin tissue of the patient in a range of 360 nm to 410 nm including the predetermine wavelength 390 nm. For the predetermined wavelength of 940 nm, the biosensor 100 may transmit light directed at the skin tissue of the patient in a range of 920 nm to 975 nm.

The biosensor 100 detects the reflected light at 804 from the skin tissue and analyzes a spectral response at the one or more predetermined wavelengths (or ranges including the predetermined wavelengths) at 806. The absorption levels are measured over one or more cardiac cycles and systolic and diastolic points of the spectral response are determined. Because the human pulse is typically on the order of magnitude of one 1 HZ, typically the time differences between the systolic and diastolic points are on the order of magnitude of milliseconds or tens of milliseconds or hundreds of milliseconds. Thus, spectral response measurements may need to be acquired at a frequency of around 10-100 Hz.

The systolic and diastolic points of the spectral response for a wavelength may also be aligned with systolic and diastolic points of another wavelength, an arterial pulse waveform or cardiac cycle at 808. The biosensor 100 is then configured to calculate $L_{\lambda 1}$ and $L_{\lambda 2}$ values at 810. The biosensor 100 may also calculate ratio $R_{\lambda 1,\lambda 2}$ values at 810. Using the determined $L_{\lambda 1}$ and $L_{\lambda 2}$ values or ratio $R_{\lambda 1,\lambda 2}$ value, concentration levels or indicators of one or more substances may be obtained in the pulsating arterial blood flow at 812. The biosensor 100 may thus be used to non-invasively detect concentration levels or indicators of one or more substances in pulsating arterial blood flow.

Figure 9:
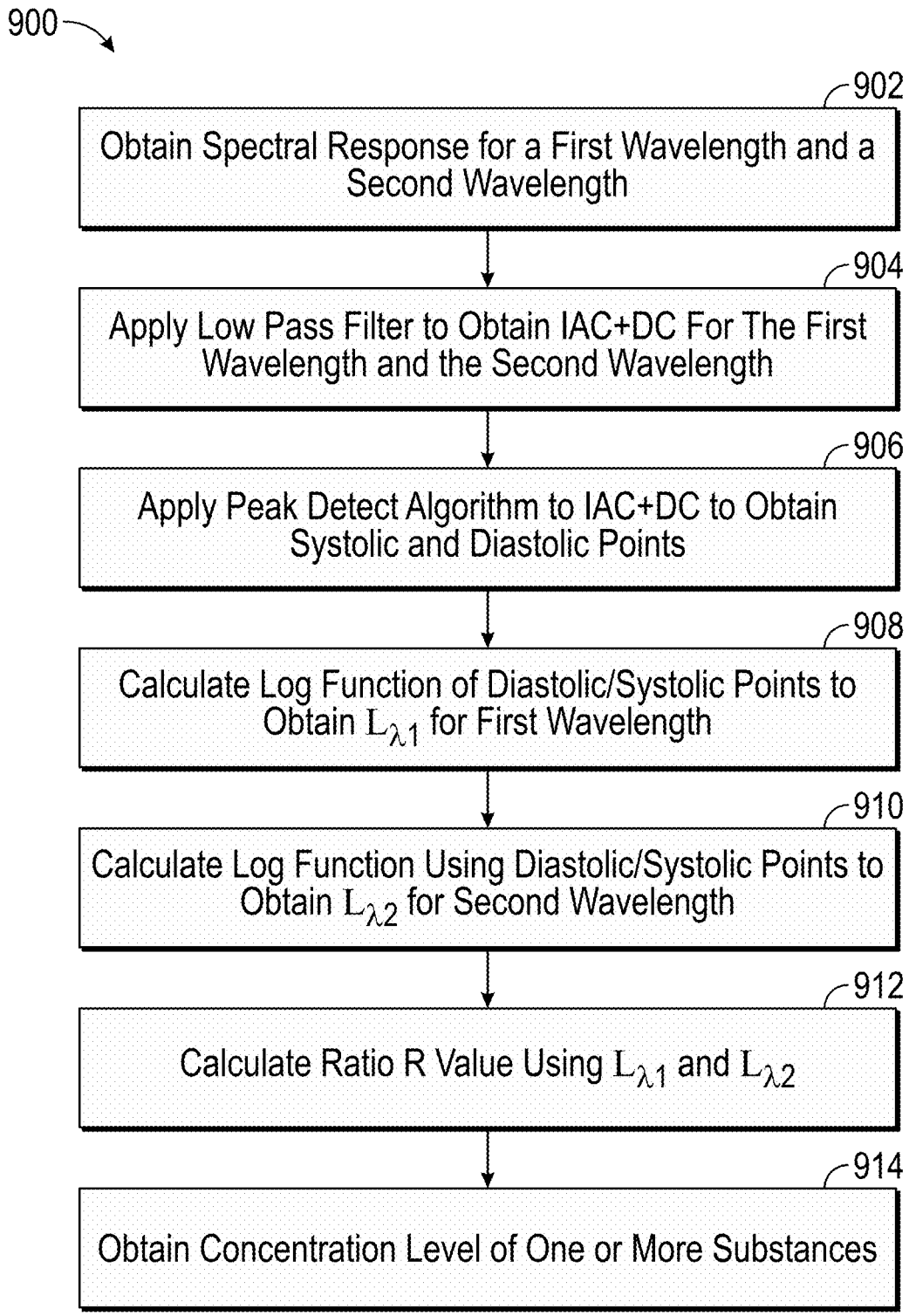
FIG. 9 illustrates a logical flow diagram of another embodiment of a method of determining concentration levels of one or more substances.

FIG. 9 illustrates a logical flow diagram of another embodiment of a method 900 of determining concentration levels of one or more substances. The biosensor 100 obtains a first spectral response signal including a first wavelength and a second response signal including a second wavelength at 902. In general, the first wavelength is selected that has a high absorption coefficient for the targeted substance while the second wavelength is selected that has a low absorption coefficient for the targeted substance. Thus, it is generally desired that the spectral response for the first predetermined wavelength have a higher intensity level than the spectral response for the second predetermined wavelength.

Each of the spectral response signals includes AC and DC components $I_{AC+DC}$. A low pass filter is applied to the spectral response signals $I_{AC+DC}$ to isolate the DC component of the first and second spectral response signals $I_{DC}$.

The AC fluctuation is due to the pulsatile expansion of the arteriolar bed due to the volume increase in arterial blood. In order to measure the AC fluctuation, measurements are taken at different times and a peak detection algorithm or other means is used to determine the diastolic point and the systolic point of the spectral response at 906. The systolic and diastolic measurements are compared in order to compute the aforementioned R ratio. For example, a logarithmic function may be applied to the ratio of $I_{AC+DC}$ and $I_{DC}$ to obtain an L value for the first wavelength $L_{\lambda 1}$ at 908 and for the second wavelength $L_{\lambda 2}$ at 910. The ratio R of the $L_\lambda$ values may then be calculated at 912.

Figure 10:
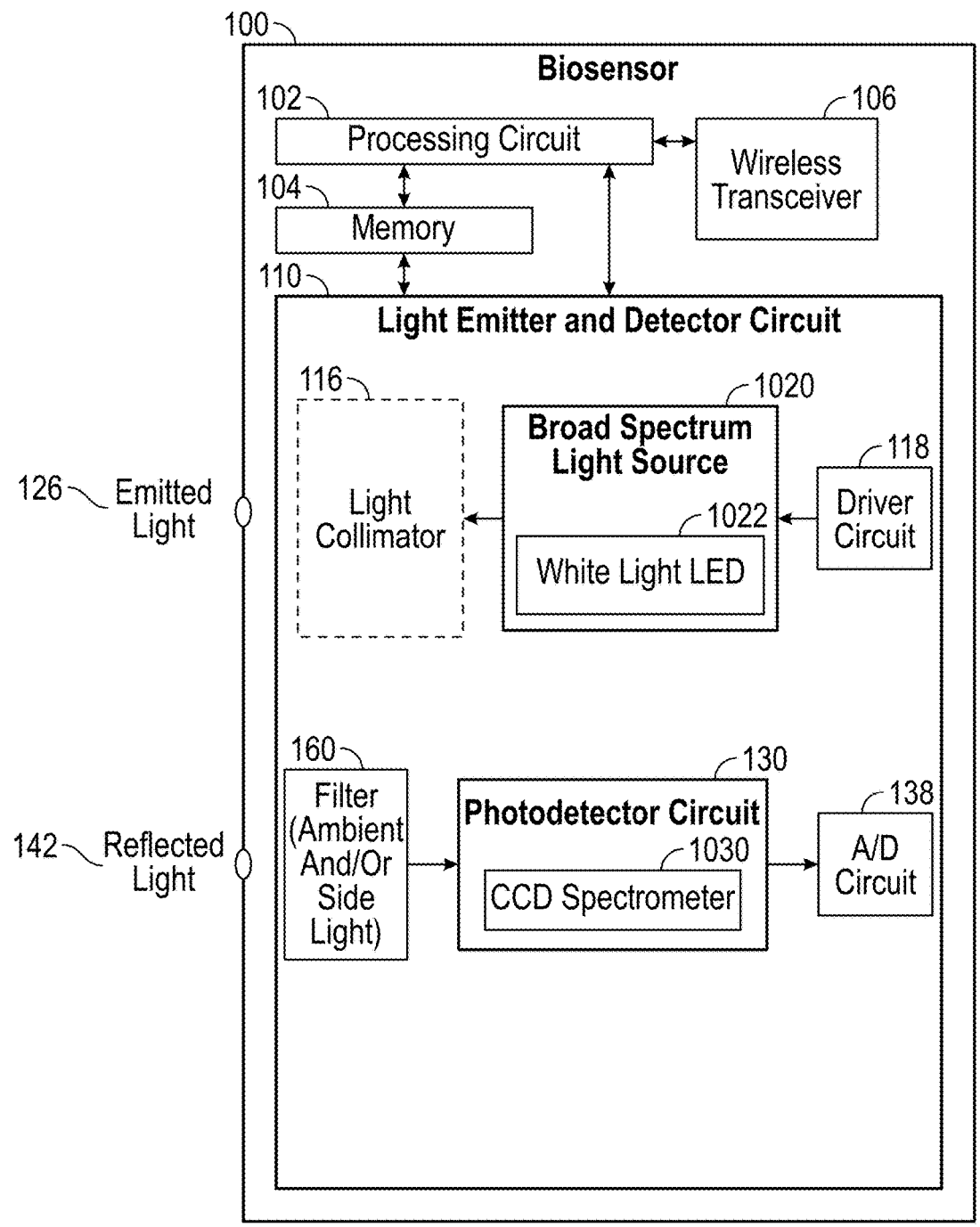
FIG. 10 illustrates a schematic block diagram of another embodiment of a biosensor using a broad spectrum light source.

FIG. 10 illustrates a schematic block diagram of another embodiment of a biosensor 100 using a broad spectrum light source 1020. In one aspect, the biosensor 100 may include a broad spectrum light source 1020, such as a white light to infrared (IR) or near IR LED 1022, that emits light with wavelengths from e.g. 350 nm to 2500 nm. Broad spectrum light sources with different ranges may be implemented. In an aspect, a broad spectrum light source with a range across 100 nm wavelengths to 2000 nm range of wavelengths in the visible, IR and/or UV frequencies. For example, a broadband tungsten light source for spectroscopy may be used. The spectral response of the reflected light is then measured across the wavelengths in the broad spectrum, e.g. from 350 nm to 2500 nm, concurrently. In an aspect, a charge coupled device (CCD) spectrometer 1030 may be configured to measure the spectral response of the detected light over the broad spectrum.

The spectral response of the reflected light is analyzed for a plurality of wavelengths, e.g. at 10 nm to 15 nm to 20 nm, incremental wavelengths across the wavelengths from 10 nm to 2500 nm. For example, the processing described with respect to FIG. 9 is performed at the plurality of wavelengths. In one aspect, the L values are calculated at incremental wavelengths, such as at 1 nm or 1.5 nm or 2 nm incremental wavelengths. This process may be used to determine one or more wavelengths or ranges of wavelengths useful in detection for one or more substances in the arterial blood flow. For example, a spectral response around a wavelength of 500 nm may have a higher intensity. Trials may then be conducted to determine the one or more substances in the blood that generates this spectral response. In another embodiment, a known substance may be present in the blood and the spectral response across the broad spectrum is then analyzed to determine a pattern or correlation of intensities of wavelengths in the spectral response to the known substance. For example, a pattern of intensities of wavelengths across a range of wavelengths may indicate the presence of a substance. The intensities of the wavelengths may then be analyzed to determine concentration levels of the substance as described in more detail herein.

In another embodiment, the spectral response is analyzed at a set of predetermined wavelengths (or a range of 1 nm to 50 nm including each predetermined wavelength). The L values are calculated for the set of predetermined wavelengths using the analyzed spectral responses. The concentration levels of one or more substances may then be determined based on absorption coefficients for the one or more substances at each of the predetermined wavelengths. The concentration levels of a plurality of substances may be determined using the spectral response of a plurality of frequencies. The biosensor 100 may thus be used to detect a plurality of substances based on data obtained during a single measurement period. The biosensor 100 may thus perform a blood panel analysis based on in vivo arterial blood flow in a relatively short measurement period of 1-5 minutes. The blood panel analysis may be performed in a physician's office to determine results of the test while the patient is in the office. The biosensor 100 may thus provide blood panel analysis results in a 1-5 minute measurement period without a need for blood samples and lab tests that may take hours or days or weeks to obtain.

Figure 11A:
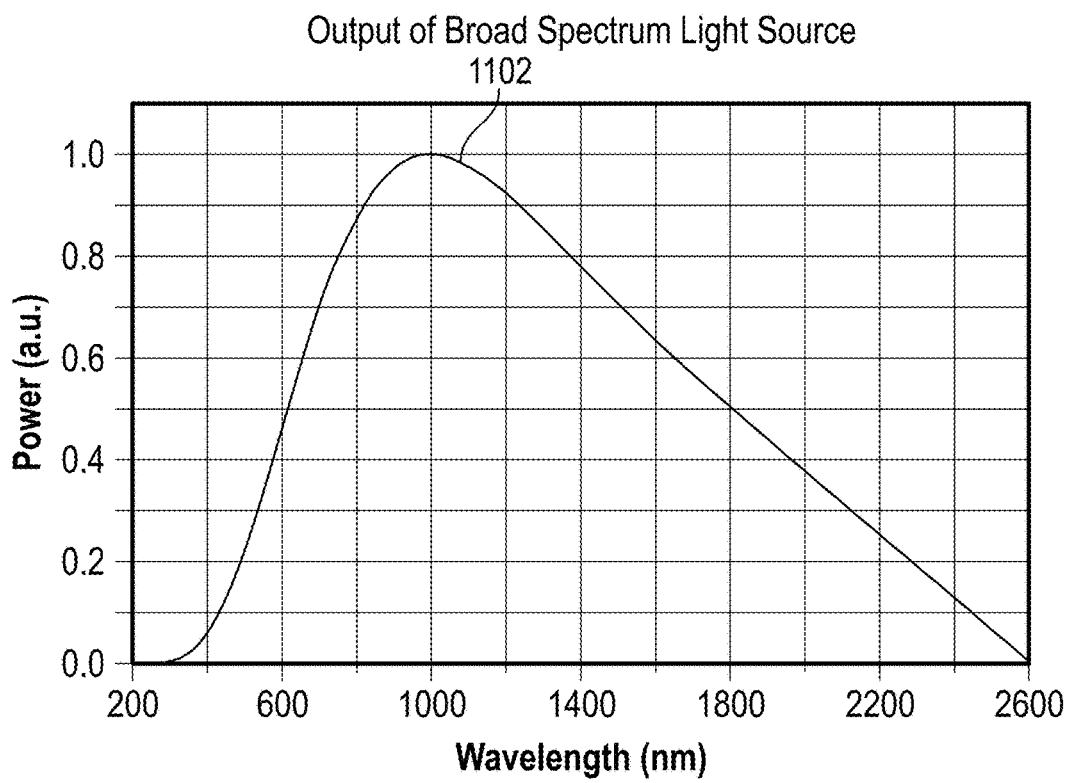
FIG. 11A illustrates a graph of an embodiment of an output of a broad spectrum light source.

FIG. 11A illustrates a graph of an embodiment of an output of a broad spectrum light source. The relative light intensity or power output of the broad spectrum light source is shown versus wavelength of the output light Io. The light intensity or power of the output light extends from wavelengths of approximately 350 nm to approximately 2500 nm. The broad spectrum light source 1020 emits light with power across the wavelengths from 350 nm to 2500 nm. Broad spectrum light sources with different ranges may be implemented. In an aspect, a broad spectrum light source with a range across 100 nm wavelengths to 2000 nm range of wavelengths in the visible, IR and/or UV frequencies.

Figure 11B:
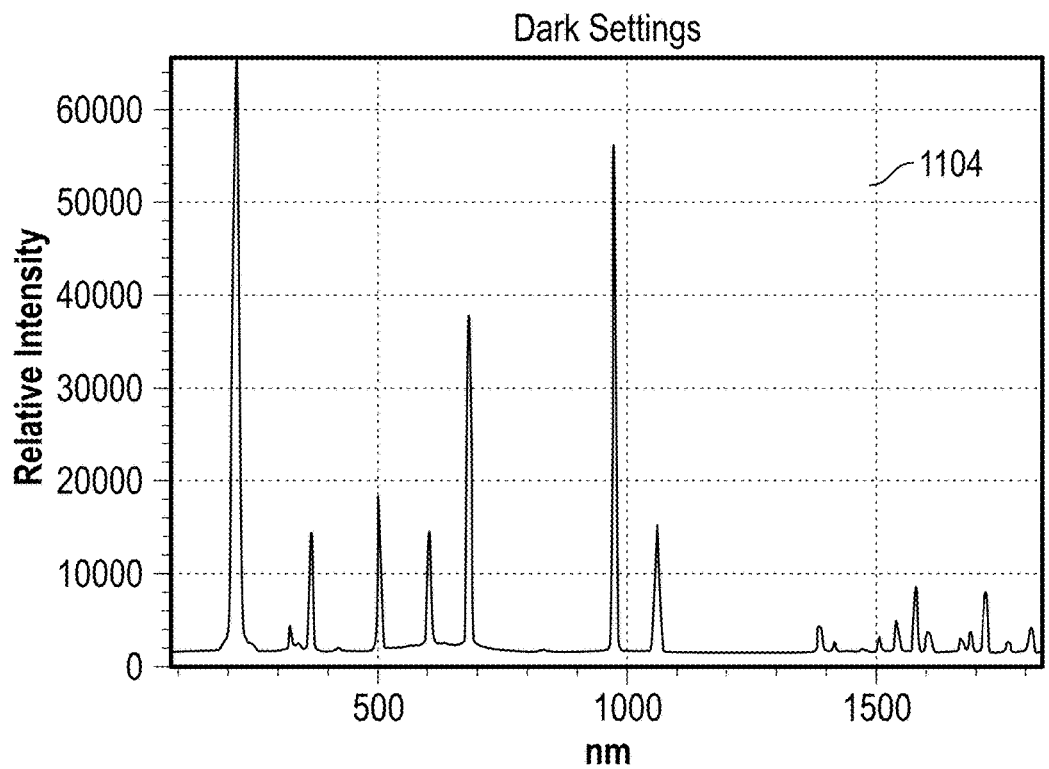
FIG. 11B illustrates a graph with an embodiment of an exemplary spectral response of detected light across a broad spectrum.

FIG. 11B illustrates a graph with an embodiment of an exemplary spectral response of detected light 1104 across a broad spectrum, e.g. from approximately 10 nm to 2000 nm. In one aspect, the spectral response of the detected light 1104 may be analyzed at a plurality of wavelengths, e.g. at a set of predetermined wavelengths or at incremental wavelengths. In another aspect, the spectral response of wavelengths with a detected intensity or power exceeding a predetermined threshold may be analyzed. For example, in the graph shown in FIG. 11B, the spectral response at wavelengths of 200 nm, 680 nm and 990 nm (and ranges of +/−20 to 50 nm around these wavelengths) exceeding a relative intensity threshold of 20000 may be analyzed.

Figure 12:
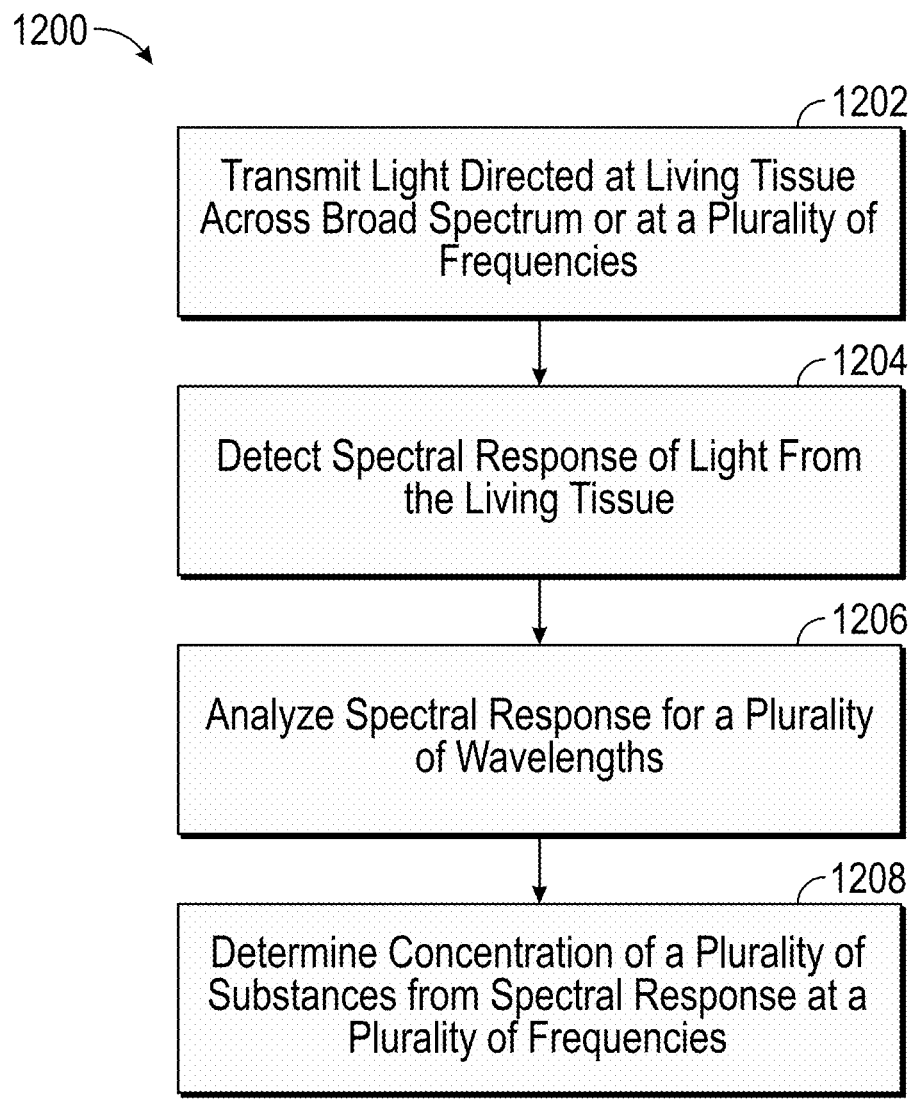
FIG. 12 illustrates a logical flow diagram of an exemplary method to determine blood concentration levels of a plurality of substances using the spectral response for a plurality of wavelengths.

FIG. 12 illustrates a logical flow diagram of an exemplary method 1200 to determine blood concentration levels of a plurality of substances using the spectral response for a plurality of wavelengths. The biosensor 100 transmits light directed at living tissue. The light may be across a broad spectrum or at a plurality of discrete frequencies or at a single frequency. For example, the light may be emitted using a broad spectrum light source or multiple LEDs transmitting at discrete wavelengths or a tunable laser transmitting at one or more frequencies. The spectral response of light (e.g. either transmitted through the living tissue or reflected by the living tissue) is detected at 1204. The spectral response is analyzed at a plurality of wavelengths (and ranges of +/−20 to 50 nm around these wavelengths) at 1206. In one aspect, the systolic and diastolic points are determined at the plurality of wavelengths and the L values are calculated using the systolic and diastolic points. In one aspect, the L values are determined at incremental wavelengths, such as at 1 nm or 1.5 nm or 2 nm incremental wavelengths. In another aspect, the L values are calculated for a set of predetermined wavelengths. A ratio R value may also be determined using L values derived from a first spectral response obtained for a first wavelength (and in one aspect including a range of +/−20 to 50 nm) and a spectral response obtained for a second wavelength (and in one aspect including a ranges of +/−20 to 50 nm).

Using the absorption coefficients associated with the plurality of substances, the concentration levels of a plurality of substances may then be determined. For example, the intensity of light may be due to absorption by a plurality of substances in the arterial blood flow. For example, $$LN(I_{1-n}) = \mu_1 * C_1 + \mu_2 * C_2 + \mu_3 * C_3 \ldots + \mu_n * C_n$$

wherein, $I_{1-n}$=intensity of light at wavelengths $\lambda_{1-n}$ $\mu_n$=absorption coefficient of substance 1, 2, . . . n at wavelengths $\lambda_{1-n}$ $C_n$=Concentration level of substance 1, 2, . . . n When the absorption coefficients $\mu_{1-n}$ are known at the wavelengths $\lambda_{1-n}$, then the concentration levels $C_{1-n}$ of multiple substances may be determined.

Figure 13:
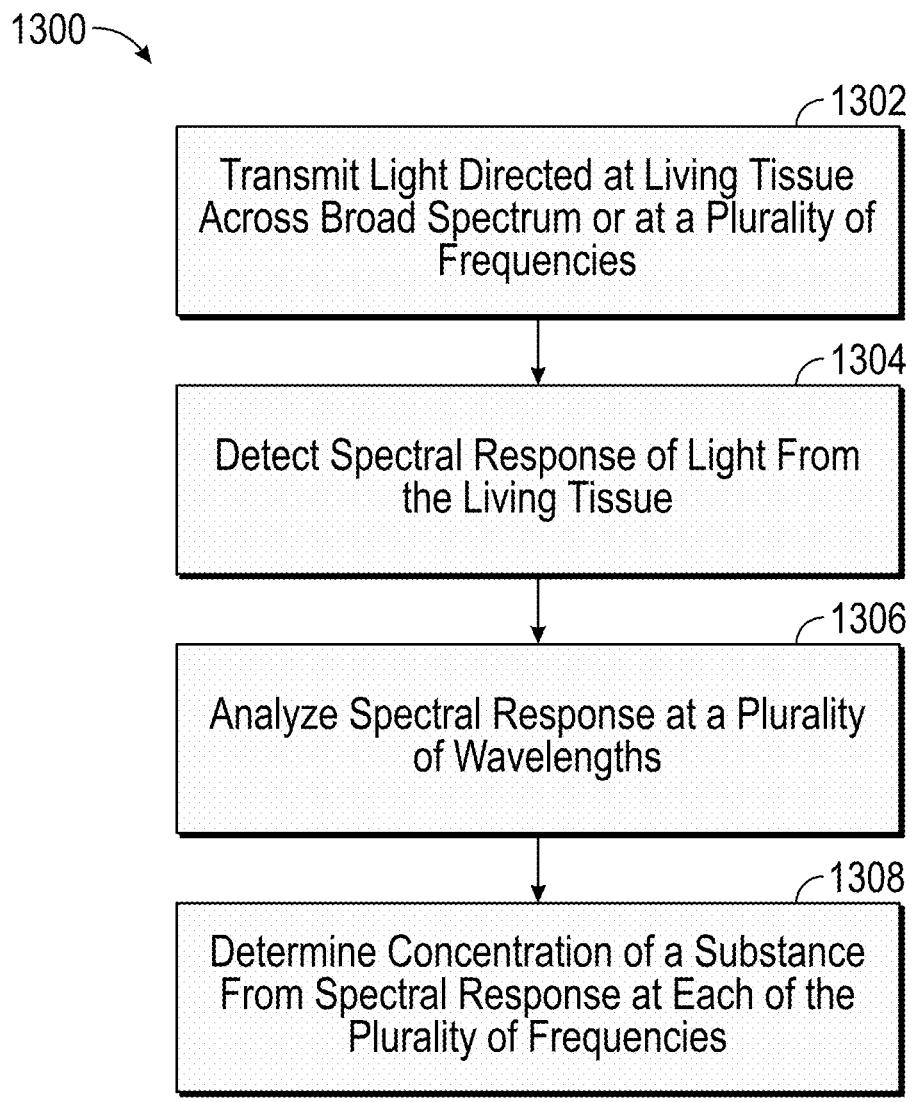
FIG. 13 illustrates a logical flow diagram of an exemplary method to determine blood concentration levels of a single substance using the spectral response for a plurality of wavelengths.

FIG. 13 illustrates a logical flow diagram of an exemplary method 1300 to determine blood concentration levels of a single substance using the spectral response for a plurality of wavelengths. The intensity of light at a plurality of wavelengths may be due to absorption by a single substance in the arterial blood flow. For example, a single substance may absorb or reflect a plurality of different wavelengths of light. In this example then, $$LN(I_{1-n})=\mu_1*C+\mu_2*C+\mu_3*C \ldots +\mu_n*C$$

wherein, $I_{1-n}$=intensity of light at wavelengths $\lambda_{1-n}$ $\mu_n$=absorption coefficient of a substance at wavelengths $\lambda_{1-n}$ C=Concentration level of a substance When the absorption coefficients $\mu_{1-n}$ of the single substance are known at the wavelengths $\lambda_{1-n}$, then the concentration level C of the substance may be determined from the spectral response for each of the wavelengths (and in one aspect including a range of 1 nm to 50 nm around each of the wavelengths). Using the spectral response at multiple frequencies provides a more robust determination of the concentration level of the substance.

Figure 14:
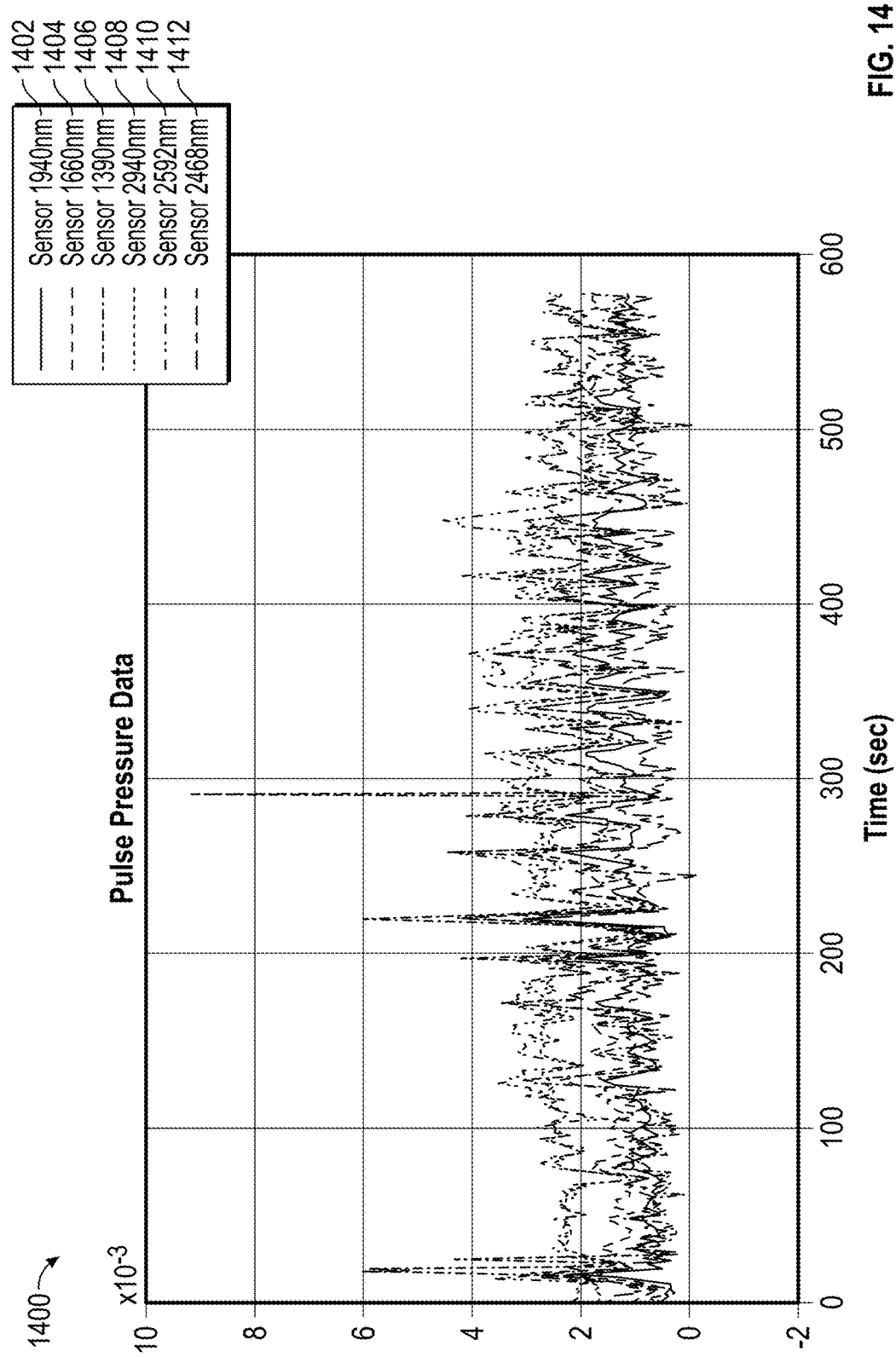
FIG. 14 illustrates an exemplary graph of spectral responses of a plurality of wavelengths from clinical data using the biosensor.

In use, the biosensor 100 transmits light directed at living tissue at a plurality of discrete wavelengths or over a broad spectrum at 1302. The spectral response of light from the living tissue is detected at 1304, and the spectral response is analyzed for a plurality of wavelengths (and in one aspect including a range of +/−20 to 50 nm around each of the wavelengths) at 1306. Then, the concentration level C of the substance may be determined from the spectral response for each of the plurality of wavelengths at 1308. An example for calculating the concentration of one or more substances over multiple wavelengths may be performed using a linear function, such as is illustrated herein below.

$$LN(I_{1-n})=\Sigma_{i=0}^{n}\mu i*Ci$$

wherein, $I_{1-n}$=intensity of light at wavelengths $\lambda_{1-n}$ $\mu_n$=absorption coefficient of substance 1, 2, . . . n at wavelengths $\lambda_{1-n}$ $C_n$=Concentration level of substance 1, 2, . . . n FIG. 14 illustrates an exemplary graph 1400 of spectral responses of a plurality of wavelengths from clinical data using the biosensor 100. In this embodiment, the spectral response of a plurality of wavelengths was measured using the biosensor 100 over a measurement period of almost 600 seconds or approximately 10 minutes. The graph illustrates the spectral response for a first wavelength 1402 of approximately 940 nm, the spectral response for a second wavelength 1404 of approximately 660 nm and the spectral response for a third wavelength 1406 of approximately 390 nm obtained from a first biosensor 100 measuring reflected light from a first fingertip of a patient. The graph further illustrates the spectral response for a fourth wavelength 1410 of approximately 592 nm and a fifth wavelength 1412 of approximately 468 nm and the spectral response 1408 again at 940 nm obtained from a second biosensor measuring reflected light from a second fingertip of a patient. The spectral responses are temporally aligned using the systolic and diastolic points. Though two biosensors were used to obtain the spectral responses in this clinical trial, a single biosensor 100 may also be configured to obtain the spectral responses of the plurality of wavelengths.

Various unexpected results were determined from clinical trials using the biosensor 100. In one aspect, based on the clinical trials, an R value obtained from the ratio $L_{\lambda1=390\ nm}/$ and $L_{\lambda2=940}$ was found to be a predictor or indicator of diabetic risk or diabetes as described in more detail herein. In another aspect, based on the clinical trials, the R value obtained from the ratio of $L_{468\ nm}/L_{940\ nm}$, was identified as an indicator of the liver enzyme marker, e.g. P450. In another aspect, based on the clinical trials, the R value obtained from the ratio of $L_{592\ nm}/L_{940\ nm}$, was identified as an indicator of digestion phases, such as phase 1 and phase 2, in the arterial blood flow. In another aspect, the R value from the ratio of $L_{660\ nm}/L_{940\ nm}$, was found to be an indicator of oxygen saturation levels $SpO_2$ in the arterial blood flow. In another aspect, it was determined that the biosensor 100 may determine alcohol levels in the blood using spectral responses for wavelengths at 390 and/or 468 nm. In general, the second wavelength of 940 nm is selected because it has a low absorption coefficient for the targeted substances described herein. Thus, another wavelength other than 940 nm with a low absorption coefficient for the targeted substances (e.g. at least less than 25% of the absorption coefficient of the targeted substance for the first wavelength) may be used instead. For example, the second wavelength of 940 nm may be replaced with 860 nm that has a low absorption coefficient for the targeted substances. In another aspect, the second wavelength of 940 nm may be replaced with other wavelengths, e.g. in the IR range, that have a low absorption coefficient for the targeted substances. In general, it is desired that the spectral response for the first predetermined wavelength have a higher intensity level than the spectral response for the second predetermined wavelength.

In another aspect, it was determined that other proteins or compounds, such as those present or with higher concentrations in the blood with persons having cancer, may be detected using similar PPG techniques described herein with biosensor 100 at one or more other wavelengths. Cancer risk may then be determined using non-invasive testing over a short measurement period of 1-10 minutes. Since the biosensor may operate in multiple frequencies, various health monitoring tests may be performed concurrently. For example, the biosensor 100 may measure for diabetic risk, liver enzymes, alcohol levels, cancer risk or presence of other analytes within a same measurement period using PPG techniques.

Figure 15:
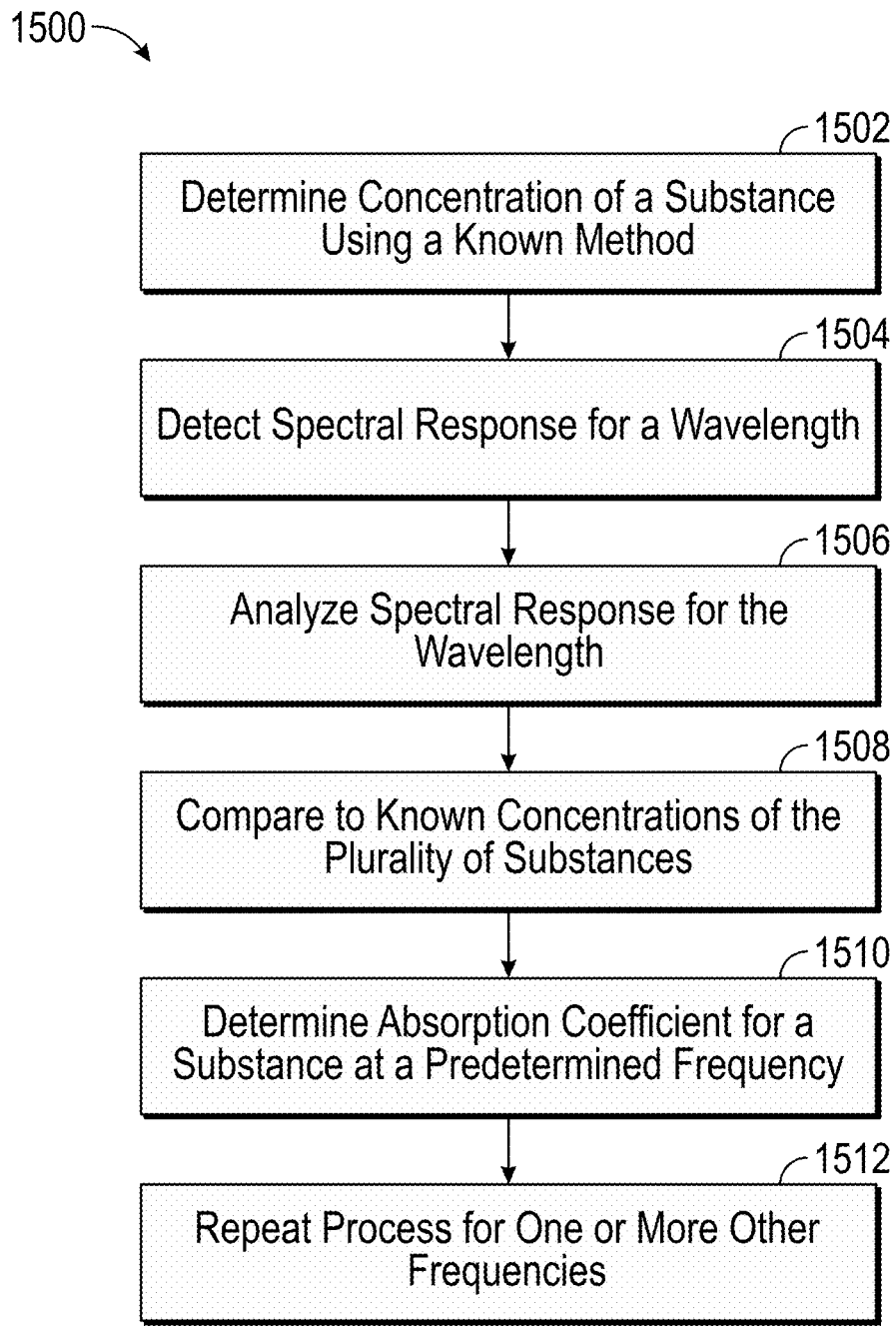
FIG. 15 illustrates a logical flow diagram of an exemplary method to determine an absorption coefficients $\mu$ of a substance at a wavelength $\lambda$.

FIG. 15 illustrates a logical flow diagram of an exemplary method 1500 to determine an absorption coefficients µ of a substance at a wavelength λ. The concentration level of a substance in arterial blood is obtained using a known method at 1502. For example, blood may be extracted at predetermined intervals during a time period and a blood gas analyzer may be used to measure a concentration level of a substance. The biosensor 100 emits light at a wavelength (and in one aspect for a range of 1 nm-50 nm around the wavelength) and detects a spectral response for the wavelength (and in one aspect for a range of 1 nm-50 nm around the wavelength). The spectral response for the predetermined wavelength is analyzed at 1506. The intensity of the detected light is determined. The intensity of the detected light is compared to the known concentration level of the substance at 1508. The absorption coefficient for the substance may then be determined using the Beer-Lambert equations described herein at 1510.

The above process may be repeated at one or more other frequencies at 1512. For example, as described herein, the spectral analysis over a range or at multiple frequencies may be analyzed to determine one or more frequencies with a higher intensity or power level in response to a concentration level or presence of the substance. Thus, one or more frequencies may be analyzed and identified for detection of the substance, and the absorption coefficient for the substance determined at the one or more frequencies.

In another embodiment, the concentration level of a substance may be obtained from predetermined values obtained through experimentation. For example, in a calibration phase, a correlation table may be compiled through experimentation that includes light intensity values $I_{1-n}$ at one or more wavelengths $\lambda_{1-n}$ and a corresponding known concentration level for the substance for the light intensity values. In use, the biosensor 100 detects a spectral response and determines the light intensity values $I_{1-n}$ at one or more wavelengths $\lambda_{1-n}$. The biosensor 100 then looks up the detected light intensity values $I_{1-n}$ in the correlation table to determine the concentration level of the substance.

Figure 16:
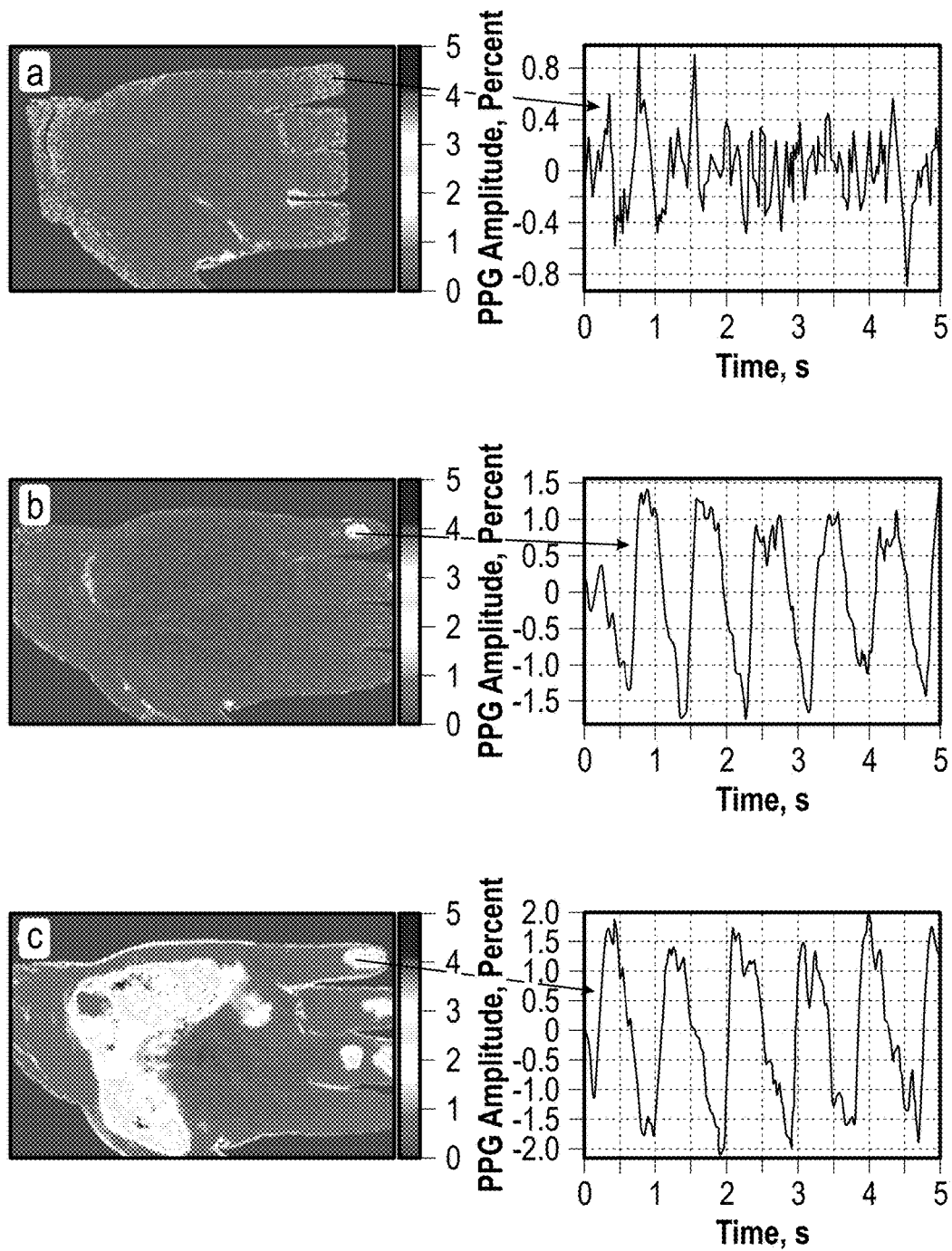
FIG. 16 illustrates a logical flow diagram of an embodiment of a method of determining concentration levels of one or more substances.

FIG. 16 illustrates a schematic block diagram of a spatial distribution of light intensity amplitude for different forces of contact between the biosensor 100 and a skin surface. Spatial distribution of the PPG amplitude for different forces of contact was measured between a glass table and skin of one of the subjects during steps a, b and c. The results of the experiment are illustrated in FIG. 16 wherein the spatial distributions of the PPG-amplitude obtained during the steps a, b, and c are presented respectively. The mechanical contact of the glass with the subject's skin substantially increases the amplitude of the observed PPG signal. Moreover, by increasing the force of the contact, the amplitude of the PPG signal and the area with elevated PPG amplitude is increased. As such, compression enhances the PPG signal. So compression of the biosensor 100 against the skin of a patient may be implemented during use of biosensor 100 in its one or more form factors. The article by Kamshilin A A, Nippolainen E, Sidorov I S, et al. entitled "A new look at the essence of the imaging photoplethysmography" in Scientific Reports, May 21, 2015, 5:10494 and doi:10.1038/srep10494 includes further details on spatial distribution of PPG intensity amplitude for different forces of contact, and is hereby incorporated by reference herein.

Embodiment—Biosensor Form Factors

Figure 17A:
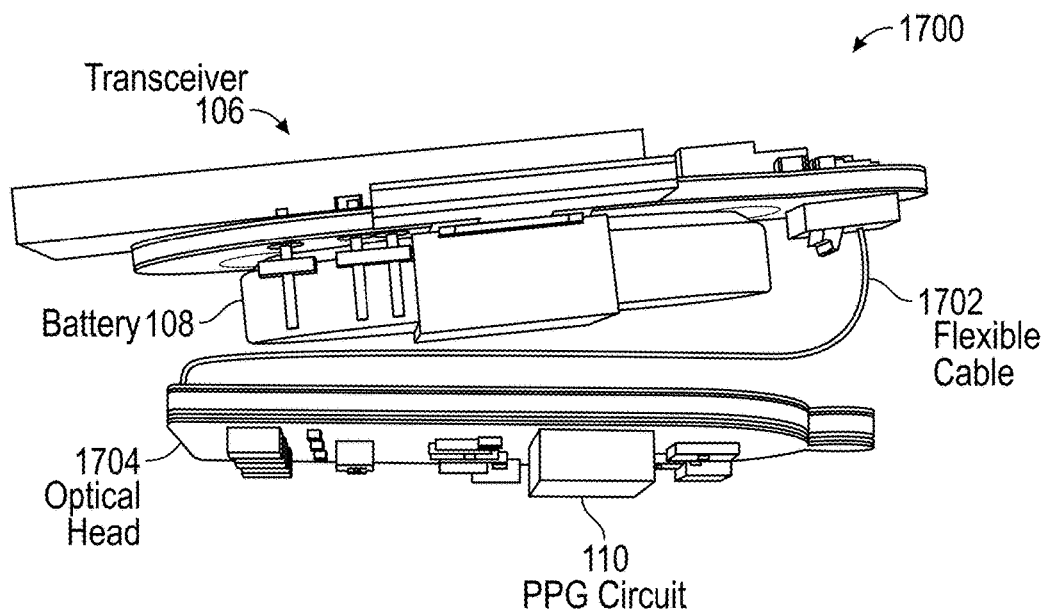
FIG. 17A illustrates an exemplary embodiment of a form factor of the biosensor.

FIG. 17A illustrates an exemplary embodiment of a form factor of the biosensor 100. In an embodiment, the biosensor 100 is implemented on a wearable patch 1700. The wearable patch 1700 may include an adhesive backing to attach to a skin surface of a patient, such as on a hand, arm, wrist, forehead, chest, abdominal area, or other area of the skin or body or living tissue. Alternatively, the wearable patch 1700 may be attached to the skin surface using adhesive tape. A flexible cable 1702 may be used to attach an optical head 1704 of the wearable patch 1700 to the other components of the biosensor 100, such as the wireless transceiver 106 and battery 108. Thus, during a magnetic resonance imaging (MRI) test when metal needs to be minimal, the battery 108 and transceiver 106 may be temporarily removed. In addition, the flexible cable 1702 may be used to open the biosensor 100 to replace the battery 108.

Figure 17B:
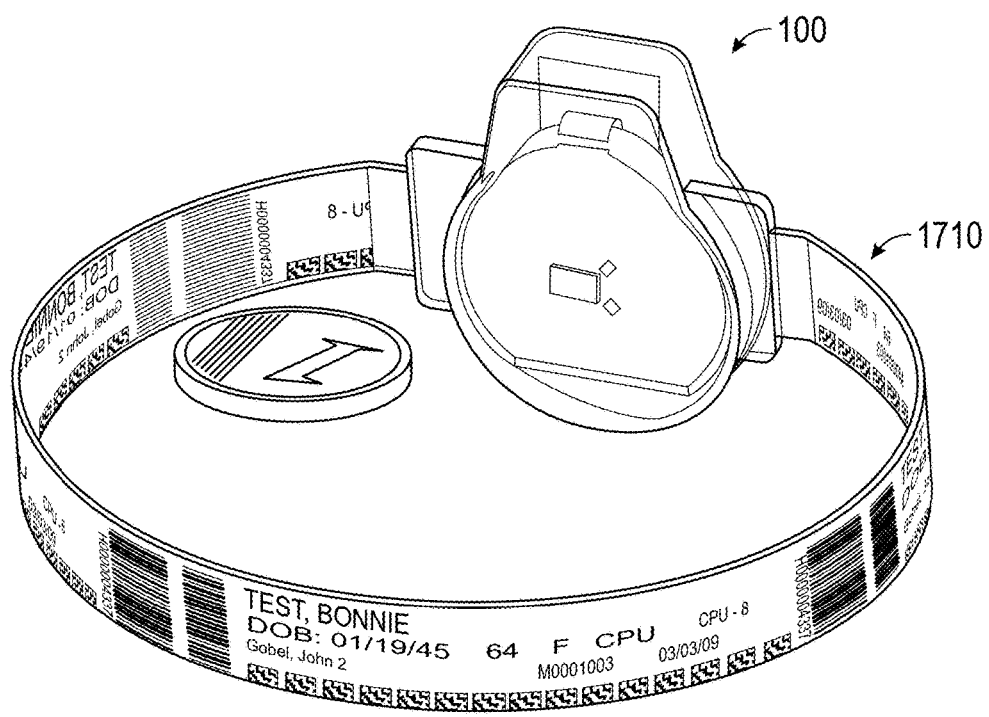
FIG. 17B illustrates an exemplary embodiment of another form factor of the biosensor.

FIG. 17B illustrates an exemplary embodiment of another form factor of the biosensor 100. In this embodiment, the biosensor 100 is implemented on an arm band 1710. The arm band 1710 may be configured with an adjustable band for placement on an arm, wrist, on one or more fingers, around a leg, etc. In general, the arm band 1710 should be secured such that the PPG circuit 110 is positioned to direct light towards the skin surface.

Figure 18A:
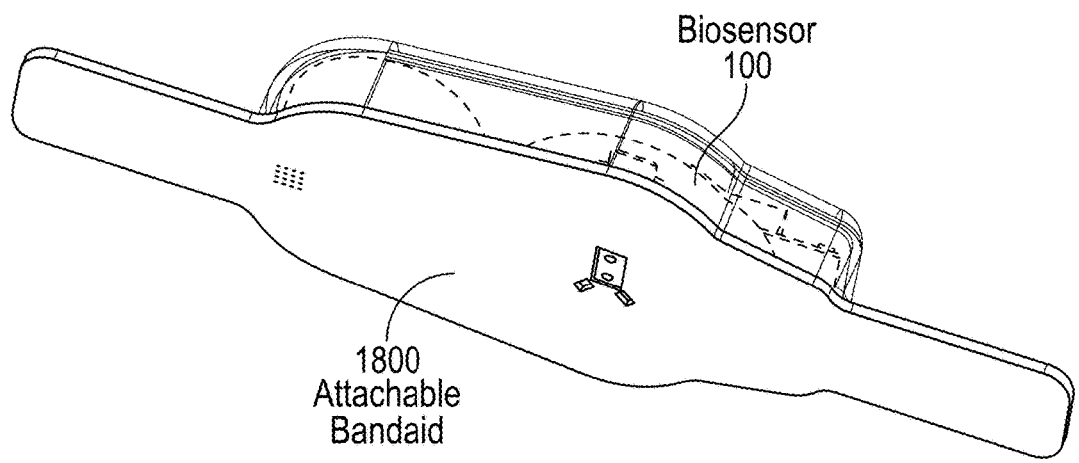
FIG. 18A illustrates an exemplary embodiment of another form factor of the biosensor.

FIG. 18A illustrates an exemplary embodiment of another form factor of the biosensor 100. In this embodiment, the biosensor 100 may be coupled to an attachable bandaid 1800. The attachable bandaid 1800 may be attached via adhesive or adhesive tape to a skin surface of the patient, e.g. finger, forehead, arm, stomach, leg, wrist, etc.

Figure 18B:
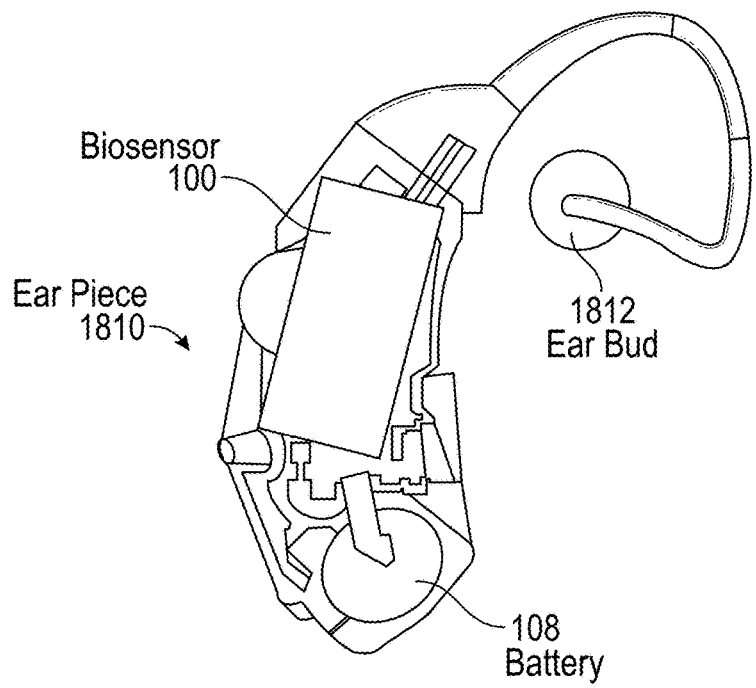
FIG. 18B illustrates an exemplary embodiment of another form factor of the biosensor.

FIG. 18B illustrates an exemplary embodiment of another form factor of the biosensor 100. In this embodiment, the biosensor 100 is configured in an earpiece 1810. The earpiece 1810 includes an earbud 1812. The biosensor 100 is configured to transmit light into the ear canal from one or more optical fibers in the ear bud 1812 and detect light from the ear canal using one or more optical fibers.

Figure 19A:
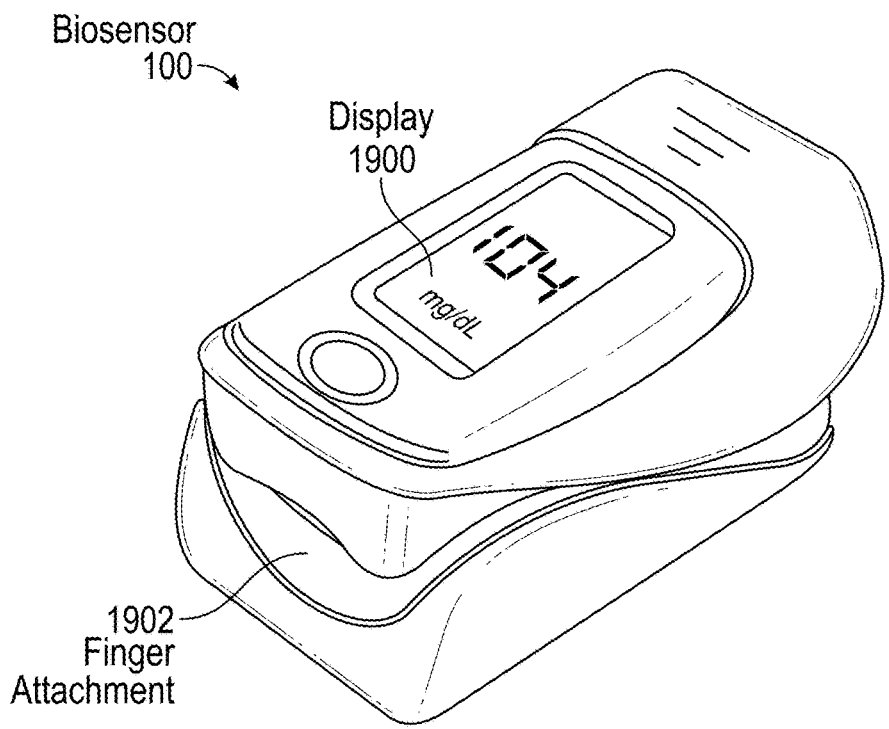
FIG. 19A illustrates an exemplary embodiment of another form factor of the biosensor.

FIG. 19A illustrates an exemplary embodiment of another form factor of the biosensor 100. In this embodiment, the biosensor 100 is configured to attach to a finger or fingertip using finger attachment 1902. The finger attachment 1902 is configured to securely hold a finger that is inserted into the finger attachment 1902. A display 1900 is implemented on the biosensor 100 with a graphical user interface (GUI) that displays biosensor data. For example, in use, the biosensor 100 measures blood glucose levels using the PPG circuit 110. The blood glucose levels are then displayed using the GUI on the display 1900. The PPG circuit may also measure other patient vitals that are displayed on the display 1900, such as oxygen saturation levels, temperature, blood alcohol levels, digestive response, calorie intake, white blood cell count, electrolyte or other blood analyte concentrations, liver enzymes, etc. The biosensor 100 may thus provide biosensor data non-invasively without a blood sample.

Figure 19B:
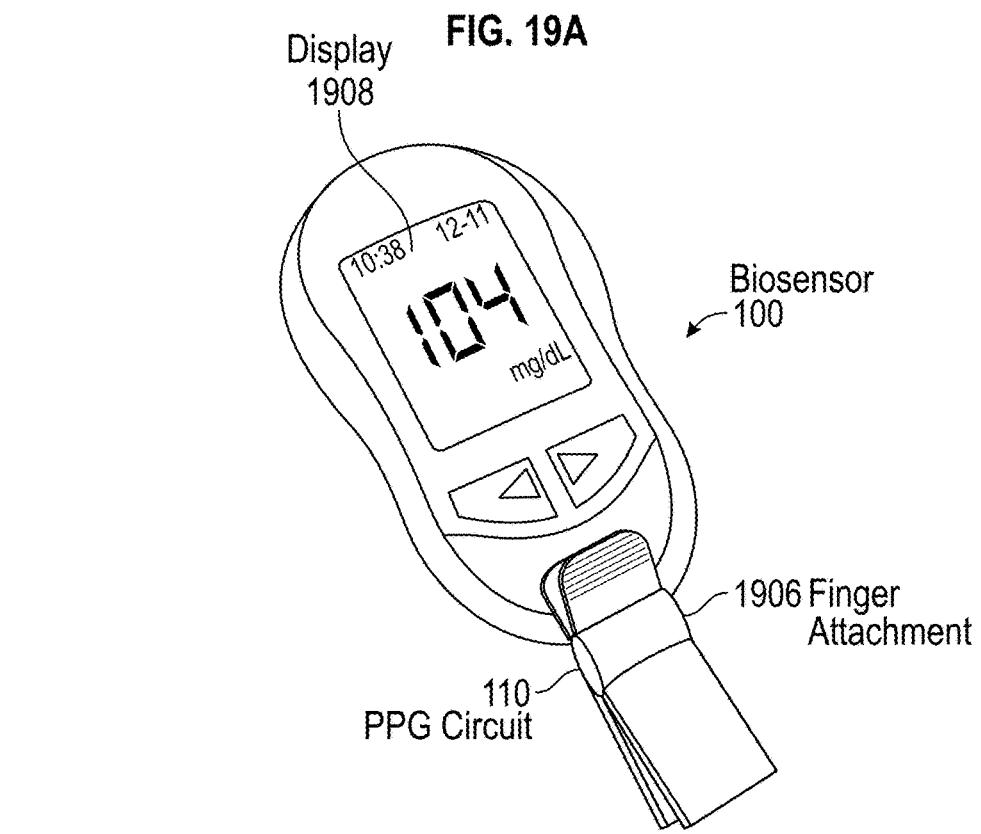
FIG. 19B illustrates an exemplary embodiment of another form factor of the biosensor.

FIG. 19B illustrates an exemplary embodiment of another form factor of the biosensor 100. In this embodiment, the biosensor 100 is configured to attach to a finger or fingertip using finger attachment 1906. The finger attachment 1906 includes the PPG circuit 110 and is configured to securely hold a finger that is inserted into the finger attachment 1906. The finger attachment 1906 may be implemented within the same encasement as the other components of the biosensor 100 or be communicatively coupled either through a wired or wireless interface to the other components of the biosensor 100. A display 1908 is implemented for the biosensor 100 with a graphical user interface (GUI) that displays biosensor data including blood glucose levels.

The biosensor 100 may be configured to be attached to an ear lobe or other body parts in other form factors. In addition, one or more biosensors 100 in one or more form factors may be used in combination to determine biosensor data at one or more areas of the body.

Embodiment—Determination of NO Concentration Levels Using Shifts in Absorbance Peaks In another embodiment, a concentration level of nitric oxide (NO) may be obtained from measuring a characteristic shift in an absorbance peak of hemoglobin. For example, the absorbance peak for methemoglobin shifts from around 433 nm to 406 nm in the presence of NO. The advantage of the measurement of NO by monitoring methemoglobin production includes the wide availability of spectrophotometers, avoidance of sample acidification, and the relative stability of methemoglobin. Furthermore, as the reduced hemoglobin is present from the beginning of an experiment, NO synthesis can be measured continuously, removing the uncertainty as to when to sample for NO.

The biosensor 100 may detect nitric oxide in vivo using PPG techniques by measuring the shift in the absorbance spectra curve of reduced hemoglobin in pulsating blood flow. The absorbance spectra curve of reduced hemoglobin shifts with a peak from around 430 nm to a peak around 411 nm depending on the production of methemoglobin. The greater the degree of the shift of the peak of the curve, the higher the production of methemoglobin and NO concentration level. Correlations may be determined between the degree of the measured shift in the absorbance spectra curve of reduced hemoglobin to an NO concentration level. The correlations may be determined from a large sample population or for a particular patient and stored in a calibration database. The biosensor 100 may thus obtain an NO concentration level by measuring the shift of the absorbance spectra curve of reduced hemoglobin.

In addition, the absorbance spectra curve of deoxygenated HB has a peak of around 430 nm. After a one minute time period of exposure to a nitric oxide mixture, the absorbance spectra curve of deoxygenated HB shifts to a peak of around 405 nm. In addition, the absorbance spectra curve of oxygenated HB has a peak around 421 nm. After a twenty minute time period of exposure to a nitric oxide mixture, the absorbance spectra curve of oxygenated HB shifted to a peak of around 393 nm. The Deoxygenated Hb has an absorption peak at 430 nm and in the presence of NO has a peak shift to 405 nm. The Oxygenated Hb has absorption peak at 421 nm in presence of NO has peak shift to 393 nm.

The biosensor 100 may obtain an NO concentration level by measuring the shift of the absorbance spectra curve of deoxygenated hemoglobin and/or by measuring the shift of the absorbance spectra curve of oxygenated hemoglobin in vivo. The biosensor 100 may then access a calibration database that correlates the measured shift in the absorbance spectra curve of deoxygenated hemoglobin to an NO concentration level. Similarly, the biosensor may access a calibration database that correlates the measured shift in the absorbance spectra curve of oxygenated hemoglobin to an NO concentration level.

Figure 20:
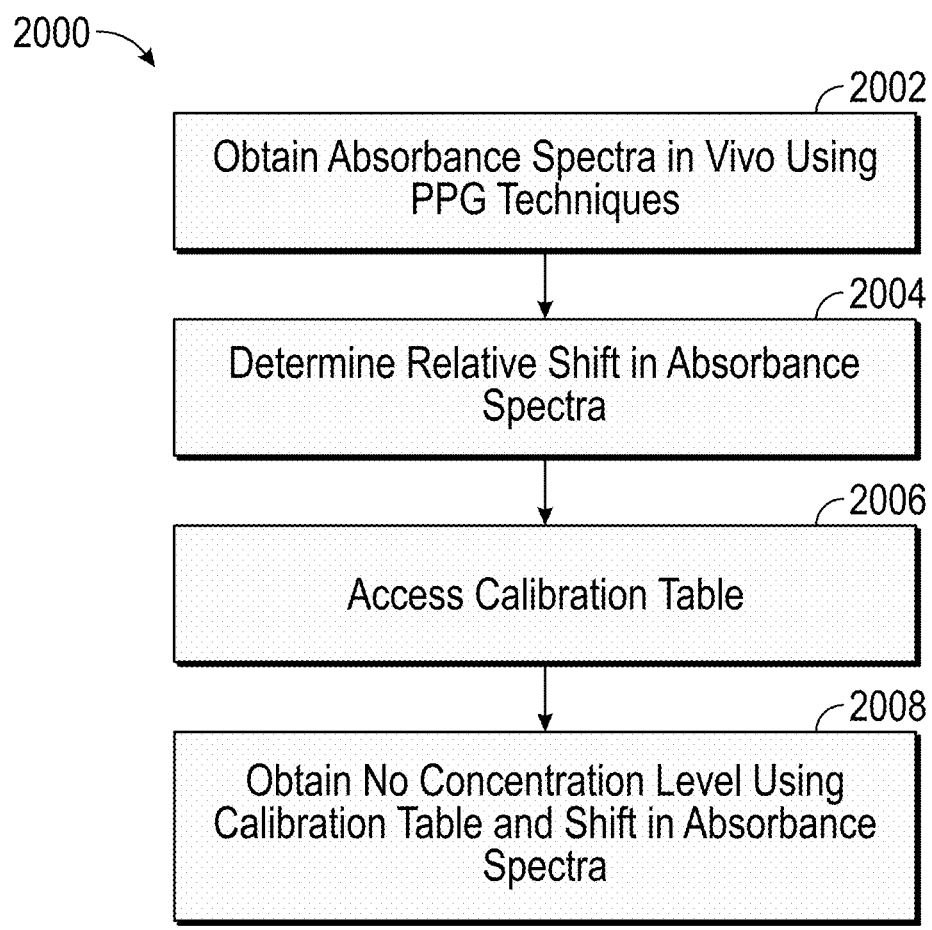
FIG. 20 illustrates a logical flow diagram of an exemplary embodiment of a method for measuring nitric oxide (NO) concentration levels in vivo using shifts in absorbance spectra.

FIG. 20 illustrates a logical flow diagram of an exemplary embodiment of a method 2000 for measuring NO concentration levels in vivo using shifts in absorbance spectra. The biosensor 100 may obtain a concentration of NO by measuring shifts in absorbance spectra of one or more substances that interact with NO. For example, the one or more substances may include oxygenated and deoxygenated hemoglobin (HB). The PPG circuit 110 detects a spectral response at a plurality of wavelengths of the one or more substances that interact with NO at 2002. The biosensor 100 determines the relative shift in the absorbance spectra for the substance at 2004. For example, the biosensor 100 may measure the absorbance spectra curve 1502 of deoxygenated HB and determine its relative shift or peak between the range of approximately 430 nm and 405 nm. In another example, the biosensor 100 may measure the absorbance spectra curve of oxygenated HB and determine its relative shift or peak between 421 nm and 393 nm.

The biosensor 100 accesses a calibration database that correlates the relative shift in the absorbance spectra of the substance with a concentration level of NO at 2006. The biosensor 100 may thus obtain an NO concentration level using calibration database and the measured relative shift in absorbance spectra of the spectrum at 2008.

Figure 21:
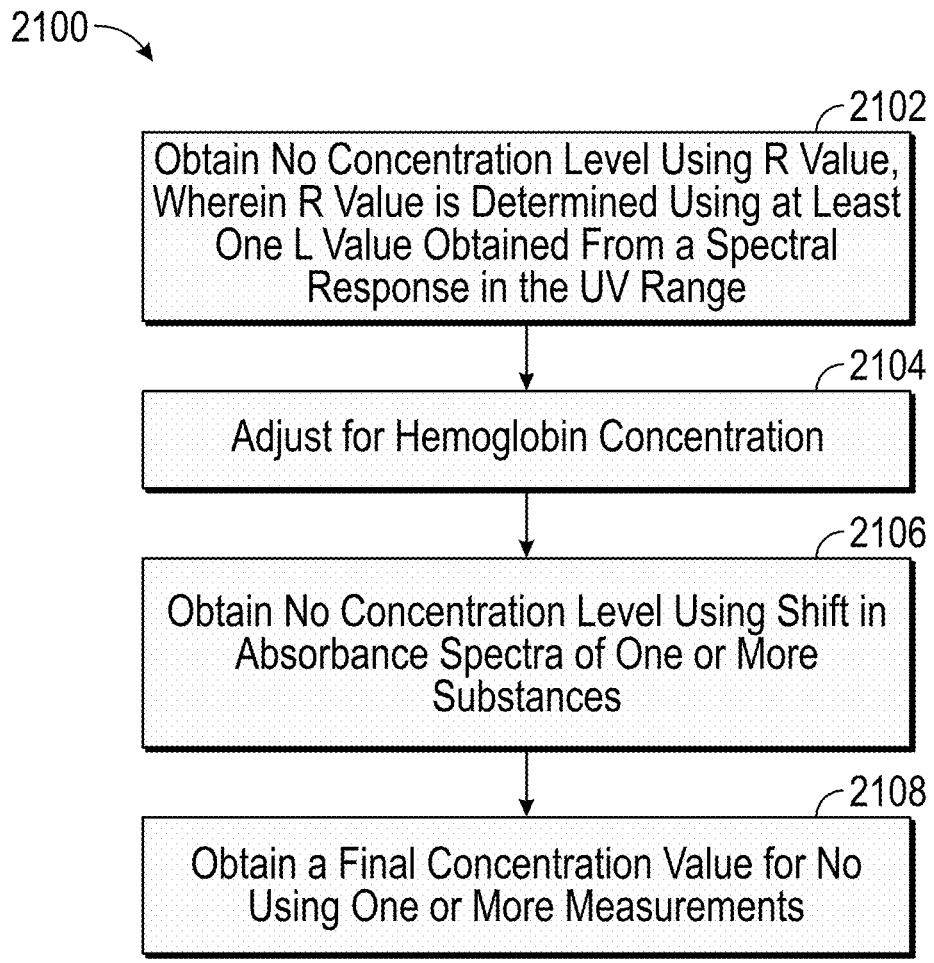
FIG. 21 illustrates a logical flow diagram of an exemplary embodiment of a method for measuring nitric oxide (NO) concentration levels using one or more measurement techniques.

FIG. 21 illustrates a logical flow diagram of an exemplary embodiment of a method 2100 for measuring NO concentration levels using one or more measurement techniques. In an embodiment, the biosensor 100 is configured to determine a concentration level of NO in vivo using PPG technology and one or more measurement techniques described herein. For example, the biosensor 100 may determine an R value using at least one L value obtained from a spectral response in the UV range at 2102. For example, the R value may be obtained using, e.g. an L Value in the range from 380-410 such as 390 nm or 395 nm and accessing a calibration database that maps the R value to an NO concentration level. In another example, the biosensor 100 may determine an NO concentration level using over a plurality of wavelengths and adjusting or compensating for hemoglobin concentrations at 2104. In another example, the biosensor 100 may determine the relative shift in the absorbance spectra for a substance (such as hemoglobin) and access a calibration database that correlates the relative shift in the absorbance spectra of the substance with a concentration level of NO at 2106.

The biosensor 100 may use a plurality of these methods to determine a plurality of values for the concentration level of NO at 2108. The biosensor 100 may determine a final concentration value using the plurality of values. For example, the biosensor 100 may average the values, obtain a mean of the values, etc.

Embodiment—Diabetic Parameter Measurements

Clinical data obtained using the biosensor 100 is now described herein. The biosensor 100 was used to monitor concentration levels or indicators of one or more substances in the blood flow of the patient in the clinical trials over a measurement time period. For example, the biosensor 100 was used in the clinical trials to non-invasively detect diabetic parameters, such as insulin response over time, nitric oxide (NO) levels, glucose levels, and predict diabetic risk or diabetic precursors, in pulsatile arterial blood flow. The biosensor 100 was also used to detect blood alcohol levels in pulsatile arterial blood flow. The biosensor 100 was also used to detect digestive parameters, such as digestion phase 1 and 2 responses. The biosensor 100 also detected heart rate and blood oxygen saturation levels in the clinical trials.

Figure 22:
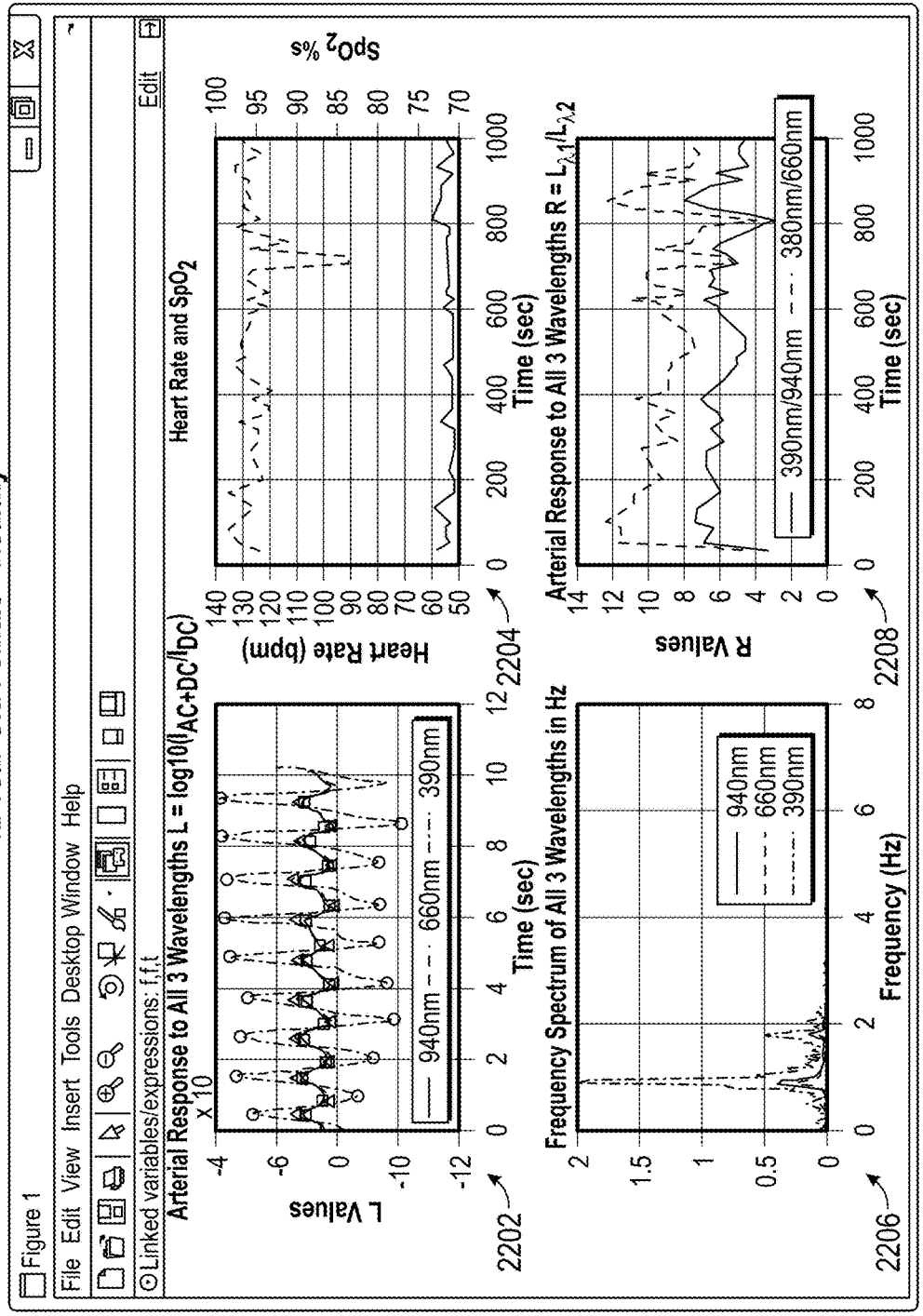
FIG. 22 illustrates a schematic drawing of an exemplary embodiment of results of clinical data obtained using the biosensor from a first patient.

FIG. 22 illustrates a schematic drawing of an exemplary embodiment of results of clinical data 2200 obtained using the biosensor 100 from a first patient. This first patient is a 42 year old female with no known diagnosis of diabetes. A biosensor 100 is placed on at least one finger of the first patient and the spectral response is measured over the least three wavelengths at 390 nm, 660 nm and 940 nm (and also in range of 1 nm to 50 nm). The graph 2006 illustrates the spectral response or frequency spectrum data obtained for the three wavelengths. The spectral response in graph 2206 shows the frequency versus the relative intensity measured by the biosensor 100. The graph 2202 illustrates the L value obtained from the spectral responses for each of the three wavelengths obtained, e.g., from the spectral response data shown in graph 2206. The L value obtained for the three wavelengths is a measured response from the pulsating arterial blood flow in the patient.

The graph 2208 illustrates the calculated Ratio R for $R_1=L_{390\ nm}/L_{940\ nm}$ and $R_2=L_{390\ nm}/L_{660\ nm}$. In one aspect, based on unexpected results from clinical trials, it was determined that a ratio R value obtained at approximately $L_{\lambda 1}=390$ nm and $L_{\lambda 2}=940$ nm is useful as a predictor or indicator of diabetic risk or diabetes. For example, during experimental clinical trials, spectral responses were obtained during a measurement period over a 1-2 minute time period for wavelengths of 390 nm and 940 nm (and also in ranges of 1 nm to 50 nm including these wavelengths). An R value was obtained based on the spectral responses. From the unexpected results of the clinical trials, an R value obtained during a period of fasting, e.g. prior to ingestion of food or liquids, of less than 1 (e.g., approximately 0.5) indicated that a person has diabetes or early onset of diabetes. An R value of 2 or above indicated that a person has a lower risk of a diabetes diagnosis. An R value in the 5-6 range indicated no current risk of diabetes. For example, as shown in graph 2208, the R value obtained for $L_{\lambda 1}$=390 nm and $L_{\lambda 2}$=940 nm has an average value greater than 5 in this first patient without a diabetes diagnosis.

Figure 23:
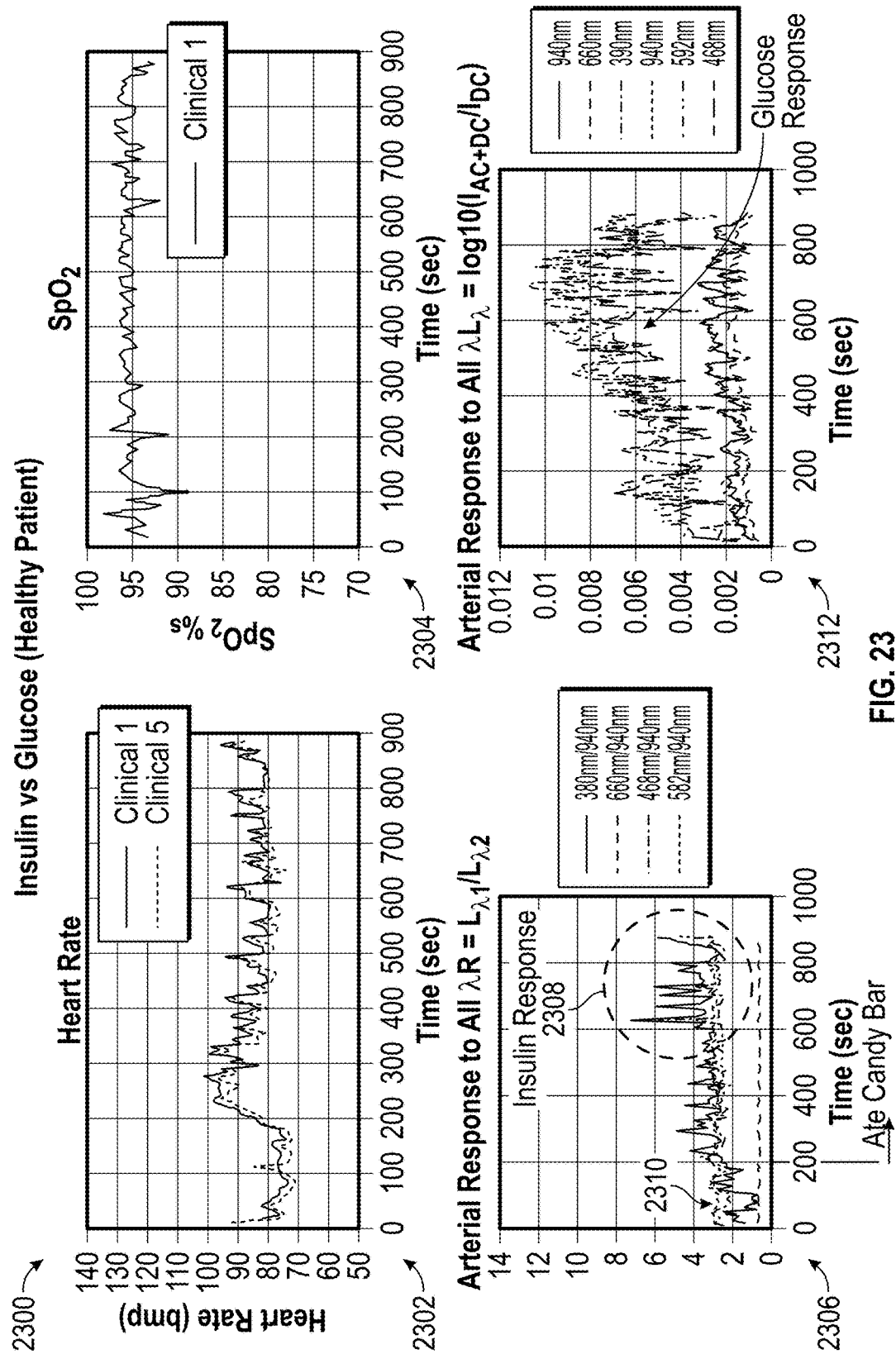
FIG. 23 illustrates a schematic drawing of another exemplary embodiment of results of clinical data obtained using the biosensor from the first patient.

FIG. 23 illustrates a schematic drawing of another exemplary embodiment of results of clinical data 2300 obtained using the biosensor 100 from the first patient. The graph 2302 illustrates the heart rate obtained over a measurement period of 900 seconds. The graph 2304 illustrates the oxygen saturation level $SpO_2$ obtained over the measurement period of 900 seconds.

The graph 2306 illustrates an insulin response measured in the arterial blood flow of the patient over a measurement period of 900 seconds. The graph illustrates the Ratio R for approximately $L_{390\ nm}/L_{940\ nm}$, for approximately $L_{660\ nm}/L_{940\ nm}$, for approximately $L_{466\ nm}/L_{940\ nm}$, and for approximately $L_{582\ nm}/L_{940\ nm}$. In unexpected results, the Ratio R value for $L_{390\ nm}/L_{940\ nm}$ 2310 between 0 and 200 seconds is seen to correlate with the base insulin resistance factor, e.g. the base insulin concentration levels after fasting for 2-8 hours. At approximately, 200 seconds, the patient consumed a high sugar substance, e.g. a candy bar. In unexpected results, the insulin response 2308 of the patient is obtained from the biosensor data. In particular, the Ratio R for approximately $L_{390\ nm}/L_{940\ nm}$ shows the increase in insulin response 2308 from the base insulin resistance factor 2310 in the pulsating arterial blood flow starting at approximately 600 seconds in response to the consummation of the high sugar substance. The Ratio R for approximately $L_{390\ nm}/L_{940\ nm}$ has a value between 4 and 6 in the healthy patient without a diagnosis of diabetes in response to the ingestion of the high sugar substance.

Graph 2312 illustrates the L values obtained from the spectral responses for the four wavelengths, $L_{940\ nm}$, $L_{660\ nm}$, $L_{390\ nm}$, $L_{582\ nm}$, and $L_{463\ nm}$ over the measurement period of 900 seconds. The glucose response from the consummation of the high sugar substance is starting at approximately 600 seconds. In particular, in unexpected results, it is believed that nitric oxide NO levels in the arterial blood flow is being measured at least in part by the biosensor 100 using the spectral response for the wavelength 390 nm (and 1 nm-50 nm range around 390 nm). The spectral response is responsive to nitric oxide (NO) concentration levels in the blood. As such, the $L_{390\ nm}$ values may be used to determine nitric oxide (NO) concentration levels in the pulsating blood flow.

In addition, insulin in the blood generates NO as it penetrates blood vessel walls. The NO is released as a gas before attaching to one or more hemoglobin type molecules. Since at least part of the NO gas concentration is in a gaseous form in the arterial blood flow, the NO in the gaseous form will dissipate prior to measurement from in vitro blood samples. As such, the complete NO concentration levels may not be measured using in vitro blood samples, e.g. from a finger prick. Thus, the biosensor 100 measurements, e.g. using the spectral response and calculated L values at 390 nm, are the first time NO levels in arterial blood flow have been measured in vivo. These unexpected results of measuring nitric oxide NO concentration levels in pulsating arterial blood flow are obtained non-invasively and continuously over a measurement period using the biosensor 100.

From the clinical trials performed, it has been determined that the measured NO levels are an indication of insulin response and blood glucose concentration levels in the blood. The R value derived from $L_{390\ nm}/L_{940\ nm}$ may thus be used as an indicator of insulin response and diabetic risk as well as vascular health. These unexpected results have advantages in early detection of diabetic risk and easier, non-invasive monitoring of insulin resistance and blood glucose levels. The biosensor 100 may display the R value or an analysis of the diabetic risk based on the R value. In one aspect, the biosensor 100 may display, no diabetic risk based on R values of 5 or greater. In another aspect, the biosensor 100 may display, low diabetic risk based on R values of 2-5. In another aspect, the biosensor 100 may display, high diabetic risk based on an R values of 1-2. In another aspect, the biosensor 100 may display, diabetic condition detected based on an R value less than one.

Figure 24:
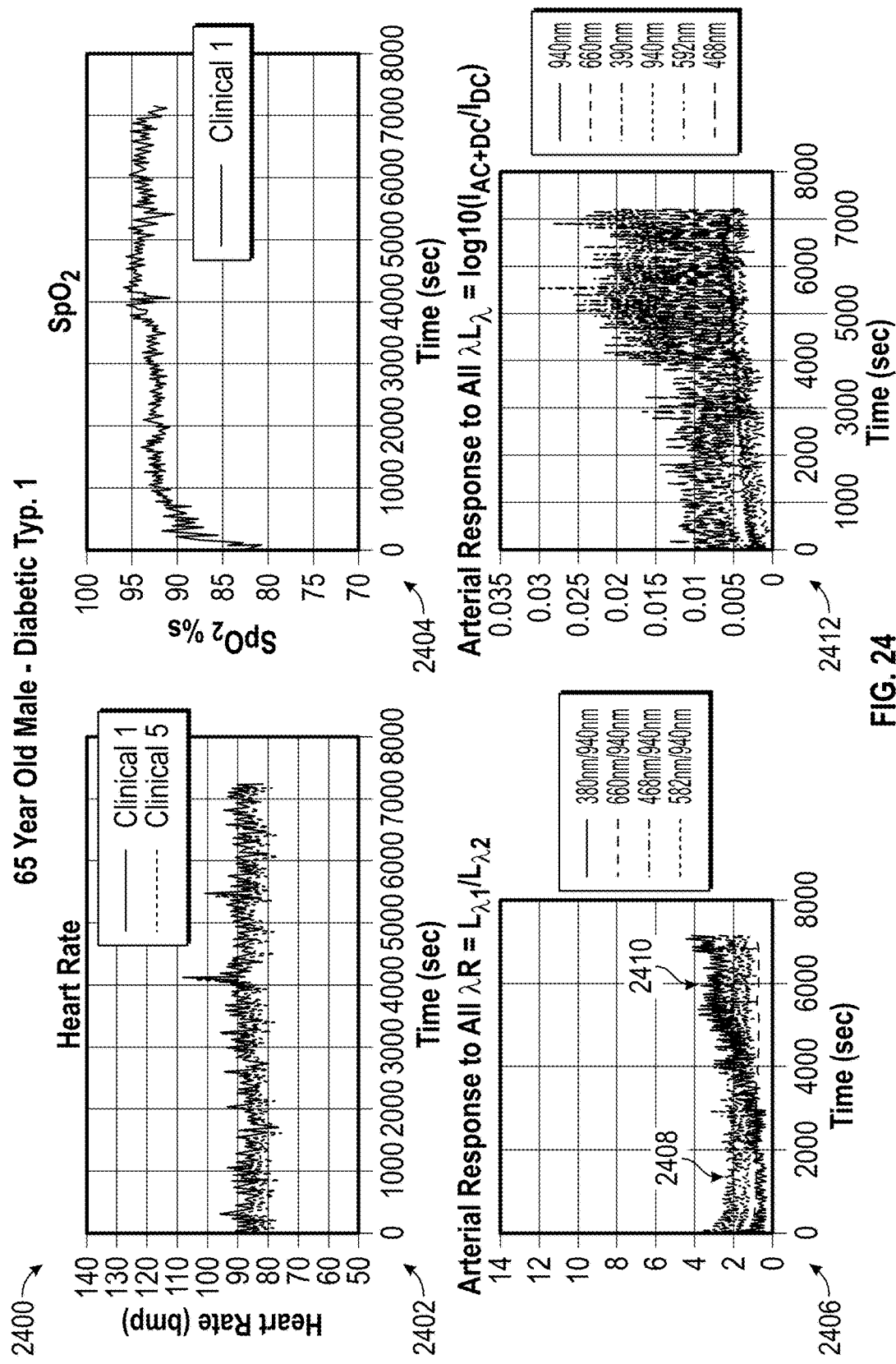
FIG. 24 illustrates a schematic drawing of another exemplary embodiment of results of clinical data obtained using the biosensor from a second patient.

FIG. 24 illustrates a schematic drawing of another exemplary embodiment of results of clinical data 2400 obtained using the biosensor 100 from a second patient. The second patient was a 65 year old male with a known diagnosis of type 1 diabetes. The graph 2402 illustrates the heart rate obtained over a measurement period of approximately 135 minutes. The graph 2404 illustrates the oxygen saturation level SpO2 obtained over the measurement period of 135 minutes.

The graph 2406 illustrates an insulin response 2410 measured in the arterial blood flow of the patient over a measurement period of 135 minutes. The graph illustrates the Ratio R for approximately $L_{390\ nm}/L_{940\ nm}$, for approximately $L_{660\ nm}/L_{940\ nm}$, for approximately $L_{466\ nm}/L_{940\ nm}$, and for approximately $L_{582\ nm}/L_{940\ nm}$. In unexpected results, the Ratio R for approximately $L_{390\ nm}/L_{940\ nm}$ correlates with a base insulin resistance factor shown prior to approximately 200 seconds. At approximately, 200 seconds, the patient consumed a high sugar substance, e.g. a glucose drink. In unexpected results, the insulin response 2410 of the patient is obtained from the biosensor data. In particular, the Ratio R for approximately $L_{390\ nm}/L_{940\ nm}$ shows the minimal insulin response 2410 in the patient with diabetes after the consummation of the glucose drink. The R value for $L_{390\ nm}/L_{940\ nm}$ remains below a value of 1 even after the consummation of the glucose drink indicating the lack of generation of natural insulin by the patient. At approximately 4500 seconds or 75 minutes, insulin is administered to the patient through two injections. The graph 2406 illustrates the increase in the R value due to the increase in insulin response 2410 from the injections after 4500 seconds. The Ratio R for approximately $L_{390\ nm}/L_{940\ nm}$ still remains low with a value between 2 and 4 even after the insulin injections in the patient with diabetes.

Graph 2412 illustrates the L values for the four wavelengths, $L_{940\ nm}$, $L_{660\ nm}$, $L_{390\ nm}$, $L_{582\ nm}$, and $L_{463\ nm}$ over the measurement period of 1000 seconds. The graph of $L_{390}$ 2408 shows no increase in insulin levels until after the insulin injections at 75 minutes. In specific, the $L_{390\ nm}$ shows particularly sensitivity in the measurement of the base insulin resistance factor measured after fasting and the insulin response measured after caloric intake.

Figure 25:
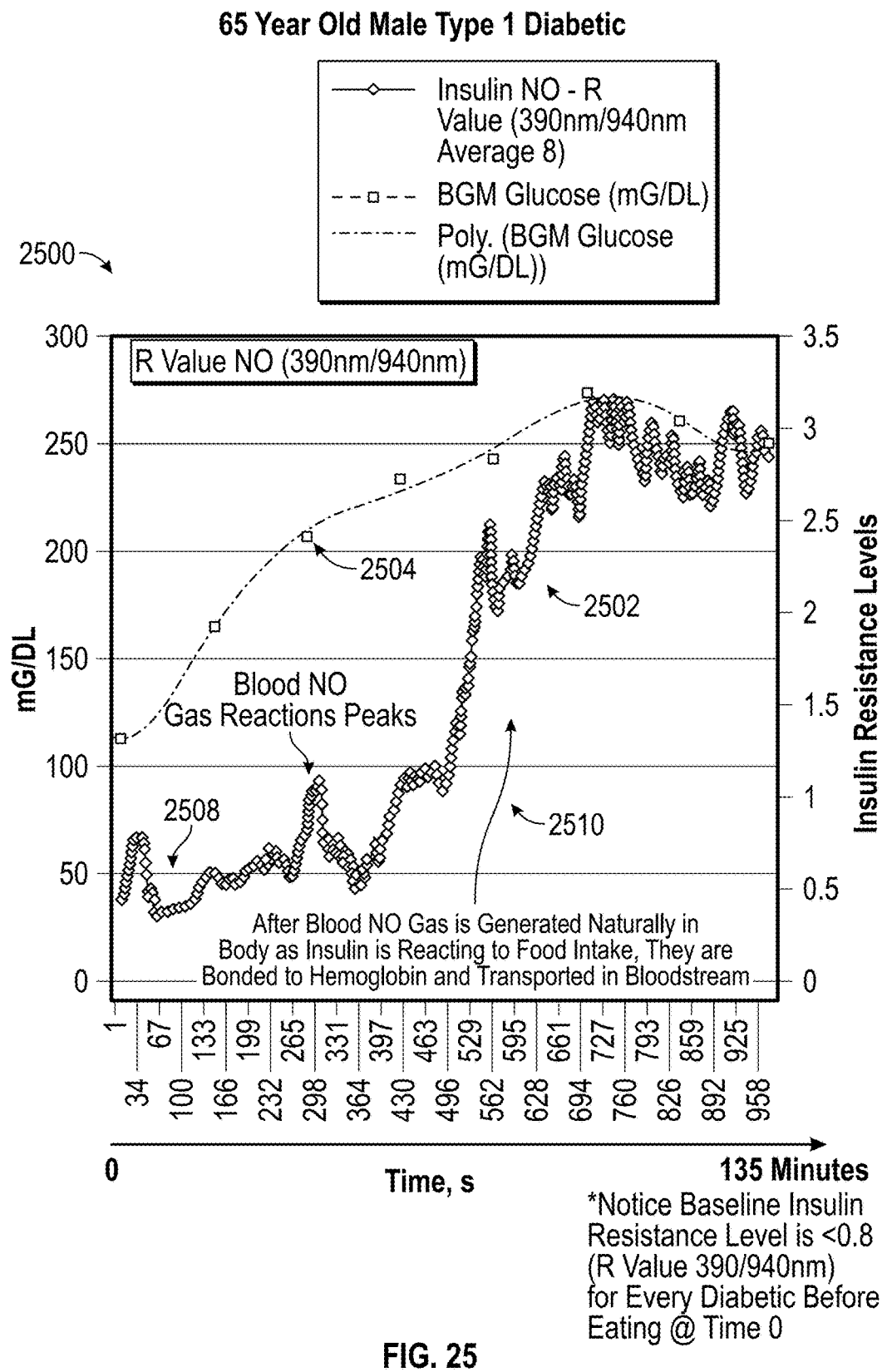
FIG. 25 illustrates a schematic drawing of another exemplary embodiment of results of clinical data obtained using the biosensor from the second patient.

FIG. 25 illustrates a schematic drawing of another exemplary embodiment of results of clinical data 2500 obtained using the biosensor 100 from the second patient. At predetermined time periods of about 15 minutes, blood glucose level (BGL) was measured using a known method and the BGL measurements plotted. The plotted measurements were interpolated to generate a polynomial showing the approximate BGLs 2504 in mg/dl units. The biosensor 100 obtained measurements over the same time period to derive the Ratio R for approximately $L_{390\ nm}/L_{940\ nm}$ 2502, as shown on the graph as well.

In this clinical trial, the R value for $L_{390\ nm}/L_{940\ nm}$ has a low base insulin resistance factor 2504 of less than 1 (in an R value range from 0-8) indicating a diabetic condition in the patient. After consumption of a high sugar substance at around 200 seconds, an insulin response 2510 is seen at approximately 232 seconds. It seems that the $L_{390\ nm}$ is measuring NO levels in the arterial blood flow. As insulin is generated in the body, it reacts with blood vessels to generate NO gas. The NO gas bonds to hemoglobin and is transported in the blood stream. The NO is thus a good indicator of a base insulin resistance factor after fasting and an insulin response after caloric intake.

The ratio R values may also be correlated with blood glucose levels (BGL) using the graph or using a similar table or other correlation method. For example, the ratio R for $L_{390\ nm}/L_{940\ nm}$ with a value of 1.75 is correlated to a BGL of about 150 mG/DL using the graph. The R value for $L_{390\ nm}/L_{940\ nm}$ may thus be used to show a base insulin resistance factor 2508 insulin response 2510 as well as obtain blood glucose levels for the patient.

In addition, nitric oxide NO generation helps hemoglobin in the uptake of oxygen. Thus, the NO measurements, such as the R value for $L_{390\ nm}/L_{940\ nm}$, are also a good indicator of vascular health.

Figure 26:
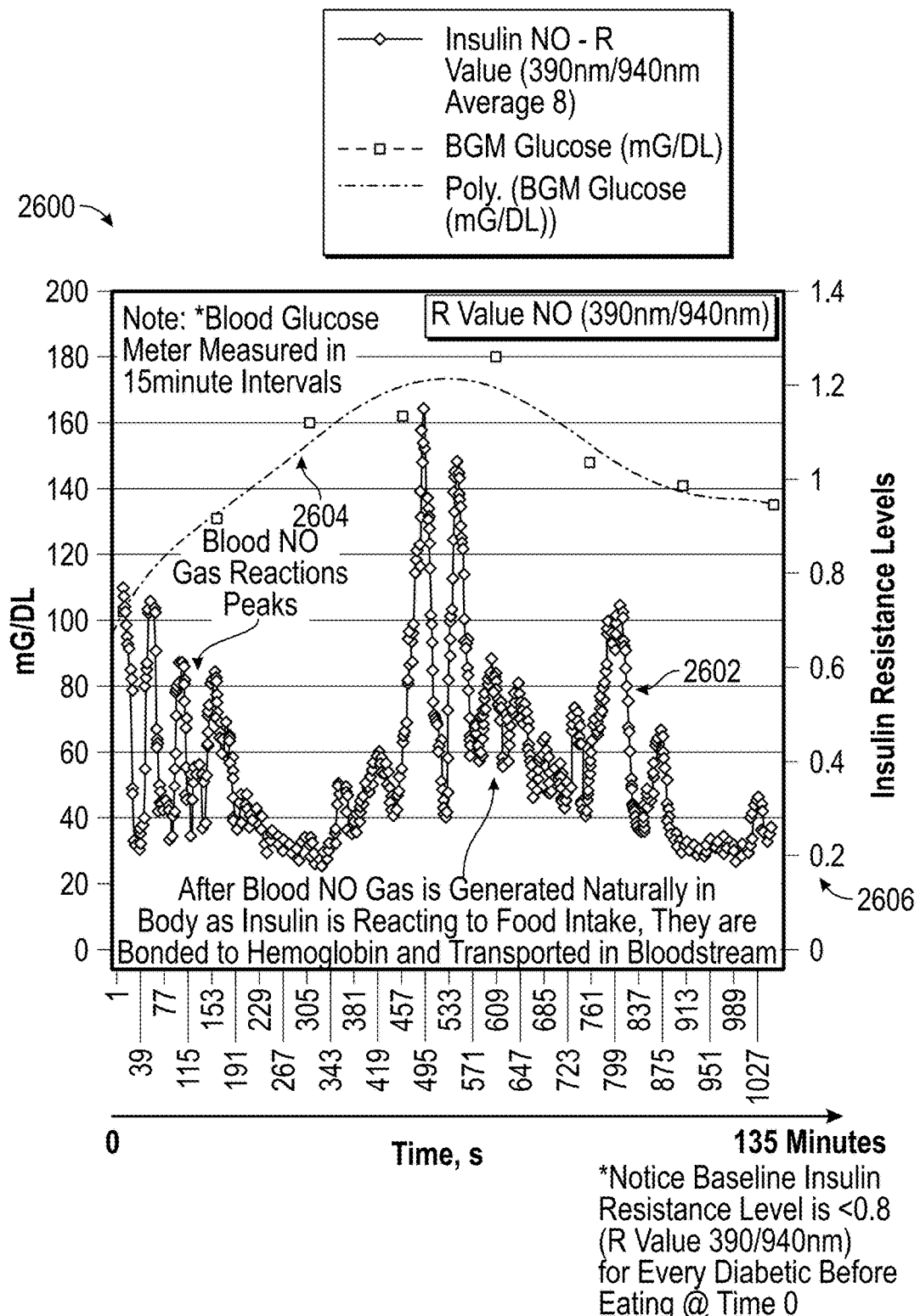
FIG. 26 illustrates a schematic drawing of another exemplary embodiment of results of clinical data obtained using the biosensor from a third patient.

FIG. 26 illustrates a schematic drawing of another exemplary embodiment of results of clinical data 2600 obtained using the biosensor 100 from a third patient. The third patient is a 37 year old female with a known diagnosis of Type 1 diabetes. At predetermined time periods of about 15 minutes, blood glucose levels (BGL) were measured using a known method and the BGL measurements plotted. The plotted measurements were interpolated to generate a polynomial showing the approximate BGL 2604 in mg/dl units. The biosensor 100 obtained measurements over the same time period to derive the Ratio R for approximately $L_{390\ nm}/L_{940\ nm}$ 2602, as shown on the graph as well.

In this clinical trial, the insulin resistance level or R value for $L_{390\ nm}/L_{940\ nm}$ measured prior to eating has a low baseline value of less than 1 indicating a diabetic condition. In unexpected results, the base insulin resistance factor 2606 for the R value at $L_{390\ nm}/L_{940\ nm}$ is seen as less than 0.8. Thus, from unexpected clinical results, it is determined that a base insulin resistance factor or R value for $L_{390\ nm}/L_{940\ nm}$ of less than 1 from an R value range of 0-8 indicates a diabetic condition. After consumption of a high sugar substance, insulin response is seen from 1-191 seconds.

From the clinical trials, it seems that the $L_{390\ nm}$ is measuring NO levels in the arterial blood flow. As insulin is generated in the body, it reacts with blood vessels to generate NO gas. The NO gas bonds to hemoglobin and is transported in the blood stream. The R value for $L_{390\ nm}/L_{940\ nm}$ measures the NO levels in the pulsating arterial blood flow and thus provides a good indicator of BGLs, base insulin resistance factor and insulin response after caloric intake. The BGLs may be obtained from the R values using the graph 2600 or a similar table that correlates the R value with known BGL measurements for the patient.

Figure 27:
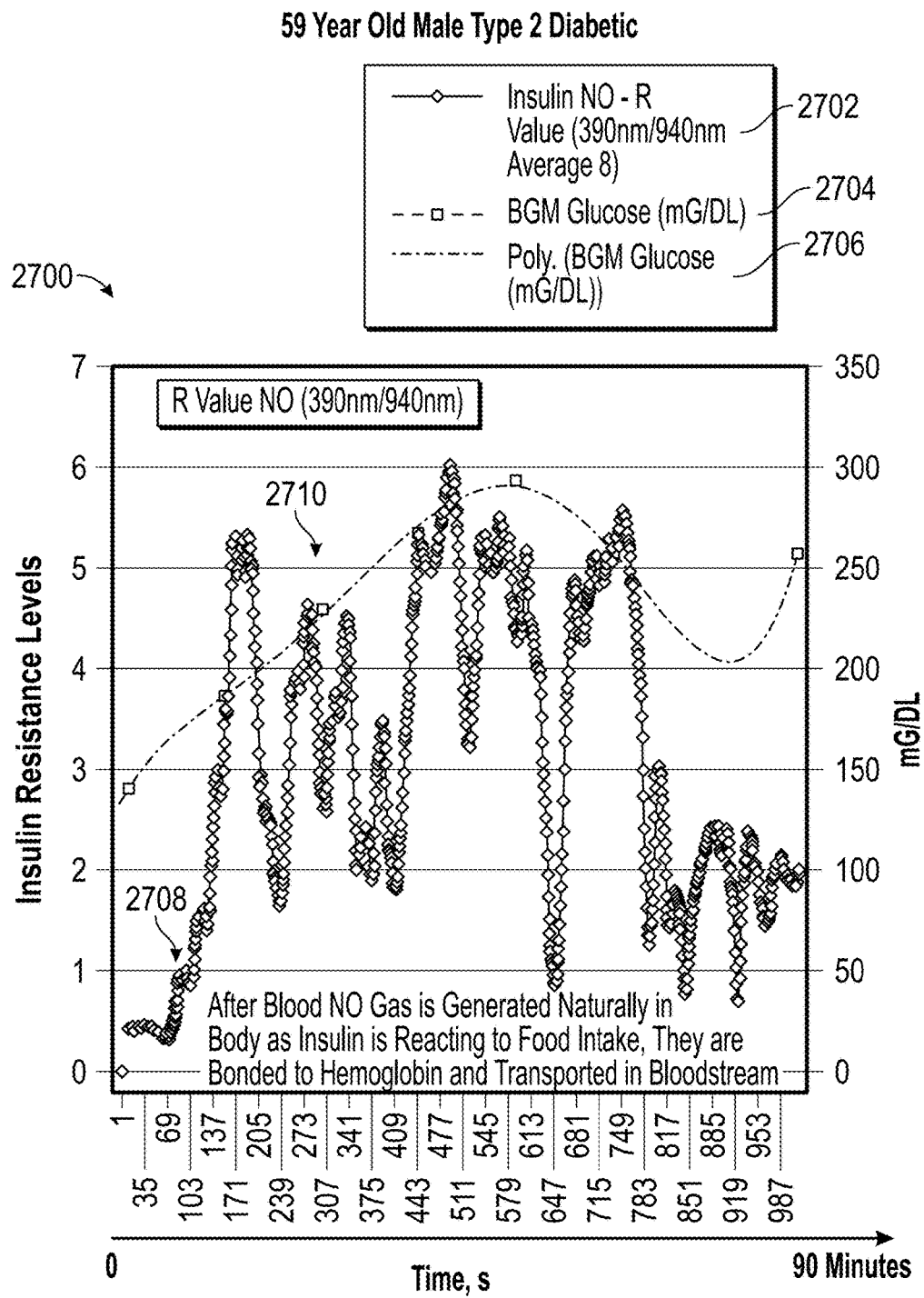
FIG. 27 illustrates a schematic drawing of another exemplary embodiment of results of clinical data obtained using the biosensor from a fourth patient.

FIG. 27 illustrates a schematic drawing of another exemplary embodiment of results of clinical data 2700 obtained using the biosensor 100 from a fourth patient. The fourth patient is a 59 year old male with a known diagnosis of Type 2 diabetes. At predetermined time periods of about 15 minutes, blood glucose level (BGL) was measured using a known method of a blood glucose meter (BGM) using blood from finger pricks. The BGM glucose measurements 2704 are plotted. The plotted measurements were interpolated to generate a polynomial 2706 showing the approximate BGM glucose measurements over time in mG/DL units. The biosensor 100 obtained measurements over the same time period to derive the Ratio R for approximately $L_{390\ nm}/L_{940\ nm}$ 2702, as shown on the graph as well.

In this clinical trial, the base insulin resistance factor 2708 measured prior to eating has a low baseline value of about 0.5 indicating a diabetic condition. In unexpected results, the base insulin resistance factor or R value for $L_{390\ nm}/L_{940\ nm}$ of less than 1 (in an R value range of 0-8) thus seems to indicate a diabetic condition from the clinical trial results. After consumption of a high sugar substance, insulin response 2710 is seen after about 7 minutes. The blood glucose levels may be obtained from the R values using the graph 2700 or a similar calibration table that correlates the R value with known BGL measurements for the patient. The calibration table may be generated for a specific patient or may be generated from a sample of a general population. It is determined that the R values should correlate to similar BGL measurements across a general population. Thus, the calibration table may be generated from testing of a sample of a general population.

From the unexpected results of the clinical trials, an R value of less than 1 (in an R value range of 0-8) indicated that a person has diabetes or early onset of diabetes. An R value of 5 (in an R value range of 0-8) or above indicated that a person has no diabetic condition. For example, as shown in graph 2208, the base insulin resistance factor measured using an R value of approximately $L_{390\ nm}/L_{940\ nm}$ has generally an average value greater than 5 in the first patient without a diabetes diagnosis. The base insulin resistance factor measured using an R value of approximately $L_{390\ nm}/L_{940\ nm}$ was generally an average value less than 1 (in an R value range from 0-8) in the other patients with a diabetes diagnosis of either Type 1 or Type II. The base insulin resistance factor measured using an R value in the 1-2 (in an R value range from 0-8) range indicated a high risk of diabetes and need for further testing.

It seems that the $L_{390\ nm}$ is measuring NO levels in the arterial blood flow. As insulin is generated in the body, it reacts with blood vessels to generate NO gas. The NO gas bonds to hemoglobin and is transported in the blood stream. The NO is thus a good indicator of a base insulin resistance factor after fasting and an insulin response after caloric intake.

From the clinical trials, it seems that the NO levels are reflected in the R values obtained from $L_{390\ nm}/L_{940\ nm}$. Based on the clinical trials and R values obtained in the clinical trials, it is determined that a base insulin resistance factor of less than 1 corresponds to an NO concentration level of at least less than 25% of average NO levels. For example, average NO levels are determined by sampling a general population of persons without diabetes or other health conditions affecting NO levels. From the clinical trials, an R value correlating to a base insulin factor of less than 1 indicates that the NO levels are in a range of 25% to 50% less than average NO levels. After fasting, a person with a diabetic condition will have low NO concentration levels that are at least 25% less than average NO levels due to the low level of insulin in the blood. Thus, an NO concentration level of at least less than 25% of normal ranges of NO concentration levels indicates a diabetic condition (e.g., the NO levels corresponding to R value less than 1 in this clinical trial). Thus, a base insulin resistance factor of less than 1 correlates to at least less than 25% of average NO levels of a sample population and indicates a diabetic condition.

Based on the clinical trials and R values obtained in the clinical trials, it is determined that a base insulin resistance factor in the range of 2-8 corresponds to average NO concentration levels. Thus, a base insulin resistance factor (e.g. in the range of 2-8) correlates to an average NO level of a sample population and little to no diabetic risk.

Based on these unexpected results, in one aspect, the biosensor 100 may display or transmit, e.g. to a user device or monitoring station, or otherwise output an indicator of the diabetic risk of a patient based on the R value. For example, the biosensor 100 may output no diabetic risk based on an obtained R value for a patient of 5 or greater. In another aspect, the biosensor 100 may output low diabetic risk based on an obtained R value of 2-5. In another aspect, the biosensor 100 may output high diabetic risk based on an obtained R values of 1-2. In another aspect, the bio sensor 100 may output diabetic condition detected based on an R value less than one. In the clinical trials herein, the R value was in a range of 0-8. Other ranges, weights or functions derived using the R value described herein may be implemented that changes the numerical value of the R values described herein or the range of the R values described herein. In general, from the results obtained herein, an R value corresponding to at least the lower 10% of the R value range indicates a diabetic condition, an R value in the lower 10% to 25% of the R value range indicates a high risk of diabetes, an R value in the 25% to 60% range indicates a low risk of diabetes, and an R value greater than 60% indicates no diabetic condition.

The R value of $L_{390\ nm}/L_{940\ nm}$ may be non-invasively and quickly and easily obtained using the biosensor 100 in a physician's office or other clinical setting or at home. In one aspect, the R value may be used to determine whether further testing for diabetes needs to be performed. For example, upon detection of a low R value of less than 1, a clinician may then determine to perform further testing and monitoring, e.g. using glucose ingestion tests over a longer period of time or using the biosensor 100 over a longer period of time or other type of testing.

Embodiment—Digestive Stage and Caloric Intake Measurements

Figure 28:
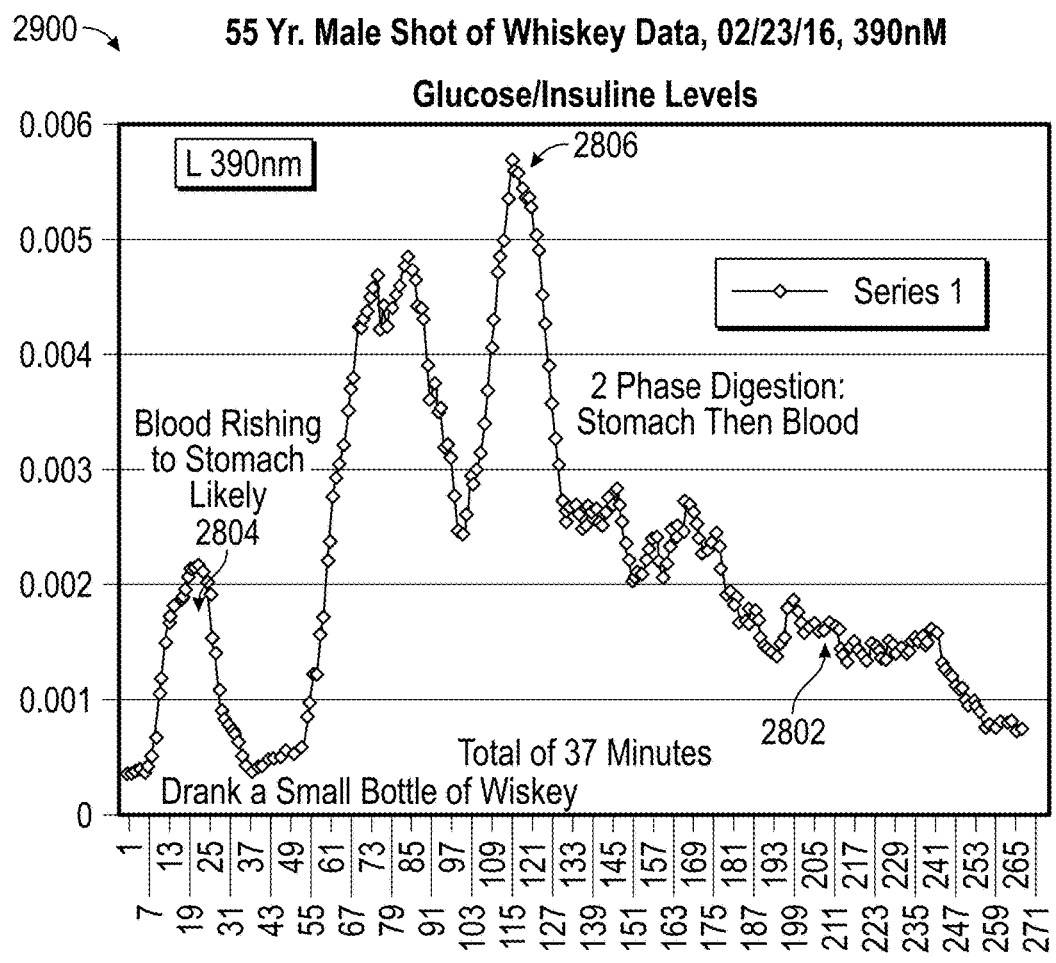
FIG. 28 illustrates a schematic drawing of another exemplary embodiment of results of clinical data obtained using the biosensor from a fifth patient.

FIG. 28 illustrates a schematic drawing of another exemplary embodiment of results of clinical data 2800 obtained using the biosensor 100 from the fifth patient. In this trial, the fifth patient ingested whiskey at approximately 13 seconds. The biosensor 100 was used to measure the digestive stages over a measurement period of approximately 37 minutes using a wavelength of approximately 390 nm to track the blood glucose levels. The graph illustrates the values for $L_{390\ nm}$ 2802 obtained over the measurement period. The biosensor 100 was able to detect the digestive stage 1 2904 and digestive stage 2 2806 based on the obtained values for $L_{390\ nm}$. The first digestive stage 1 2804 is indicated by an initial spike around 20 seconds as blood rushes to the stomach to aid in digestion. The second digestive stage 2 is indicated by a later, more prolonged increase in blood glucose levels between 60 and 180 seconds.

Based on the insulin response and BGL measurements, a calibration of caloric intake may be performed for a patient. For example, known caloric intakes may be correlated with insulin response in phase 1 and phase 2 digestions measured using values for $L_{390\ nm}$ 2902. In another aspect, the calibration table may be generated using testing of a sample of a general population. It is determined that the R values using $L_{390\ nm}$ 2902 should correlate to similar caloric intake measurements across a general population. Thus, the calibration table may be generated from testing of a sample of a general population.

Figure 29:
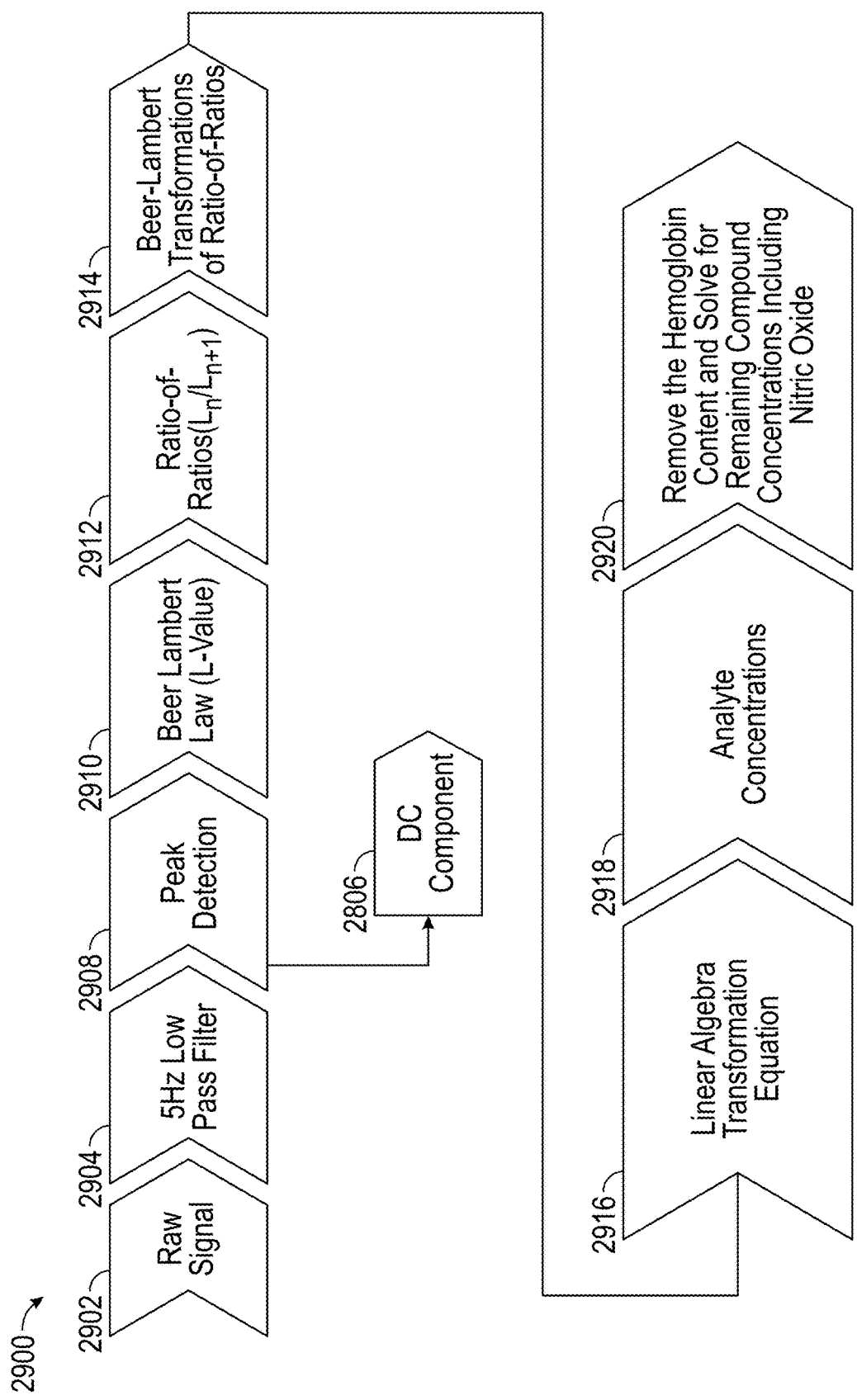
FIG. 29 illustrates a schematic block diagram of an embodiment of a method for determining concentration levels or indicators of substances in pulsating blood flow in more detail.

FIG. 29 illustrates a schematic block diagram of an embodiment of a method 2900 for determining concentration levels or indicators of substances in pulsating blood flow in more detail. The biosensor 100 obtains a spectral response signal at a first wavelength and at a second wavelength at 2902. The spectral response signal includes AC and DC components IAC+DC. A low pass filter is applied to the spectral response signal IAC+DC to isolate the DC component 2906 of the spectral response signal at each wavelength at 2904. The AC fluctuation is due to the pulsatile expansion of the arteriolar bed due to the volume increase in arterial blood. In order to measure the AC fluctuation, measurements are taken at different times and a peak detection algorithm or other means is used to determine the diastolic point and the systolic point of the spectral response at 2908. The systolic and diastolic measurements are compared in order to compute the L values using Beer-Lambert equations at 2910. For example, a logarithmic function may be applied to the ratio of IAC+DC and IDC to obtain an L value for the first wavelength Lλ1 and for the second wavelength Lλ2. The ratio R of the first wavelength Lλ1 and for the second wavelength Lλ2 may then be calculated at 2912. When multiple frequencies are used to determine a concentration level of one or more substances, the the linear function described herein are applied at 2916, and the one or more concentration levels of the substances or analytes are determined at 2918.

In an embodiment, a substances or analyte may be attached in the blood stream to one or more hemoglobin compounds. The concentration level of the hemoglobin compounds may then need to be subtracted from the concentration level of the substance determined at 2918 to isolate the concentration level of the substance at 2920 from the hemoglobin compounds. For example, nitric oxide (NO) is found in the blood stream in a gaseous form and also attached to hemoglobin compounds. Thus, the measurements at L390 nm to detect nitric oxide may include a concentration level of the hemoglobin compounds as well as nitric oxide. The hemoglobin compound concentration levels may then be determined and subtracted to isolate the nitric oxide concentration levels. This process is discussed in more detail with respect to FIG. 32 below.

Figure 30:
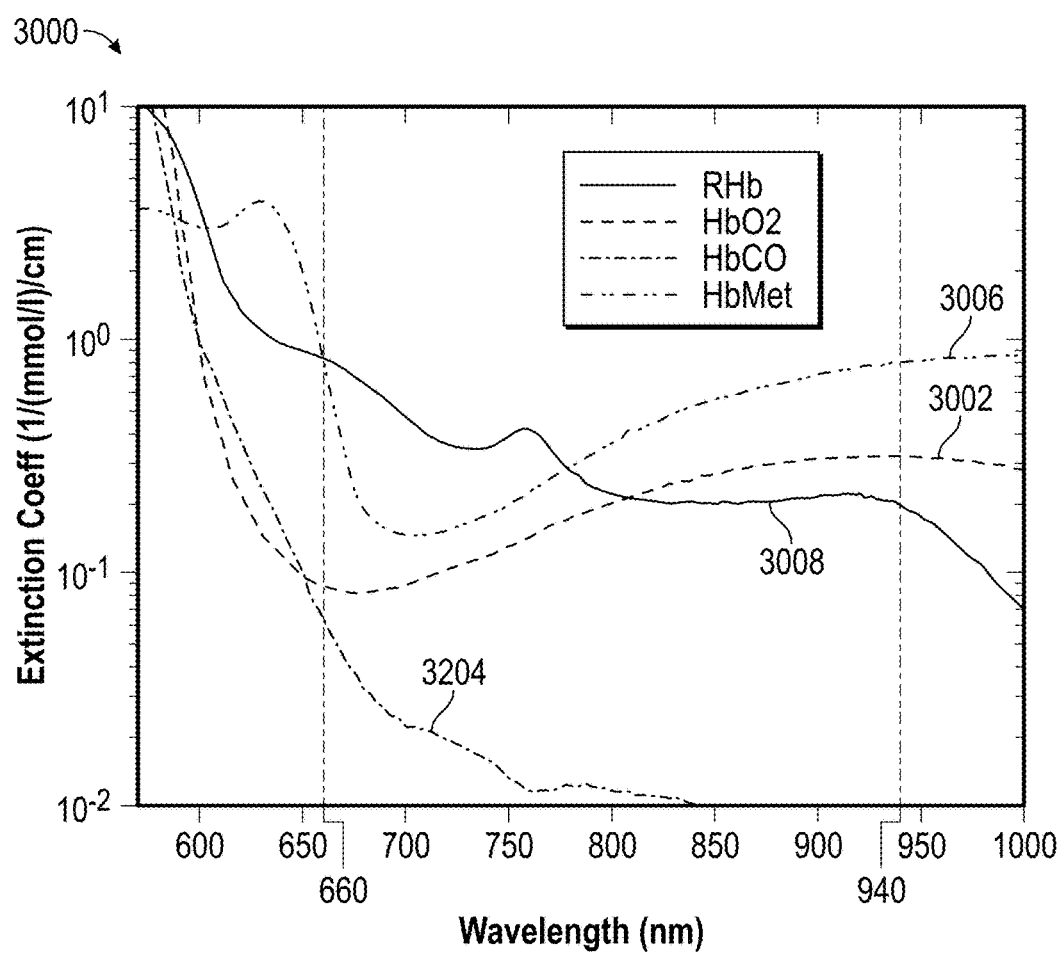
FIG. 30 illustrates a schematic block diagram of an exemplary embodiment of a graph illustrating the extinction coefficients over a range of frequencies for a plurality of hemoglobin compounds.

FIG. 30 illustrates a schematic block diagram of an exemplary embodiment of a graph 3000 illustrating the extinction coefficients over a range of frequencies for a plurality of hemoglobin compounds. The hemoglobin compounds include, e.g., Oxyhemoglobin [HbO2] 3002, Carboxyhemoglobin [HbCO] 3004, Methemoglobin [HbMet] 3006, and reduced hemoglobin fractions [RHb] 3008. As seen in FIG. 30, the biosensor 100 may control the PPG circuit 110 to detect the total concentration of the hemoglobin compounds using a center frequency of 660 nm and a range of 1 nm to 50 nm. A method for determining the relative concentration or composition of different kinds of hemoglobin contained in blood is described in more detail in U.S. Pat. No. 6,104,938 issued on Aug. 15, 2000, which is hereby incorporated by reference herein.

Though the above description includes details with respect to pulsating arterial blood flow, the biosensor 100 may use similar techniques described herein for pulsating venous blood flow. The biosensor 100 is positioned on skin tissue over veins, such as on the wrist, and spectral responses obtained from light reflected by or transmitted through the pulsating venous blood flow.

Embodiment—Measurement of Blood Alcohol Level

The biosensor 100 may be configured to detect blood alcohol level in blood flow using one or more methods. For example, the biosensor 100 may be configured to obtain an indicator of a concentration level of one or more alcohol enzymes which convert alcohol to acetaldehyde in the blood stream. In another embodiment, the biosensor 100 may be configured to detect an indicator of a concentration level of a liver enzyme, such as P450 or NAD+ or NADH or another ADH related enzyme, which is released in response to alcohol in the blood stream. In another embodiment, the biosensor 100 is configured to detect ethanol in blood flow. These methods are described in more detail hereinbelow.

Figure 31:
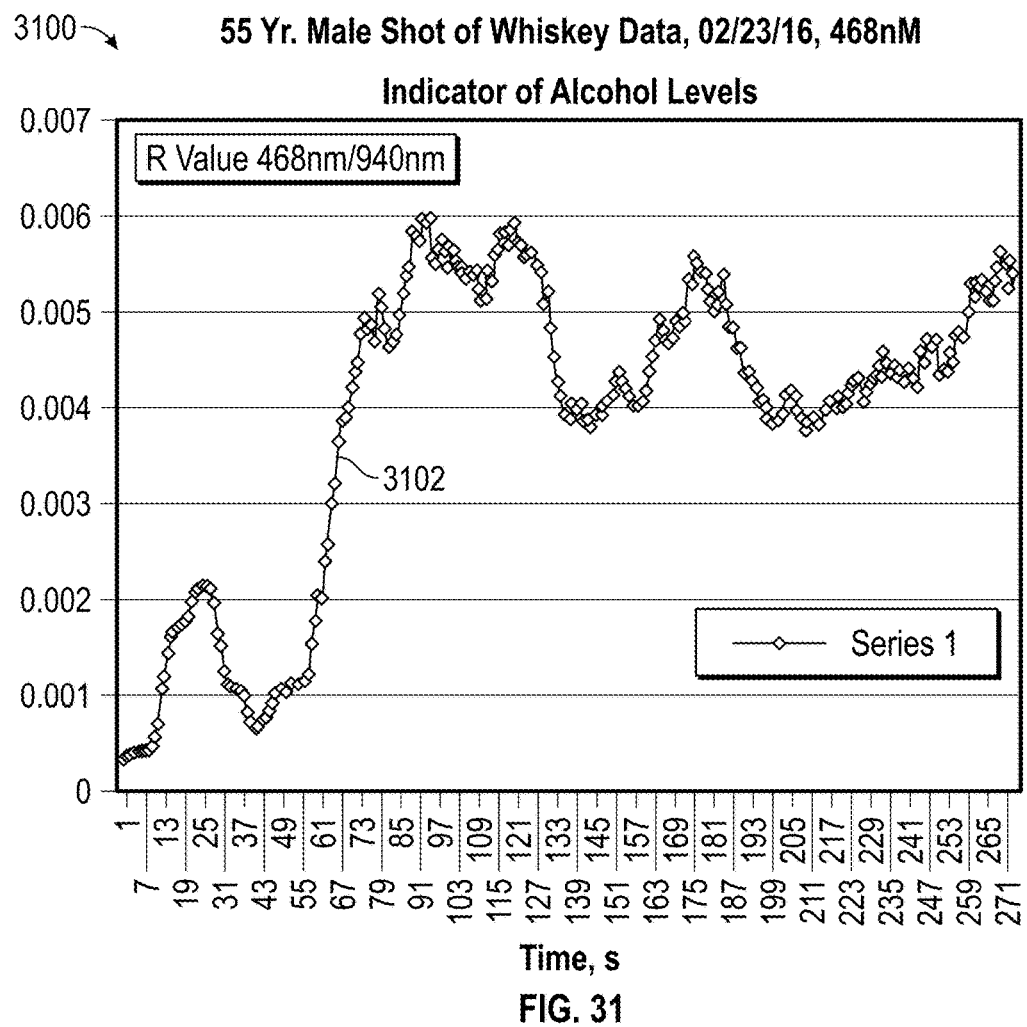
FIG. 31 illustrates a schematic drawing of another exemplary embodiment of results of clinical data obtained using the biosensor from the fifth patient.

FIG. 31 illustrates a schematic drawing of another exemplary embodiment of results of clinical data 3100 obtained using the biosensor 100 from a fifth patient. In this trial, the fifth patient was a 55 year old male that ingested a shot of whiskey at approximately 7 seconds. The biosensor 100 was used to measure an indicator of blood alcohol levels over a measurement period of approximately 271 seconds. The biosensor 100 obtained spectral responses reflected from the skin of the patient around a first wavelength of approximately 468 nm and around a second wavelength of approximately 940 nm. The graph illustrates the values obtained for the $R = L_{468\ nm}/L_{940\ nm}$ ratio 3102 over the measurement period.

Using the $R_{468,940}$ ratio 3102, the biosensor 100 could detect the increase in the blood alcohol levels over the measurement period. The values for the $R_{468,940}$ ratio 3102 may be correlated with blood alcohol levels. For example, a correlation may be determined by testing blood alcohol levels at preset intervals (such as every 1-5 minutes) during a measurement period (such as 1-5 hours) using known measurements, such as a blood draw or breathalyzer. The $R_{468,940}$ ratio 3102 is also determined for the preset intervals during the measurement period. The blood alcohol measurements are then correlated with the measured values for the $R_{468,940}$ ratio 3102 over the same measurement period.

In general, the values of the $R_{468,940}$ ratio 3102 are consistent with an approximate measured blood alcohol level in subsequent clinical trials for a patient. The correlation of measured blood alcohol levels to values of the $R_{468,940}$ ratio 3102 may only be performed once for a patient. In another aspect, the calibration table may be generated by testing a sample general population. It is determined that the values of the $R_{468,940}$ ratio 3102 correlate to similar blood alcohol measurements across a general population. Thus, the calibration table may be generated from testing of a sample general population.

Figure 32:
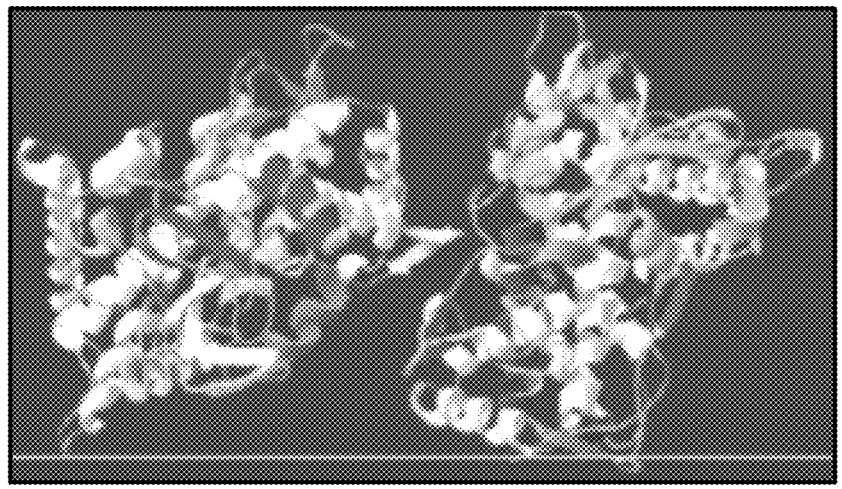
FIG. 32 illustrates a schematic drawing of an exemplary embodiment of a liver enzyme for measuring a blood alcohol level.
Figure 32:
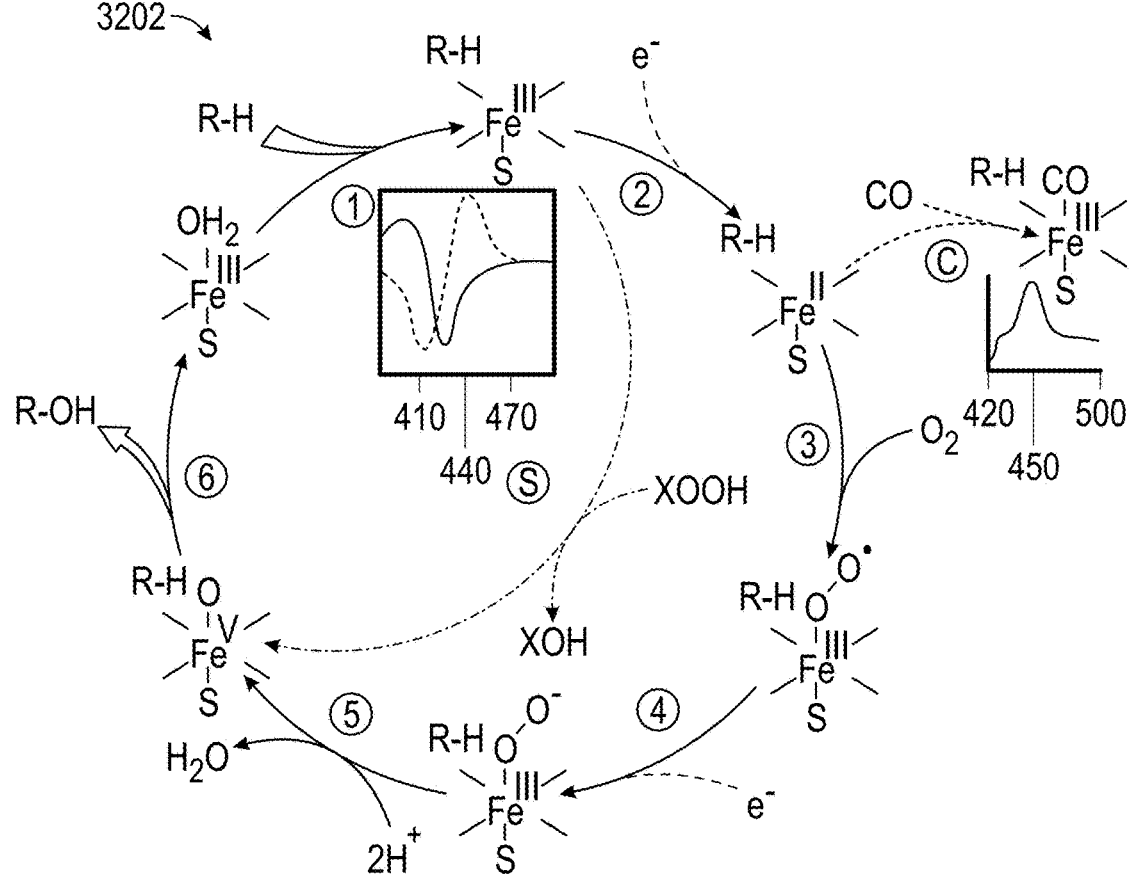

FIG. 32 illustrates a schematic drawing of an exemplary embodiment of a liver enzyme for measuring a blood alcohol level. In unexpected results, the $R_{468,940}$ ratio 3102 seems to be measuring a liver enzyme called cytochrome P450 Oxidase (P450) 3200. In one aspect, a spectral response around a wavelength at approximately 468 nm was used by the biosensor 100 to obtain L values that tracked the concentration levels of the liver enzyme P450 3200. The liver enzyme reacts with various substances 3202 and is generated in response to blood alcohol levels. Recent studies have shown that Cytochrome P450 increases in ethanol oxidation as blood alcohol concentrations increase in blood flow. Thus, the concentration of P450 is correlated with the concentration of blood alcohol in blood flow.

The measurement of the spectral response for the wavelength at approximately 468 nm may be used to indicate blood alcohol levels and/or concentration levels of the liver enzyme P450 3200. For example, a calibration table would include a graph, table, or other means to correlate blood alcohol levels with values for the $R_{468/940}$ ratio 3102. The biosensor 100 may then determine a blood alcohol level using a measured value for the $R_{468/940}$ ratio 3102 and the calibration table.

Three enzymes are known to break down alcohol to acetaldehyde in the body and include: alcohol dehydrogenase (ADH), cytochrome P450 (CYP2E1) and catalase. During the break down of alcohol, hydrogen atoms are stripped from the alcohol molecule to form acetaldehyde. These three enzymes are each found in different parts of the body and each of them reacts to the hydrogen atoms that are stripped from the alcohol molecule in a different way. For example, alcohol dehydrogenase is the workhorse of the alcohol enzymes—it breaks down the majority of the alcohol that enters the human body. Alcohol dehydrogenase is actually the name for a family of enzymes which break down alcohol—each of which has a slightly different molecular structure. Researchers have identified as many as 10 varieties of the alcohol dehydrogenase molecule. All of them bring about the same chemical reaction—the difference is that some varieties of alcohol dehydrogenase work more efficiently than others. These variations in the alcohol dehydrogenase (ADH) molecule may explain why some individuals react differently to alcohol than others.

The alcohol dehydrogenase molecules do their work primarily in the stomach and the liver, although traces of them are found in other tissues as well. When alcohol dehydrogenase turns alcohol into acetaldehyde, hydrogen is released and is bound to a compound called Nicotinamide Adenine Dinucleotide (NAD+) to form Nicotinamide Adenine Dinucleotide plus Hydrogen (NADH). The biosensor 100 may be configured to detect an indicator of a concentration level of an ADH related enzyme such as NADH to obtain a blood alcohol level.

Figure 33:
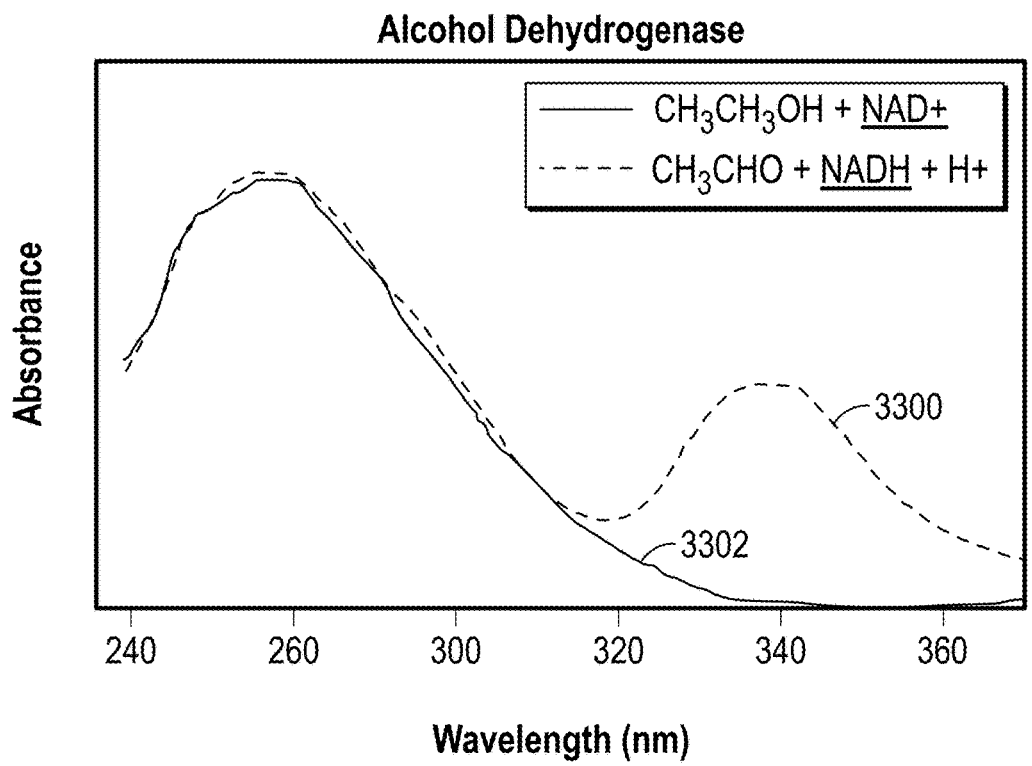
FIG. 33 illustrates a schematic drawing of an exemplary embodiment of using the biosensor for measurements of an indicator of a concentration level of NADH.

FIG. 33 illustrates a schematic drawing of an exemplary embodiment of using the biosensor 100 for measurements of an indicator of a concentration level of NADH. It has been found that the molecule NADH has an absorbance coefficient 3300 that is greatest around approximately 340 nm while the molecule NAD+ has an absorbance coefficient 3302 that is low around 340 nm. The PPG circuit 110 may obtain a plurality of spectral responses from light reflected or transmitted through skin around 340 nm or in ranges around 340 nm (such +/−15 nm) and obtain a R ratio $R = L_{340\ nm}/L_{940\ nm}$. Though 940 nm is described herein, other wavelengths may be utilized with a low absorbance coefficient for NADH.

The biosensor 100 obtains values for the $R_{340/940}$ ratio as an indicator of a concentration level of NADH. The values for the $R_{340/940}$ ratio may then be correlated with known blood alcohol levels, e.g. using a sample general population, to generate a calibration table. The calibration table would include a graph, table, or other means to correlate blood alcohol levels with values for the $R_{340/940}$ ratio. The biosensor 100 may then determine a blood alcohol level of a user using a measured value for the $R_{340/940}$ ratio from the user and the calibration table. Though measurement of a level of NADH is described herein, the biosensor 100 may be configured to measure other enzyme alcohol dehydrogenase (ADH) derivatives, such as alcohol dehydrogenase (ADH) or related NADH enzyme.

Figure 34:
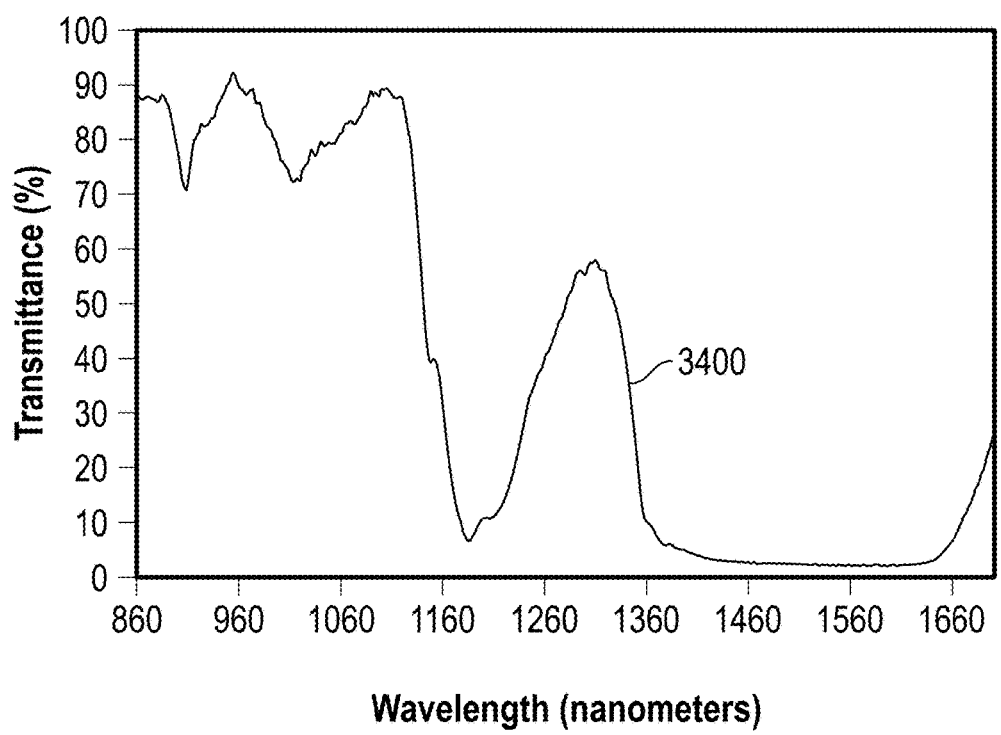
FIG. 34 illustrates a schematic drawing of an exemplary embodiment of using an embodiment of the biosensor for measurements of an indicator of a concentration level of ethanol.

FIG. 34 illustrates a schematic drawing of an exemplary embodiment of using the biosensor 100 for measurements of an indicator of a concentration level of ethanol. As seen in FIG. 3, the highest peaks of the transmittance percentage graph 3400 are around 1050 nm for ethanol. It has been found that ethanol has an absorbance coefficient 3400 that is greatest around approximately 1050 nm or in ranges approximately +/−15 nm around 1050 nm. The transmittance percentage of ethanol may be expressed in absorbance as well.

The PPG circuit 110 may obtain a plurality of spectral responses from light reflected or transmitted through skin around 1050 nm or in ranges around 1050 nm (such +/−15 nm) and obtain a R ratio value $R = L_{1050\ nm}/L_{940\ nm}$. Though 940 nm is shown herein, other wavelengths may be utilized with a low absorbance coefficient for ethanol.

The biosensor 100 obtains values for the $R_{1050/940}$ ratio as an indicator of a concentration level of ethanol. The values for the $R_{1050/940}$ ratio may then be correlated with known blood alcohol levels, e.g. using a sample general population, to generate a calibration table. The calibration table would include a graph, table, or other means to correlate blood alcohol levels with values for the $R_{1050/940}$ ratio. The biosensor 100 may then determine a blood alcohol level of a user using a measured value for the $R_{1050/940}$ ratio from the user and the calibration table.

The biosensor 100 is thus configured to obtain a concentration level of blood alcohol using one or more methods, e.g., using an indicator of a level of P450, NADH (or other ADH related enzyme), ethanol or any combination thereof. For example, the biosensor 100 may determine indicators of levels of a plurality of substances, e.g. any combination of P450 or ethanol or NADH or other alcohol dehydrogenase (ADH) derivative.

The biosensor 100 may then determine a blood alcohol level using the plurality of indicators. For example, the biosensor 100 may determine a first blood alcohol level using an indicator of P450 levels and a second blood alcohol level using an indicator of NADH levels. The biosensor 100 may then use an average or mean of the first and second blood alcohol levels to determine a final blood alcohol level. In another example, the biosensor 100 may determine blood alcohol levels using an indicator of NADH levels obtained over a period of time or sample window. The biosensor may then average the blood alcohol levels obtained over the sample window to determine an output blood alcohol level. Other methods may also be used to determine a concentration level of blood alcohol using one or more methods, such as from an indicator of a level of P450, NADH, ethanol or another substance related to a concentration level of blood alcohol levels.

Embodiment—Detection of an Infection

The biosensor 100 may be configured to provide a warning of a risk of an infection or sepsis. The biosensor 100 may also detect temperature as well as other vital signs indicative of an infection or sepsis, such as pulse rate and respiration rate. In another aspect, the PPG circuit 110 may detect white blood cell counts to determine a presence of an infection.

In another embodiment, the biosensor 100 detects NO levels in vivo in the blood stream of a patient to determine the risk of an infection or sepsis. It has been shown that elevated levels of NO are indicative of an infection and sepsis. For example, a baseline of an NO concentration level in blood vessels is obtained. For example, the NO concentration level may be obtained from an R value using $L_{\lambda 1}$=390 nm and $L_{\lambda 2}$=940 nm or an R value at $L_{\lambda 1}$=395 nm and $L_{\lambda 2}$=660 nm. In another embodiment, the NO measurement may be obtained using a value of $L_{\lambda 1}$=380 nm-400 nm and $L_{\lambda 2}$>660 nm. The spectral response used to determine the value of $L_{\lambda 1}$=380 nm-400 nm may also be measuring other NO compounds or isoforms such as eNOS or iNOS or nNOS or other compounds bonded to a plurality of hemoglobin species. The concentration of the plurality of hemoglobin species may be adjusted from the NO measurements and a calibration database used to obtain an NO concentration level. In another example, the biosensor 100 may determine the relative shift in the absorbance spectra for a substance (such as hemoglobin) and access a calibration database that correlates the relative shift in the absorbance spectra of the substance with a concentration level of NO.

The biosensor 100 displays the baseline NO measurement and then non-invasively and continuously monitors the NO measurement in blood vessels. For example, the biosensor 100 may obtain the NO measurement at least once per minute or more frequently, such as every 10 seconds or 30 seconds, and continues to display the NO measurement. The biosensor 100 may also monitor other patient vitals indicative of sepsis condition, such as temperature, pulse, and respiration rate.

The NO measurement is compared to a first predetermined threshold. For example, normal ranges of the NO measurement from the baseline measurement are determined for septic risk. Patient vitals may also be compared to predetermined thresholds. Depending on the comparison, one or more warnings are displayed. For example, the first predetermined threshold may be set around 10% above a baseline level of NO. A warning is displayed to indicate a health alert or risk of infection. When the NO measurement equals or exceeds at least 30% of a baseline level of the NO measurement, a warning to indicate a medical emergency may be generated. Due to the immediate danger of such high levels of NO measurement and dangers of septic shock, a request for immediate emergency treatment may be indicated. Though 10% and 30% are illustrated in this example, other percentages over the baseline level may also trigger warnings or alerts.

Embodiment—Measurements of other Substances in Blood Flow

Using similar principles described herein, the biosensor 100 may measure concentration levels or indicators of other substances in pulsating blood flow. For example, using the process 1500 described with respect to FIG. 15, absorption coefficients for one or more frequencies that have an intensity level responsive to concentration level of substance may be determined. The biosensor 100 may then detect the substance at the determined one or more frequencies as described herein and determine the concentration levels using the Beer-Lambert principles and the absorption coefficients. The L values and R values may be calculated based on the obtained spectral response. In one aspect, the biosensor 100 may detect various electrolyte concentration levels or blood analyte levels, such as bilirubin and sodium and potassium. In another aspect, the biosensor 100 may detect sodium NACL concentration levels in the blood flow to determine dehydration. In yet another aspect, the biosensor 100 may be configured to detect proteins or abnormal cells or other elements or compounds associated with cancer.

Embodiment—Detection of Blood Type

Determination of blood groups is a vital factor for overall healthcare needs. The human race by nature has any one of the blood groups namely A, B, AB and O. The blood group "AB" is called the "Universal acceptor" and the people with the "0" group are called "Universal donors". During blood transfusion any mismatch can lead to great harm or possible the death of a person. Hence it is very important for every person to identify his/her blood group.

There is no quick, non-invasive method to determine a patient's blood group. Known blood grouping methods are often a manual process with large & expensive equipment. Within a hospital or blood bank center, a number of blood samples have to be identified within a short span of time. The manual process is a laborious and time-consuming. Thus, there is a need for a quick, convenient and non-invasive method to determine a blood group of a patient, either human or animal.

The biosensor 100 described herein may be configured to assess the blood group of a patient using the PPG circuit 110. Blood type is represented by the ABO and Rh(D) systems. The A, B, O, AB blood type of a person depends on the presence or absence of two genes, A and B. These genes determine the configuration of the red blood cell surface. A person who has two A genes has red blood cells of type A. A person who has two B genes has red cells of type B. If the person has one A and one B gene, the red cells are type AB. If the person has neither the A nor the B gene, the red cells are type O. It is essential to match the ABO status of both donor and recipient in blood transfusions and organ transplants. In addition to the four main blood groups—A, B, AB and O, each group can either be RhD positive or RhD negative. Antigens are proteins on the surface of blood cells that can cause a response from the immune system. The Rh factor is a type of protein on the surface of red blood cells. Most people who have the Rh factor are Rh-positive. Those who do not have the Rh factor are Rh-negative. This means that in total there are eight main blood groups.

The blood type is a immunoreactive feature of the red blood cells (RBCs) that is determined by the antigenic moieties of sugar chains on the RBC surface. In the last 30 years fully automated blood testing instruments have been developed and are in operation at blood centers and major hospitals. These instruments have advantages like high speed and sensitivity but they also require large size and high costs. These are major drawbacks. Development of a portable, low-cost, and sensitive instrument for blood typing is therefore required to make an on-site blood testing feasible.

Agglutination of RBCs (hemagglutination) is caused by an immune reaction between the RBCs and antibodies against the corresponding blood type. In conventional blood typing methods, hemagglutination caused by antibodies is detected by human eyes or by imaging techniques. Alternative methods of blood types using optical techniques have also been reported.

The optical properties of the different blood groups can be detected. The red blood cells comprise about 45% of the human blood. The color differences between the different blood groups is visible. Thus, the optical differences between the different RBC groups (A,B, AB and O) can be established. The spectral differences of the antigens present allow for several methods to be developed to determine the basic blood grouping using a multi-wavelength PPG circuit 110. For example, in the Armenian Journal of Physics, 2011, vol. 4, issue 3 pp. 165-168 shows a method using Blood grouping detection using fiber optics. The basic premise of the method described is to use a laser operating at 820 nm to fire a series of pulses into a blood sample at 10 Khz, then using a photo diode, convert the optical variations back into electrical variations by amplifying, filtering, rectifying and feed the primary signal into a capacitor filter. This capacitor changes a voltage which is different for various blood groups. Since the different blood types have different optical spectrum characteristics, this method of fiber optic injection into a blood sample and then reading the approximate integration response of the corresponding signal shows a basic mathematical integration method is possible. However this method requires a raw blood sample and is expensive and time consuming.

Since the different blood groups have different optical spectrums due to variances in the antigen groups, the PPG circuit 110 described herein may be used to measure the spectral response of blood flow using multiple wavelengths and comparing the R values between them to estimate a particular blood group. The various R values indicate a presence of an antigen to identify a blood group of A, B, O or AB using the plurality of spectral responses. The PPG circuit may use the same R values or different R values to determine a presence of another antigen within a blood group to identify an RH factor using the plurality of spectral responses.

In an embodiment, the PPG circuit emits a series of pulses at a patient's tissue to obtain a series of R values. The series or average of the series of R values is used to identify a blood grouping or antigen group. The PPG circuit 110 uses a series of pulses firing LED's at a rate of between 100-200 Hz to obtain a good heart rate signal. One or more of the following R values for 550/940 nm, 660/940 nm, and 880 nm/940 nm frequencies may be obtained over an integration of a series of heartbeats. Due to the division of the L values, the R value eliminates the input from the skin tissue and non-pulsating blood flow to isolate the input from the pulsating blood flow (venous or arterial). To determine a blood group, the R values may be obtained over a sample window, such as over a plurality of heartbeats. A blood group indicator may be derived from the values of the R ratio over the sample window. For example, an integration of the R values over the sample window may be determined and then the integrated R values used as the blood group indicator. The blood group indicator is then used to identify a blood group from one or more blood group reference tables.

For example, in order to enhance the data signal of a spectral response, the data signal in a spectral response over a series of heart beats is used for the sample window. The R value may be obtained over the sample window using spectral responses around a plurality of frequencies. The frequencies may include, e.g., 550, 660 and 880 nm frequencies or in ranges of wavelengths around such frequencies. In one embodiment, the frequencies include 530 and 590 nm and values for the ratio $R=L_{530}/L_{940}$ and $R=L_{590}/L_{940}$ are determined over the sample window. The values for the first $R_{530/940}$ ratio are then integrated across the sample window to determine an integrated R value as a first blood group indicator. The values for the second $R_{590/940}$ ratio are then integrated across the sample window to determine an integrated R value as a second blood group indicator. A simple integration algorithm for each individual frequency may be implemented to obtain the blood group indicators. In another embodiment, the values for the R ratios are averaged over the sample window. Other functions using the values of the R ratios over the sample window may be implemented to obtain one or more blood group indicators.

The obtained one or more blood group indicators are then used with a calibration table to identify a blood group of the patient, human or animal. For example, the calibration table includes a correlation of values or ranges of the one or more blood group indicators to blood group or blood type. The calibration table may be determined by obtaining the blood group indicator for a sample general population for each known blood type.

Figure 35A:
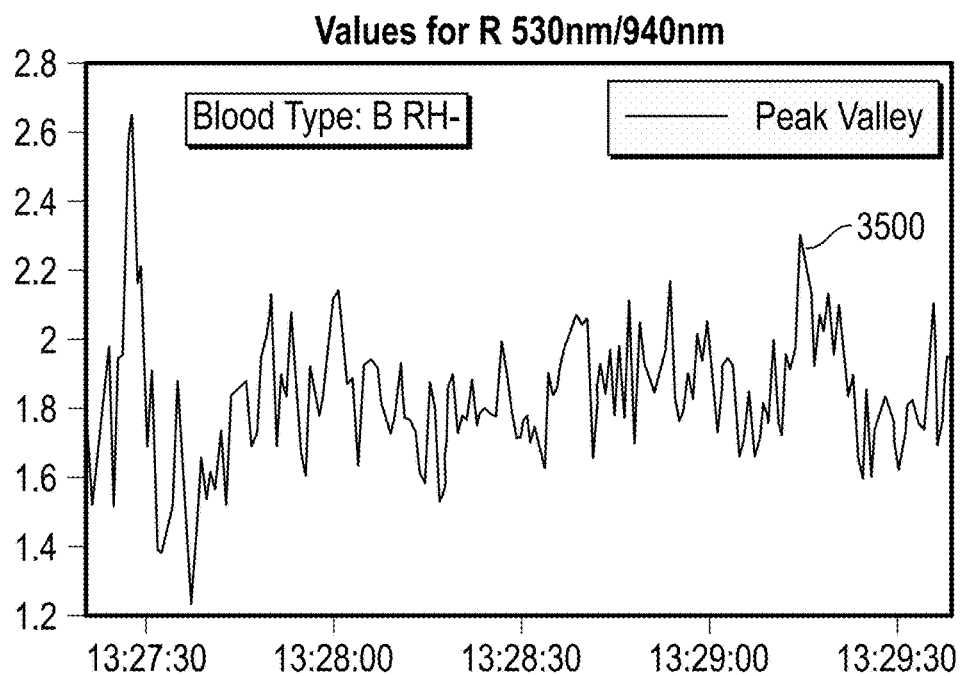
FIG. 35A illustrates a schematic drawing of values for the $R_{530/940}$ ratio obtained using an embodiment of the biosensor.

FIG. 35A illustrates a schematic drawing of values for the $R_{530/940}$ ratio 3500 obtained using the biosensor 100. The biosensor 100 obtained values for the $R_{530/940}$ ratio 3500 over a sample window of approximately two minutes. In this embodiment, it was known that the patient had a blood type of B RH−. An average of the values for the $R_{530/940}$ ratio 3500 over the sample window was obtained.

Figure 35B:
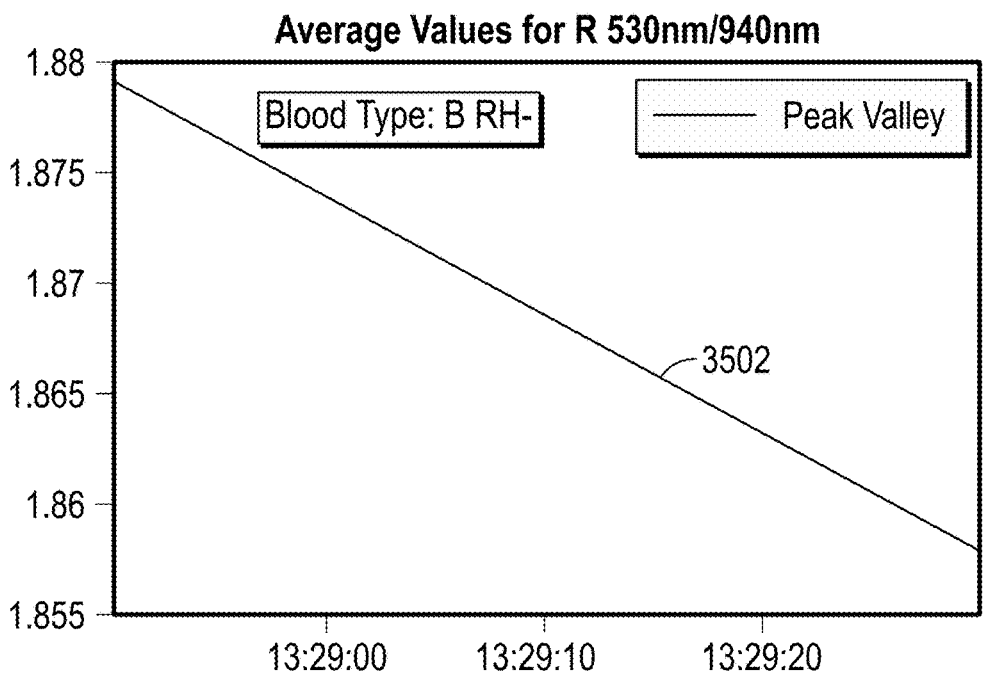
FIG. 35B illustrates a schematic drawing of average values for the $R_{530/940}$ ratio obtained using an embodiment of the biosensor.

FIG. 35B illustrates a schematic drawing of average values for the $R_{530/940}$ ratio 3502 obtained using the biosensor 100. As seen in FIGS. 35A and 35B, the values for the $R_{530/940}$ ratio are determined over the sample window and an average R value over the sample window is obtained.

Figure 36A:
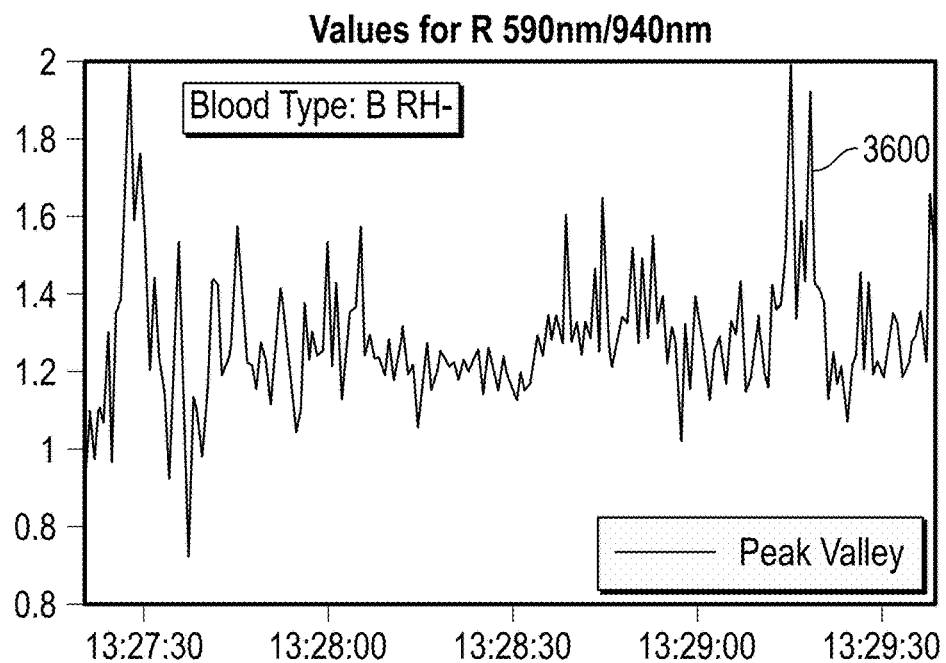
FIG. 36A illustrates a schematic drawing of values for the $R_{590/940}$ ratio obtained using the biosensor.

FIG. 36A illustrates a schematic drawing of values for the $R_{590/940}$ ratio 3600 obtained using the biosensor 100. The biosensor 100 obtained values for the $R_{590/940}$ ratio 3600 over a sample window of approximately two minutes. In this embodiment, it was known that the patient had a blood type of B RH−. An average of the values for the $R_{590/940}$ ratio 3600 over the sample window was obtained.

Figure 36B:
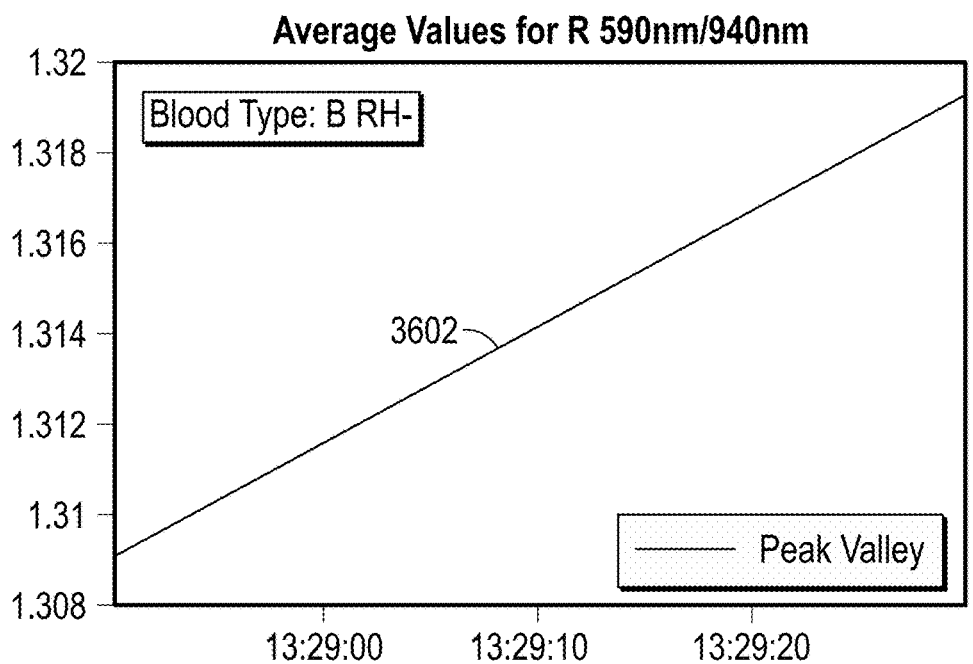
FIG. 36B illustrates a schematic drawing of average values for the $R_{590/940}$ ratio obtained using the biosensor.

FIG. 36B illustrates a schematic drawing of average values for the $R_{590/940}$ ratio 3602 obtained using the biosensor 100. As seen in FIGS. 35A and 35B, the values for the $R_{590/940}$ ratio are determined over the sample window and an average R value over the sample window is obtained.

In this example, the blood type indicators for the patient thus include an average $R_{530/940}$ value and an average $R_{530/940}$ value. The values for the $R_{530/940}$ ratio 3500 and the values for the $R_{590/940}$ ratio 3600 may be input into other functions or processes to obtain one or more blood type indicators.

Figure 37:
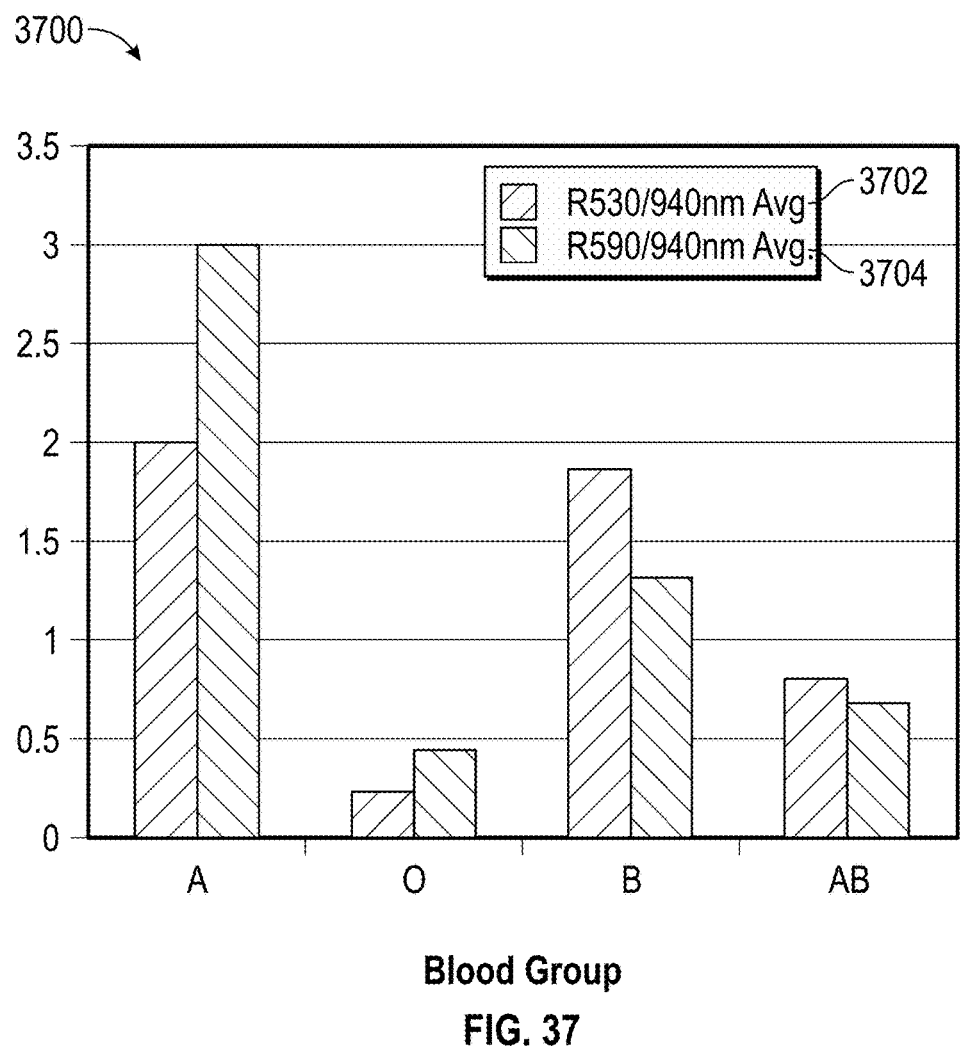
FIG. 37 illustrates a schematic drawing of an embodiment of a calibration table for blood groups.

FIG. 37 illustrates a schematic drawing of an embodiment of a calibration table for blood groups. The calibration table or blood group reference table 3700 includes an expected or know range of average values for R ratios for a plurality of the blood groups. The blood group reference table 3700 illustrates expected values for a plurality of blood group indicators for each blood group A, O, B, and AB. In this embodiment, the blood type indicators for the patient include an average $R_{530/940}$ value and an average $R_{530/940}$ value. The expected average values for the blood group indicators of $R_{530/940}$ ratio 3702 and $R_{590/940}$ ratio 3704 are shown for each of the blood groups A, O, B and AB.

To determine the blood group from the patient data shown in FIG. 35 and FIG. 36, the measured average $R_{530/940}$ value and $R_{590/940}$ value is compared to the blood group reference table 3700. The Blood Group type of B may thus be determined for the patient using the plurality of blood type indicators and the blood group reference table 3700.

Though the RH+ and RH− types are not shown in this blood group reference table 3700, a calibration graph or table may be used to determine the RH+ and RH− types of each Blood Groups A, B, AB and O. For example, the blood group A, B, AB and O may first be determined and then the RH+ and RH− types determined using the same or different blood type indicators. In another embodiment, the blood group A, B, AB and O and RH+ and RH− type may be determined using a same calibration table and blood type indicators. For example, values of the R ratio at 535 nm/940 nm may be used to detect either Rh+ or Rh−.

In another embodiment, though two blood type indicators are illustrated herein, three or more blood type indicators may be used to determine the blood type or a single blood type indicator may be used to determine the blood type. For example, a first blood type indicator may be determined and compared with the blood group reference table 3700. If the first blood type indicator fails to correlate with an expected value for a blood type, one or more additional blood type indicators may be obtained and compared with the blood group reference table 3700. In addition, though the blood group reference table 3700 illustrates a single expected value for each blood type indicator, the blood group reference table 3700 may indicate a range of expected values for one or more blood type indicators. The various R values indicate a presence of an antigen to identify a blood group of A, B, O or AB using the plurality of spectral responses. The PPG circuit may use the same R values or different R values to determine a presence of another antigen within a blood group to identify an RH factor using the plurality of spectral responses.

Figure 38:
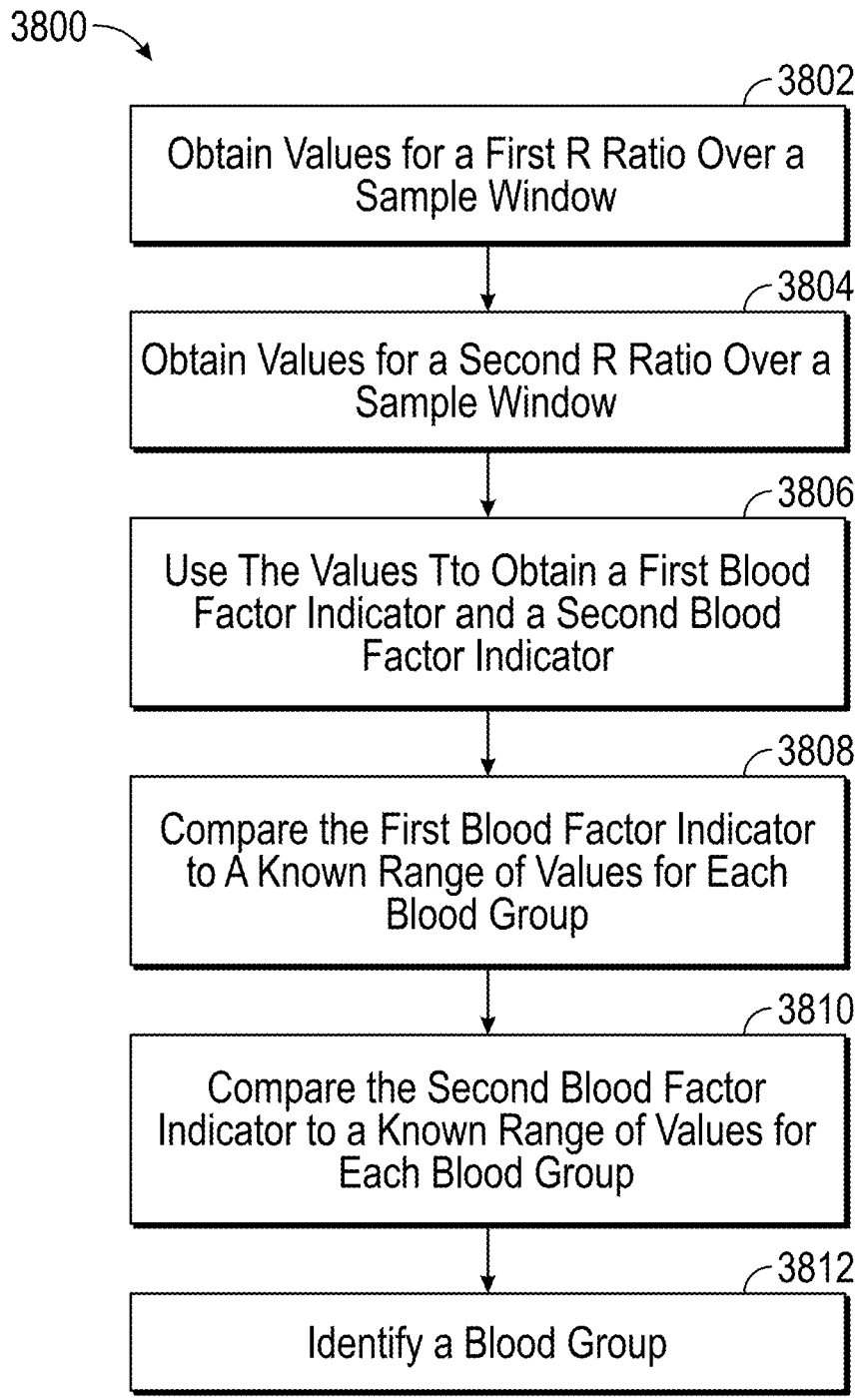
FIG. 38 illustrates a logical flow diagram of a method for obtaining a blood type using the biosensor.

FIG. 38 illustrates a logical flow diagram of a method 3800 for obtaining a blood type using the biosensor 100. The biosensor 100 obtains values for a first R ratio over a sample window at 3802. The biosensor 100 obtains values for a second R ratio over a sample window at 3804. The values of the first and second R ratios are used to obtain a first blood factor indicator and a second blood factor indicator at 3806. For example, the blood factor indicator may be derived from an average, mean or integration of the values of the R ratio over the sample window. Other functions or processes may be used to determine a blood factor indicator from the values of a R ratio over a sample window.

The first blood factor indicator is compared to a range of expected or known values for each of a plurality of blood groups in a calibration table at 3808. The second blood factor indicator is compared to a range of expected or known values for each of a plurality of blood groups in a calibration table at 3810. Based on the first or second comparison or both, a blood group is identified at 3812.

The biosensor 100 may thus be configured to determine a blood group A, B, O, AB and RH+ and RH− using one or more blood type indicators and a blood group reference table 3700. A blood type indicator is obtained using values of an R ratio over a sample window. A different R ratio and blood type indicator may be used for comparison based on the blood group A, B, O, AB. For example, an expected range of values for a first blood type indicator derived from a first R ratio may be listed for blood group A while an expected range of values for a second blood type indicator derived from a second R ratio may be listed for blood group O. The biosensor 100 may obtain the first and/or second blood type indicators in series or parallel and use the calibration table to determine the blood type.

The blood type varies the color of blood and may affect measurements of a PPG circuit 110, including a pulse oximeter. For example, the R ratio derived from a 660 nm spectral response varies in response to a blood type of a patient. Thus, depending on the type of measurement and R ratio, the biosensor 100 may use the blood type of a patient as a factor in its calibration tables. For example, a PPG circuit may use blood type of the patient as a factor in calibration tables when determining $SpO_2$. The biosensor then performs $SpO_2$ measurements. For example, a first spectral response around approximately 660 nm and a second spectral response around approximately 940 nm are obtained to determine a ratio $R_{660/940}$. The biosensor 100 then accesses a calibration table to determine an $SpO_2$ value using the ratio $R_{660/940}$ and blood type. For example, the biosensor 100 may include a different correlation between oxygen saturation values and R values for different blood types.

Figure 39:
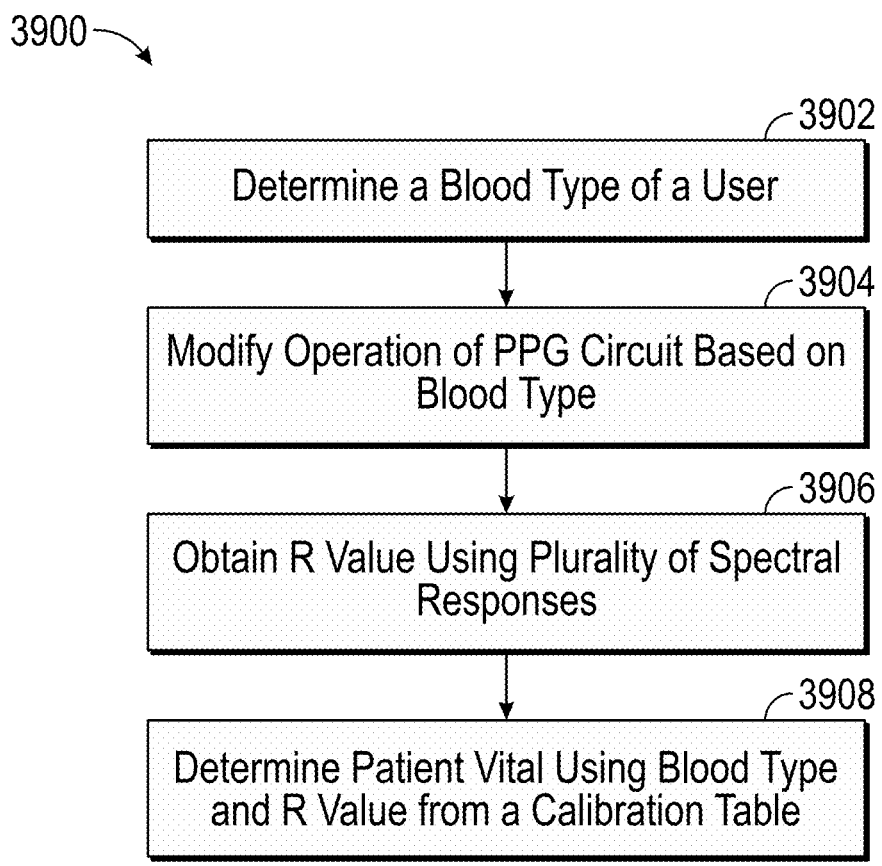
FIG. 39 illustrates a logical flow diagram of a method for determining a patient measurement using a blood type with the biosensor.

FIG. 39 illustrates a logical flow diagram of a method 3900 for determining a patient measurement using a blood type with the biosensor 100. The biosensor 100 determines a blood type of a user at 3902. The patient may input a known blood type or the biosensor 100 may use the PPG circuit 110 as described herein to obtain the blood type. Based on the blood type, the biosensor 100 may modify operation of the PPG circuit 110 or other components of the biosensor 100 at 3904. For example, a different frequency or intensity of light may be used to obtain one or more spectral responses. The biosensor 100 then obtains values for an R ratio or other types of measurements (e.g., absorption spectra shift) using a plurality of spectral responses at 3906. Based on the measurement and the blood type, a patient vital is determined from a calibration table. For example, the calibration table may include different values for an R ratio that correlate to a patient vital for different blood groups. In another example, the calibration table may include different values for an absorption spectra shift that correlate to a patient vital for different blood groups. The patient vital may include $SpO_2$, a concentration level of a substance, or other measurement.

Embodiment—Level of Vasodilation

Vasodilation refers to the widening of blood vessels. It results from relaxation of smooth muscle cells within the vessel walls. A substance that causes dilation of blood vessels by promoting the relaxation of vascular smooth muscle are referred to as vasodilators. Chemical vasodilators include hydralazine, nitroglycerin, nitroprusside, nesiritide, and trimethaphan. The biosensor 100 may process a spectral response to obtain a level of dilation of the arteries of a patient. For example, upon ingestion of food, blood gases such as NO are released and cause dilation of the vessels. The infrared (IR) spectral measurement increases in intensity due to increased blood flow through the dilated arteries. The increase in intensity of a spectral response of IR light may be measured and mapped to a level of dilation. A spectral response of UV light may also be measured and mapped to a level of dilation. The level of vasodilation may thus be measured using the spectral responses of light in the IR or UV range.

Embodiment—Health Assessment Biosensor in a Vehicle

The biosensor 100 may be integrated in a vehicle, such as a car, truck, motorcycle, train, plane, boat, bicycle, etc. The biosensor 100 may then measure patient vitals, such as heart rate, respiratory rate, SPO2, and temperature. The biosensor 100 may also be configured to determine other biosensor data such as blood type, level of vasodilation, infection, blood alcohol level, glucose level, dehydration, or other parameters. The biosensor data may be displayed on a vehicle display or provided via an audio output. In response to the biosensor data, the vehicle may be configured to perform one or more operations. For example, the vehicle may be configured to remain in a neutral or park or to not start the engine upon detection of blood alcohol levels over a predetermined threshold. In another example, the vehicle may initiate a self-driving mode when patient vitals indicate a severe health emergency in a driver. In yet another example, the vehicle may provide a warning when a patient's glucose or other patient vital reaches a predetermined threshold.

In another example, the biosensor data may be communicated to a remote healthcare service provider, and appropriate first aid can be communicated to the driver or other occupants of the vehicle. In the event of emergency conditions, the vehicle may be configured to active an alarm and notify emergency medical services.

Alcohol impaired driving is a major road safety issue of international concern. By integrating biosensors 110 into selected vehicle touch points, manufacturers or authorities may configure a vehicle to prevent operation by an impaired driver.

Figure 40:
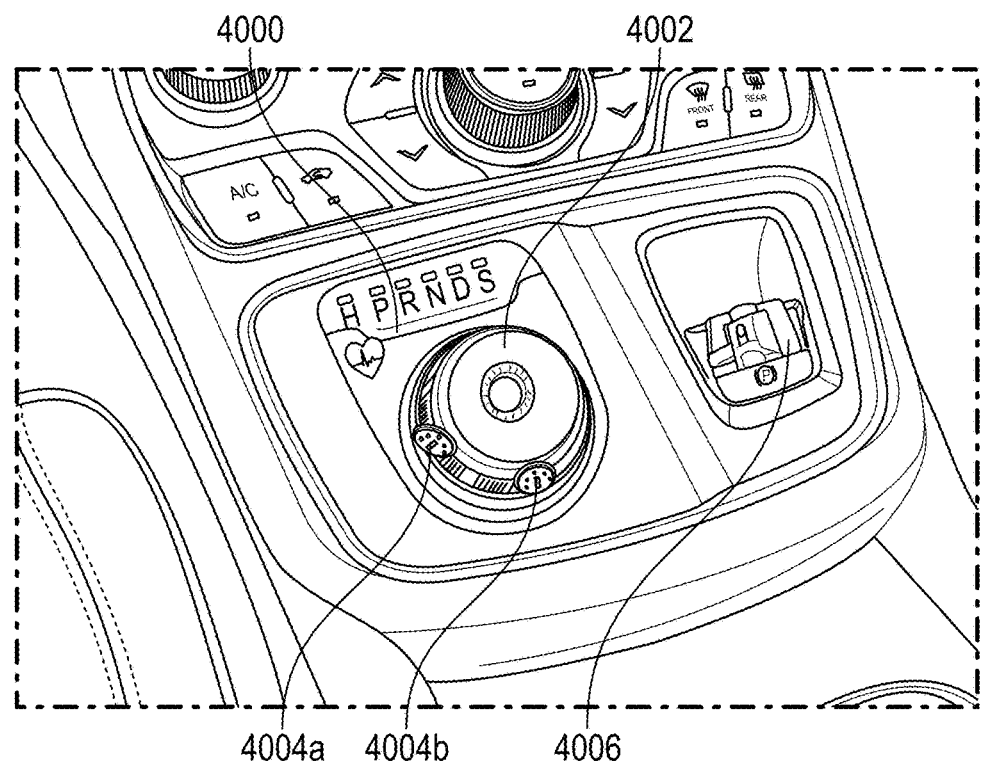
FIG. 40 illustrates an elevational view of an embodiment of a mechanism to initiate a health assessment by a biosensor in a vehicle.

FIG. 40 illustrates an elevational view of an embodiment of a mechanism to initiate a health assessment by a biosensor 100 in a vehicle. The mechanism in this embodiment is a PRNDS dial 4002 with an additional "Health Assessment" mode 4000. The PRNDS dial 4002 may be turned or pushed to initiate a "Health Assessment" mode 4000. The PRNDS dial 4002 includes a first finger sensor 4004a and a second finger sensor 4004b. When turning the PRNDS dial 4002, a user places their fingers on the finger sensors 4004. The finger sensors 4004 may include touchpads or touchpoints with integrated PPG circuit 110 and/or temperature sensor 112. A finger attachment 4006, such as shown in FIG. 19A, may be included in the vehicle as well for determining biosensor data. The finger attachment 4006 may be included as part of a parking brake lever or as a separate attachment. The finger attachment 4006 may include a transceiver for wireless or wired communication to the vehicle. A head rest or arm rest may also include a touchpad or touchpoint with integrated PPG circuit 110 and/or temperature sensor. The biosensor 100 may also be integrated in the vehicle in other form factors, such as a wrist band, patch, earpiece, etc.

Figure 41:
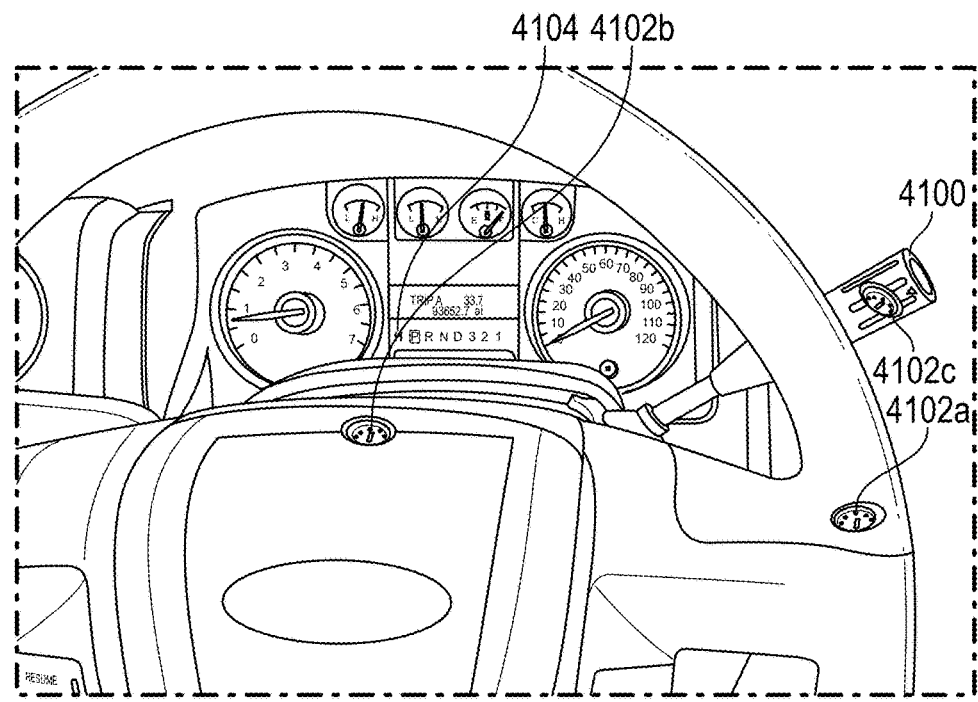
FIG. 41 illustrates an elevational view of an embodiment of another mechanism to initiate a health assessment by a biosensor in a vehicle.

FIG. 41 illustrates an elevational view of an embodiment of another mechanism to initiate a health assessment by a biosensor 100 in a vehicle. In this example, a lever 4100 may be engaged to active a "Health Assessment" mode 4104. One or more touchpads, touchpoints or finger sensors 4102a, 4102b are positioned on a steering wheel. In addition or alternatively, one or more finger sensors 4102c may be positioned on the lever 4100.

Figure 42:
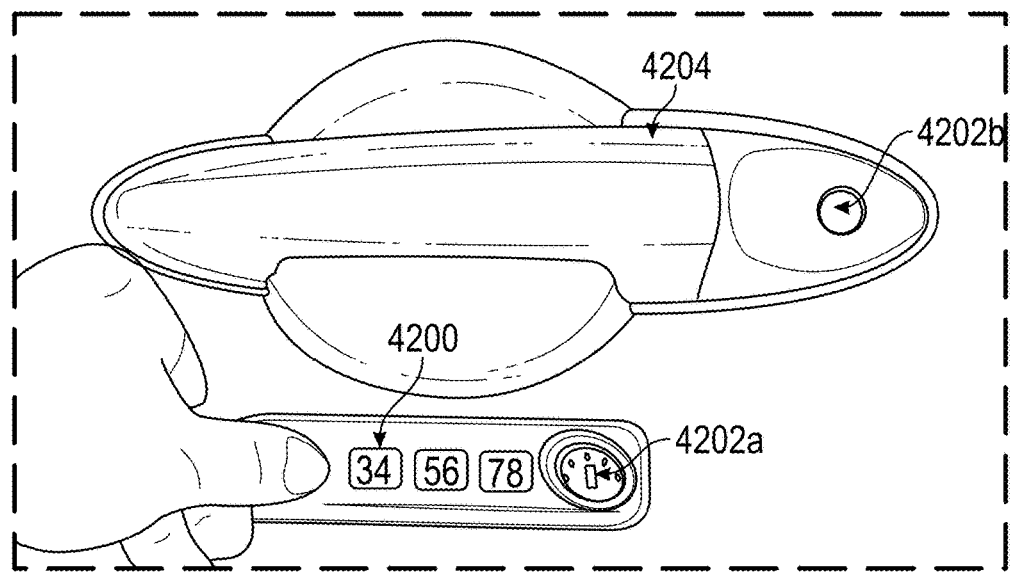
FIG. 42 illustrates an elevational view of an embodiment of another mechanism to initiate a health assessment by a biosensor in a vehicle

FIG. 42 illustrates an elevational view of an embodiment of another mechanism to initiate a health assessment by a biosensor 100 in a vehicle. In this example, a door entry system 4200 may be engaged to lock or unlock a vehicle. The door entry system 4200 may also include one or more finger sensors 4202a. In addition or alternatively, one or more finger sensors 4202b may be positioned on a door handle 4204.

The one or more finger sensors 4004, 4102, 4202 include a touch pad or touch point with a PPG circuit 110 and/or temperature sensor 112. The PPG circuit 110 may obtain biosensor data such as heart rate, respiratory rate, and SPO2. The PPG circuit 110 may also be configured to determine other biosensor data such as blood type, level of vasodilation, infection, blood alcohol level, glucose level, dehydration, or other substances and biomarkers in blood flow. The biosensor 100 may also be integrated in the vehicle in other form factors, such as a wrist band, patch, earpiece, etc. Alternatively to the integrated biosensors 100, a standalone biosensor 100 may communicate biosensor data to a vehicle over a wireless or wired interface.

Figure 43:
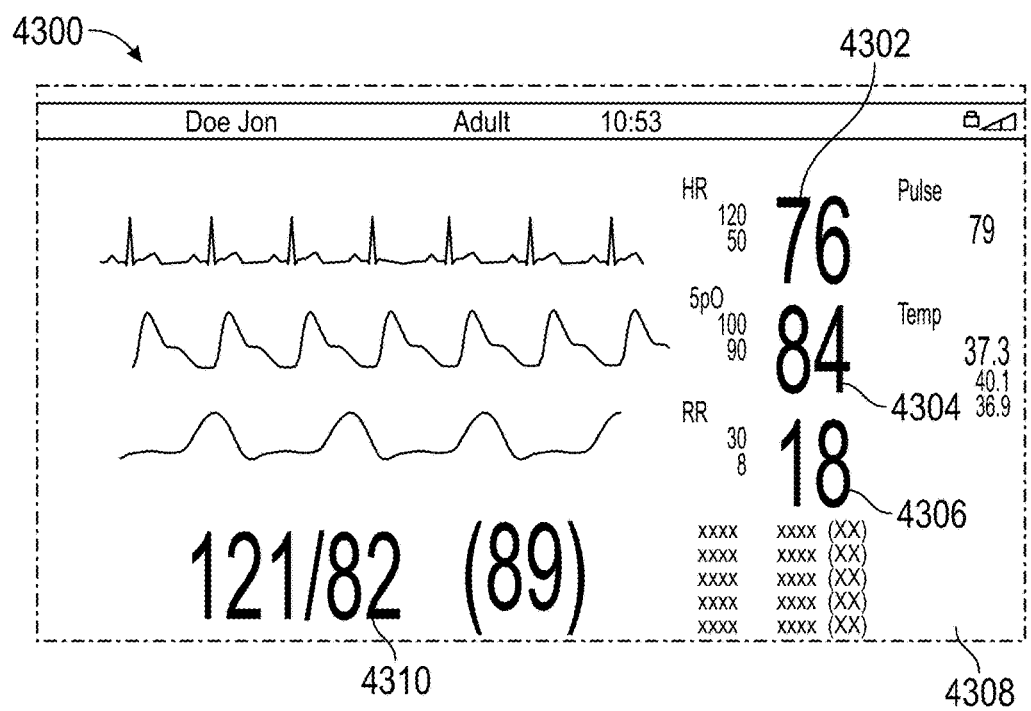
FIG. 43 illustrates an elevational view of an embodiment of a vehicle display of a health assessment by a biosensor.

FIG. 43 illustrates an elevational view of an embodiment of a vehicle display 4300 of a health assessment by a biosensor 100. The vehicle display may be a center console or other integrated display in the vehicle. The vehicle display 4300 shows a GUI including one or more of the patient vitals or other biosensor data from the health assessment. For example, the vehicle display 4300 may include a heart rate 4302, $SpO_2$ 4304, a respiratory rate 4306, a temperature 4308, or a blood pressure 4310. Other vitals and biosensor data may also be displayed.

Figure 44:
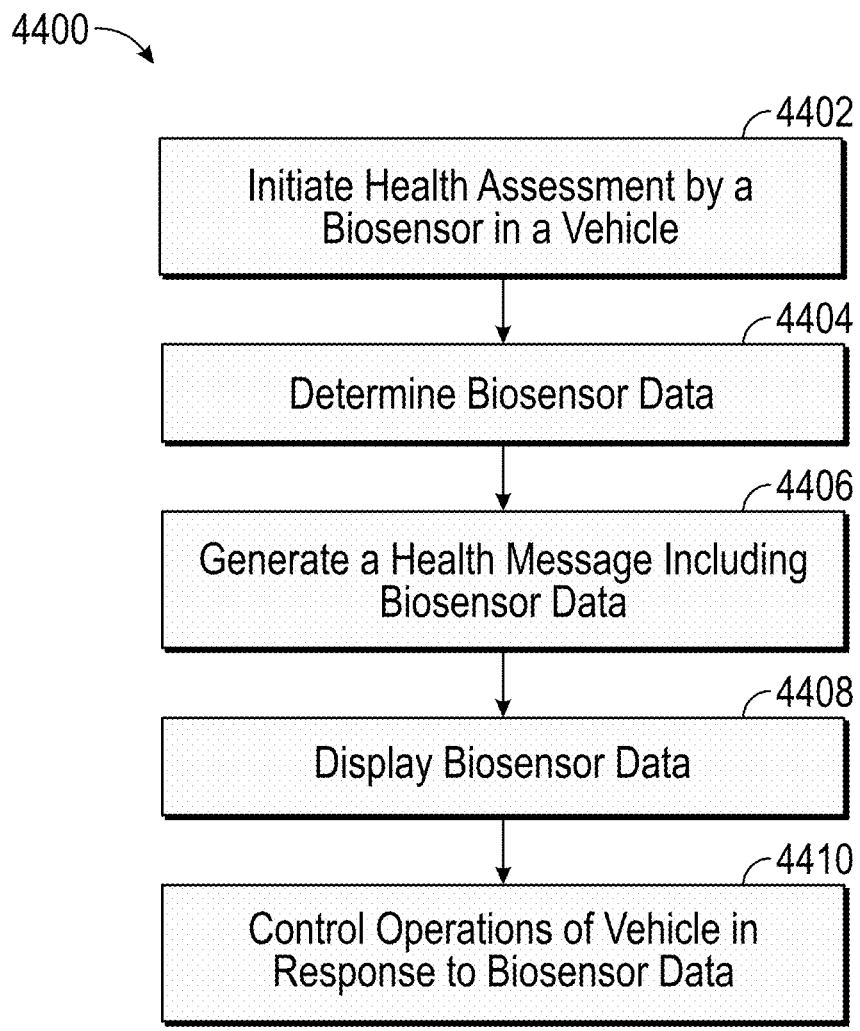
FIG. 44 illustrates a logical flow diagram of an embodiment of a method for controlling operations of a vehicle in response to biosensor data.

FIG. 44 illustrates a logical flow diagram of an embodiment of a method 4400 for controlling an operation of a vehicle in response to biosensor data. A health assessment is initiated in a vehicle at 4402. The health assessment may be initiated by activating a lever or a dial in the vehicle. The health assessment may also be initiated by positioning a finger on or in a finger sensor 4004, 4102, 4202. Once initiated, the biosensor 100 then determines biosensor data of an occupant of the vehicle at 4404. The occupant may be a driver, passenger or other user entering the vehicle or inside the vehicle. The biosensor 100 measures vitals, such as heart rate, respiratory rate, $SPO_2$, and temperature of the occupant. The biosensor 100 may also be configured to determine other biosensor data such as blood type, level of vasodilation, infection, blood alcohol level, glucose level, dehydration, or other parameters. The biosensor 100 may then generate a health message including the biosensor data of the occupant at 4406.

In response to the health message, the vehicle may determine to generate a GUI to present the biosensor data on a vehicle display or provide via an audio output of the biosensor data at 4408. The vehicle may also be configured to perform other operations at 4410. In one aspect, the vehicle may issue warnings, on the display and/or via audio alerts, when the biosensor data exceeds one or more predetermined thresholds. For example, when the vehicle determines a heart rate or a glucose level exceeds a normal range, the vehicle may control the display to generate a warning. In another example, the vehicle may determine to initiate a self-driving mode, e.g. when the biosensor data indicates a driver is in distress. The vehicle may determine not to allow ignition, e.g. when a blood alcohol level exceeds a threshold. The vehicle may transmit the biosensor data over a wireless wide area network, such as a cellular network, to a third party service provider. The third party service provider may include an emergency alert system or 911 service or health care provider. These and other operations may be performed in response to the biosensor data.

Figure 45:
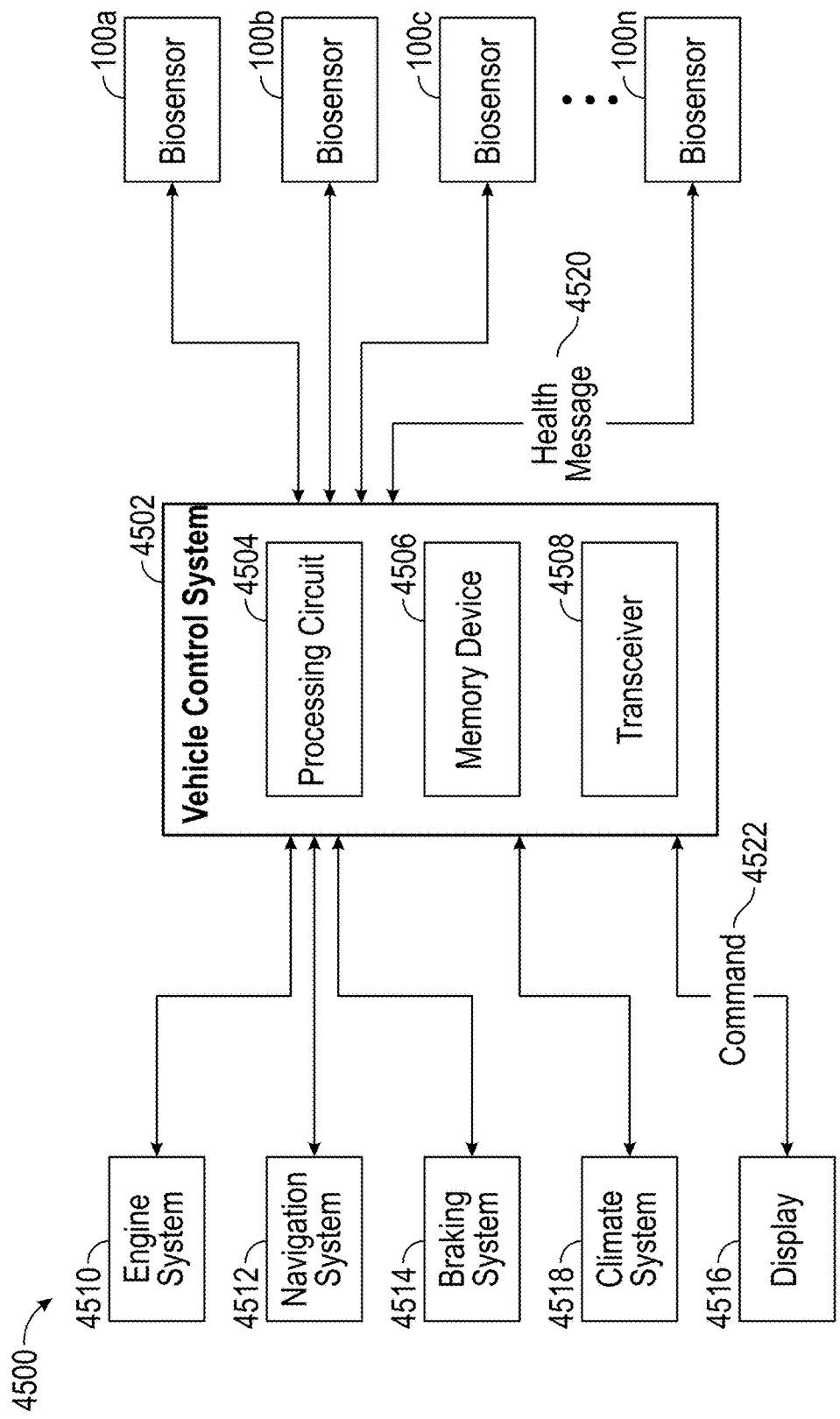
FIG. 45 illustrates a schematic block diagram of an embodiment of a vehicle with integrated biosensors.

FIG. 45 illustrates a schematic block diagram of an embodiment of a vehicle 4500 with integrated biosensors 100*a-n*. The vehicle 4500 includes a vehicle control system 4502 having a processing circuit 4504 and memory device 4506. In one aspect, the memory device 104 may include one or more non-transitory processor readable memories that store instructions which when executed by the processing circuit 4504, causes the processing circuit 102 to perform one or more functions described herein. The vehicle control system 4502 further includes a transceiver 4508 operable to communicate with the integrated biosensors 100*a-n* or standalone biosensor and other internal components of the vehicle 4500. The transceiver 4508 includes a wireless or wired transceiver configured to communicate with one or more devices over a LAN, MAN and/or WAN. In one aspect, the wireless transceiver may include a Bluetooth enabled (BLE) transceiver or IEEE 802.11ah, Zigbee, IEEE 802.15-11 or WLAN (such as an IEEE 802.11 standard protocol) compliant transceiver. In another aspect, the transceiver 4508 may operate using RFID, short range radio frequency, infrared link, or other short range wireless communication protocol. In another aspect, the wireless transceiver may also include or alternatively include an interface for communicating over a cellular network, WiMAX or other wide area wireless network.

The plurality of biosensors 100*a-n* may include the finger sensors 4004, 4102, 4202 or other type of sensor integrated into components of the vehicle. The biosensors 100*a-n* may include a PPG circuit 110 and temperature sensor 112 or other sensors described herein and employ the processing circuit 4504 of the vehicle control system 4502 to perform one or more functions described herein with respect to the biosensor 100. In other embodiments, the biosensors 100*a-n* may employ one or more separate processing circuits.

The vehicle control system 4502 is configured to control or generate commands 4522 or requests to one or more systems of the vehicle 4500 including the engine 4510, navigation system 4512, braking system 4514, display 4516 and climate system 4518. Though shown as a separate system, the vehicle control system 4502 may be incorporated within one or more of the other systems of the vehicle 4500. In addition to or alternatively, the biosensors 100*a-n* may transmit biosensor data or commands 4522 directly to one or more systems of the vehicle 4500.

During operation, one or more of the biosensors 100*a-n* obtain biosensor data of an occupant and generate a health message 4520 for transmission to the vehicle control system 4502, wherein the health message includes the biosensor data or other alerts. In response to the biosensor data, the vehicle 4500 may be configured to perform one or more operations as described herein. The vehicle control system 4502 may generate one or more GUIs to present biosensor data on the display 4516 as well as present user commands to control the biosensors 100*a-n*. For example, the display 4516 may include a touch screen or pad to select commands on the display 4516 to control operation of the biosensor 100*a-n*. The vehicle control system 4502 may also issue warnings, on the display and/or via audio alerts, when biosensor data exceeds a predetermined threshold. For example, if a driver's heart rate or a glucose level exceeds a normal range, the vehicle control system 4502 may control the display to generate a warning. The vehicle may transmit the biosensor data using the transceiver 4508 over a wide area network, such as a cellular network, to a third party service provider or over a LAN, e.g. via a Bluetooth or WLAN interface, to a user device.

Figure 46:
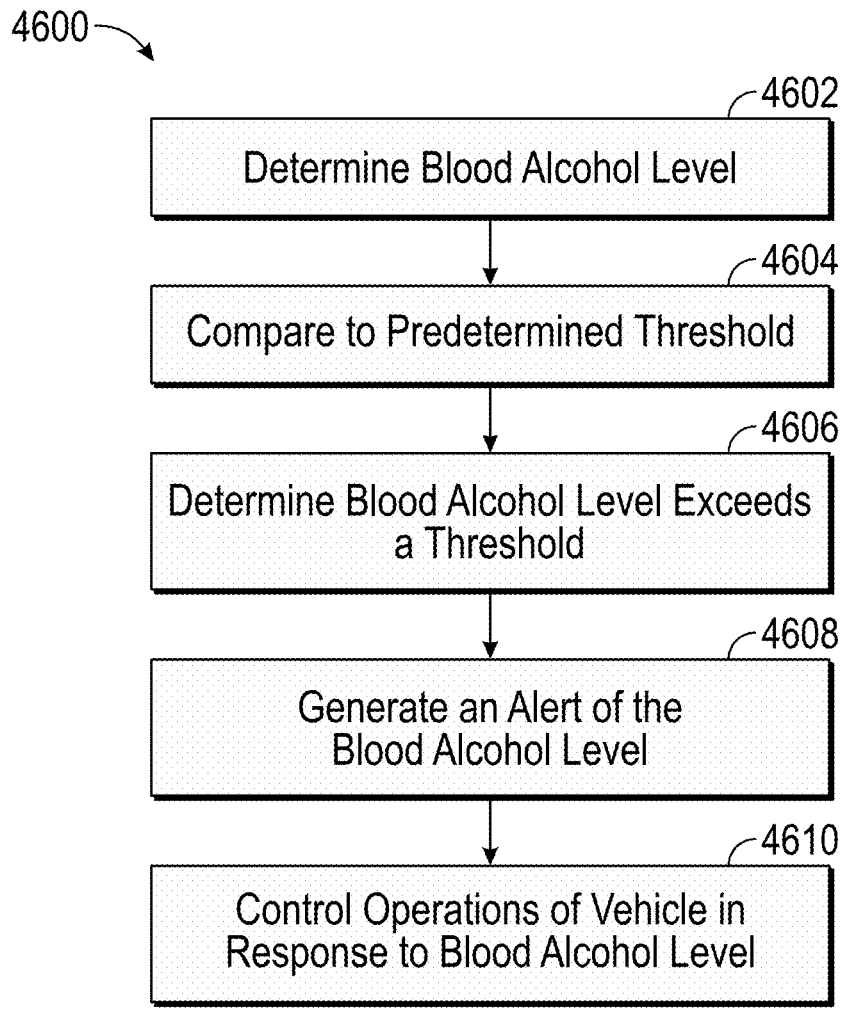
FIG. 46 illustrates a logic flow diagram of an embodiment of a method for controlling operation of the vehicle in response to an obtained blood alcohol level.

FIG. 46 illustrates a logic flow diagram of an embodiment of a method 4600 for controlling operation of the vehicle 4500 in response to a blood alcohol level. One or more of the integrated biosensors 100 of the vehicle include a PPG circuit 110 that obtains a blood alcohol level using a plurality of spectral responses at 4602. For example, a user may place a finger on one of the finger sensors 4004, 4102, 4202. The PPG circuit 110 then obtains a plurality of spectral responses, and the biosensor 100 uses the plurality of spectral responses to determine one or more indicators of blood alcohol levels, e.g. any combination of P450 or ethanol or NADH or other enzyme alcohol dehydrogenase (ADH) derivative. The biosensor 100 then transmits a health message to the vehicle control system 4502 including the blood alcohol level of the user.

The vehicle control system 4502 then compares the blood alcohol level to a predetermined threshold at 4604. The vehicle control system 4502 may then determine the blood alcohol level exceeds the predetermined threshold at 4606. The vehicle control system 4502 may then generate an alert or notification of the blood alcohol level at 4608. For example, the notification may indicate that the blood alcohol level exceeds the predetermined threshold.

The notification may be displayed on a vehicle display or transmitted to a user device over a short range wireless network or to a third party service provider over a wide area wireless network. The vehicle control system 4502 may also generate a command 4522 to prevent one or more operations of the vehicle 4500 in response to the blood alcohol level at 4610. For example, a command may be generated to an ignition system or engine to prevent the vehicle from starting or shifting out of park. Though the vehicle control system is described as performing various operations herein, one or more of the operations described herein may alternatively be performed by one or more of the biosensors 100a-n.

CONCLUSION

One or more embodiments have been described herein for one or more biosensors 100a-n configured for integration in a vehicle 4500. Due to its compact form factor, the biosensors 100 may be configured to be integrated as finger sensors 4004, 4102, 4202 or other type of sensors integrated in the vehicle 4500. The integrated biosensors 100 are configured to detect biosensor data, such as a patient's vitals or concentration level of one or more substances in the blood flow of a user. In particular, the PPG circuit 110 is configured to monitor a concentration level or indicator of one or more substances in the blood flow of the patient. In one aspect, the PPG circuit 110 may non-invasively and continuously detect diabetic parameters, such as insulin resistance, insulin response over time, nitric oxide (NO) levels, glucose levels, and predict diabetic risk or diabetic precursors, in blood flow. In another aspect, the PPG circuit 110 may measure vascular health using NO concentration levels. In another aspect, the PPG circuit 110 may detect blood alcohol levels in blood flow. In another aspect, the PPG circuit 110 may detect a blood group, such A, B, O, AB and RH+ and RH−. In another aspect, the PPG circuit 110 may detect a level of vasodilation. The PPG circuit 110 may detect various electrolyte concentration levels or blood analyte levels, such as bilirubin and sodium and potassium. For example, the PPG circuit 110 may detect a sodium or NACL concentration level in the arterial blood flow to determine a level of dehydration. In yet another aspect, the PPG circuit 110 may be configured to determine a risk of infection.

A vehicle control system 4502 of a vehicle 4500 may receive the biosensor data and control operations of one or more system or data of the vehicle 4500 in response to the biosensor data. The vehicle control system 4502 may generate one or more GUIs to present the biosensor data on the display 4516 of the vehicle 4500 or present user commands for controlling the biosensors 100a-n. The vehicle control system 4502 may also generate warnings in response to the biosensor data exceeding one or more predetermined thresholds.

In one or more aspects herein, a processing module or circuit includes at least one processing device, such as a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. A memory is a non-transitory memory device and may be an internal memory or an external memory, and the memory may be a single memory device or a plurality of memory devices. The memory may be a read-only memory, random access memory, volatile memory, non-volatile memory, static memory, dynamic memory, flash memory, cache memory, and/or any non-transitory memory device that stores digital information.

As may be used herein, the term "operable to" or "configurable to" indicates that an element includes one or more of circuits, instructions, modules, data, input(s), output(s), etc., to perform one or more of the described or necessary corresponding functions and may further include inferred coupling to one or more other items to perform the described or necessary corresponding functions. As may also be used herein, the term(s) "coupled", "coupled to", "connected to" and/or "connecting" or "interconnecting" includes direct connection or link between nodes/devices and/or indirect connection between nodes/devices via an intervening item (e.g., an item includes, but is not limited to, a component, an element, a circuit, a module, a node, device, network element, etc.). As may further be used herein, inferred connections (i.e., where one element is connected to another element by inference) includes direct and indirect connection between two items in the same manner as "connected to".

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, frequencies, wavelengths, component values, integrated circuit process variations, temperature variations, rise and fall times, and/or thermal noise. Such relativity between items ranges from a difference of a few percent to magnitude differences.

Note that the aspects of the present disclosure may be described herein as a process that is depicted as a schematic, a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a function, a procedure, a subroutine, a subprogram, etc. When a process corresponds to a function, its termination corresponds to a return of the function to the calling function or the main function.

The various features of the disclosure described herein can be implemented in different systems and devices without departing from the disclosure. It should be noted that the foregoing aspects of the disclosure are merely examples and are not to be construed as limiting the disclosure. The description of the aspects of the present disclosure is intended to be illustrative, and not to limit the scope of the claims. As such, the present teachings can be readily applied to other types of apparatuses and many alternatives, modifications, and variations will be apparent to those skilled in the art.

In the foregoing specification, certain representative aspects of the invention have been described with reference to specific examples. Various modifications and changes may be made, however, without departing from the scope of the present invention as set forth in the claims. The specification and figures are illustrative, rather than restrictive, and modifications are intended to be included within the scope of the present invention. Accordingly, the scope of the invention should be determined by the claims and their legal equivalents rather than by merely the examples described. For example, the components and/or elements recited in any apparatus claims may be assembled or otherwise operationally configured in a variety of permutations and are accordingly not limited to the specific configuration recited in the claims.

Furthermore, certain benefits, other advantages and solutions to problems have been described above with regard to particular embodiments; however, any benefit, advantage, solution to a problem, or any element that may cause any particular benefit, advantage, or solution to occur or to become more pronounced are not to be construed as critical, required, or essential features or components of any or all the claims.

As used herein, the terms "comprise," "comprises," "comprising," "having," "including," "includes" or any variation thereof, are intended to reference a nonexclusive inclusion, such that a process, method, article, composition or apparatus that comprises a list of elements does not include only those elements recited, but may also include other elements not expressly listed or inherent to such process, method, article, composition, or apparatus. Other combinations and/or modifications of the above-described structures, arrangements, applications, proportions, elements, materials, or components used in the practice of the present invention, in addition to those not specifically recited, may be varied or otherwise particularly adapted to specific environments, manufacturing specifications, design parameters, or other operating requirements without departing from the general principles of the same.

Moreover, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is intended to be construed under the provisions of 35 U.S.C. § 112(f) as a "means-plus-function" type element, unless the element is expressly recited using the phrase "means for" or, in the case of a method claim, the element is recited using the phrase "step for."

The invention claimed is:

1. A biosensor configured for integration in a vehicle, comprising:
    a temperature sensor configured to measure a temperature of an occupant of the vehicle;
    a photoplethysmography (PPG) circuit configured to emit light at a plurality of wavelengths directed at skin tissue of the occupant of the vehicle and obtain a plurality of spectral responses around the plurality of wavelengths of light, wherein a first wavelength has a high absorption coefficient for an indicator of blood alcohol in blood flow and wherein a second wavelength has a low absorption coefficient for the indicator of blood alcohol in blood flow; and
    a processing circuit configured to:
        obtain a measurement value for the indicator of blood alcohol in blood flow using the first spectral response and the second spectral response;
        determine a blood alcohol level in blood flow using the measurement value for the indicator of blood alcohol;
        an oxygen saturation level and a heart rate using one or more of the plurality of spectral responses; and
        generate a health message for transmission to a vehicle control system including the blood alcohol level, oxygen saturation level, heart rate and temperature.

2. The biosensor of claim 1, wherein the indicator of blood alcohol includes an ADH related enzyme.

3. The biosensor of claim 2, wherein the indicator includes a P450 enzyme; and
    wherein the processing circuit is further configured to determine the blood alcohol level using the concentration level of the indicator and a calibration table.

4. The biosensor of claim 1, wherein the indicator further includes one or more of: an ADH related enzyme or ethanol.

5. The biosensor of claim 1, wherein the processing circuit is further configured to:
    compare the blood alcohol level to a predetermined threshold;
    determine the blood alcohol level exceeds the predetermined threshold; and
    generate an alert of the blood alcohol level to the vehicle control system.

6. The biosensor of claim 1, wherein the processing circuit is further configured to determine a level of vasodilation by:
    determining a change in intensity from one or more spectral responses of the plurality of spectral responses due to blood flow; and
    mapping the change in intensity to the level of vasodilation.

7. The biosensor of claim 1, wherein the processing circuit is further configured to determine a concentration level of at least one additional substance in blood flow using the plurality of spectral responses.

8. The biosensor of claim 1, wherein the processing circuit is further configured to determine a concentration level of nitric oxide (NO) in blood flow using the plurality of spectral responses.

9. The biosensor of claim 1, wherein the processing circuit is further configured to determine a concentration level of glucose in blood flow using the plurality of spectral responses.

10. The biosensor of claim 1, wherein the processing circuit is further configured to determine a presence of an antigen to identify a blood group of A, B, O or AB using the plurality of spectral responses.

11. The biosensor of claim 10, wherein the processing circuit is further configured to determine a presence of another antigen within a blood group to identify an RH factor using the plurality of spectral responses.

12. The biosensor of claim 1, wherein the processing circuit is further configured to determine a risk of an infection using the plurality of spectral responses.

13. A biosensor integrated in a vehicle, comprising:
    a photoplethysmography (PPG) circuit in the integrated biosensor configured to emit light at a plurality of wavelengths directed at skin tissue and obtain a plurality of spectral responses around the plurality of wavelengths of light, wherein a first wavelength of light has a high absorption coefficient for an indicator of blood alcohol in blood flow and wherein a second wavelength of light has a low absorption coefficient for the indicator of blood alcohol in blood flow; and
    a processing circuit configured to:
        obtain biosensor data using the plurality of spectral responses, wherein the biosensor data includes an oxygen saturation level, a heart rate and a concentration level of blood alcohol in blood flow;
        determine a concentration level of the indicator in blood flow, wherein the indicator includes one or more of: a P450 liver enzyme or an NADH enzyme;
        determine the blood alcohol level in blood flow using the concentration level of the indicator and a calibration table; and
        generate an occupant health message including the biosensor data of the occupant for display on a vehicle display.

14. The biosensor of claim 13, wherein the indicator further includes ethanol.

15. The biosensor of claim 14, wherein the processing circuit is further configured to:
   compare the blood alcohol level to a predetermined threshold;
   determine the blood alcohol level exceeds the predetermined threshold; and
   generate another occupant health message for transmission to a vehicle control system including a notification that the blood alcohol level exceeds the predetermined threshold.

16. The biosensor of claim 13, wherein the processing circuit is further configured to determine a concentration level of nitric oxide (NO) in blood flow.

17. The biosensor of claim 16, wherein the processing circuit is further configured to
   compare the concentration level of NO to one or more predetermined thresholds; and
   generate an indication of a risk of infection in response to the comparison.

18. The biosensor of claim 13, wherein the processing circuit is further configured to determine a concentration level of glucose in blood flow.

19. The biosensor of claim 13, wherein the processing circuit is configured to obtain the concentration level of the blood alcohol in blood flow using the plurality of spectral responses by:
   obtaining a value $L_{\lambda 1}$ using a first spectral response of the first wavelength of light having a high absorption coefficient for the indicator of blood alcohol in blood flow, wherein the value $L_{\lambda 1}$ isolates the first spectral response due to pulsating blood flow;
   obtain a value $L_{\lambda 2}$ using a second spectral response of the second wavelength of light having a low absorption coefficient for the indicator of blood alcohol in blood flow, wherein the value $L_{\lambda 2}$ isolates the second spectral response due to pulsating blood flow;
   obtain a value $R_{\lambda 1, \lambda 2}$ from a ratio of the value $L_{\lambda 1}$ and the value $L_{\lambda 2}$; and
   obtain the concentration level of the blood alcohol using the value $R_{\lambda 1, \lambda 2}$ and a calibration table.

20. The biosensor of claim 13, wherein the processing circuit is further configured to determine a level of vasodilation by:
   determining a change in intensity from one or more spectral responses of the plurality of spectral responses due to blood flow; and
   mapping the change in intensity to the level of vasodilation.

21. The biosensor of claim 13, wherein the processing circuit is further configured to determine a presence of an antigen to identify a blood group of A, B, O or AB using the plurality of spectral responses.

22. The biosensor of claim 21, wherein the processing circuit is further configured to determine a presence of another antigen within a blood group to identify an RH factor using the plurality of spectral responses.

23. A biosensor, comprising:
   a photoplethysmography (PPG) circuit configured for integration in a vehicle and configured to obtain a first spectral response around a first wavelength of light having a high absorption coefficient for an indicator of blood alcohol in blood flow and a second spectral response around a second wavelength of light having a low absorption coefficient for the indicator of blood alcohol in blood flow; and
   a processing circuit configured to:
      obtain a concentration level of the indicator of blood alcohol in blood flow using the first and second spectral responses;
      obtain a blood alcohol level in blood flow using the concentration level of the indicator in blood flow, wherein the indicator of blood alcohol includes an ADH related enzyme; and
      transmit a health message including the blood alcohol level of the user to a vehicle control system.

24. The biosensor of claim 23, wherein the indicator of blood alcohol further includes ethanol.

25. The biosensor of claim 24, wherein the indicator includes at least a P450 enzyme; and
   wherein the processing circuit is further configured to determine the blood alcohol level using the indicator of the P450 enzyme and a calibration table.

26. The biosensor of claim 25, wherein the processing circuit is further configured to:
   compare the blood alcohol level to a predetermined threshold;
   determine the blood alcohol level exceeds the predetermined threshold; and
   wherein the health message includes a notification that the blood alcohol level exceeds the predetermined threshold.

27. A biosensor configured for integration in a vehicle, comprising:
   a temperature sensor configured to measure a temperature of an occupant;
   a photoplethysmography (PPG) circuit configured to emit light at a plurality of wavelengths directed at skin tissue of the occupant and obtain a plurality of spectral responses around the plurality of wavelengths of light; and
   a processing circuit configured to:
      process the plurality of spectral responses to obtain a plurality of health measurements, wherein the plurality of health measurements include a heart rate, an oxygen saturation level, a vasodilation level, and a concentration level of blood alcohol in blood flow;
      compare one or more of the plurality of measurements to one or more predetermined thresholds;
      determine the one or more of the plurality of measurements exceeds at least one of the predetermined thresholds; and
      generate an occupant health message to a vehicle control system.

28. The biosensor of claim 27, wherein the processing circuit is further configured to:
   transmit another occupant health message to a third party service provider over a wide area wireless network, wherein the third party service provider includes at least one of: an emergency service provider or a health care provider.

* * * * *